(12) United States Patent
Hasegawa et al.

(10) Patent No.: US 12,214,119 B2
(45) Date of Patent: *Feb. 4, 2025

(54) ELECTRICAL CONDENSATION AEROSOL DEVICE

(71) Applicant: ALEXZA PHARMACEUTICALS, INC., Mountain View, CA (US)

(72) Inventors: David Koji Hasegawa, Cupertino, CA (US); Mingzu Lei, San Jose, CA (US); Gilbert T. Tong, Union City, CA (US)

(73) Assignee: ALEXZA PHARMACEUTICALS, INC., Mountain View, CA (US)

( * ) Notice: Subject to any disclaimer, the term of this patent is extended or adjusted under 35 U.S.C. 154(b) by 1079 days.

This patent is subject to a terminal disclaimer.

(21) Appl. No.: 17/076,808

(22) Filed: Oct. 22, 2020

(65) Prior Publication Data

US 2021/0106775 A1    Apr. 15, 2021

Related U.S. Application Data

(63) Continuation of application No. 16/966,785, filed as application No. PCT/US2019/016398 on Feb. 1, 2019.

(Continued)

(51) Int. Cl.
*A61M 11/04*    (2006.01)
*A24F 40/20*    (2020.01)
(Continued)

(52) U.S. Cl.
CPC ......... *A61M 11/042* (2014.02); *A61M 11/001* (2014.02); *A24F 40/20* (2020.01);
(Continued)

(58) Field of Classification Search
CPC .............. A61M 11/042; A61M 11/001; A61M 2205/0233; A61M 2205/3334;
(Continued)

(56) References Cited

U.S. PATENT DOCUMENTS

| 1,239,634 A | 9/1917 | Stuart |
| 1,514,682 A | 11/1924 | Wilson |

(Continued)

FOREIGN PATENT DOCUMENTS

| CA | 2152684 | 1/1996 |
| CH | 436 297 | 5/1967 |

(Continued)

OTHER PUBLICATIONS

Office Action mailed Sep. 17, 2021 with respect to Canadian App No. 3,090,277 5 pages.

(Continued)

*Primary Examiner* — Valerie L Woodward
(74) *Attorney, Agent, or Firm* — Quarles & Brady LLP

(57) ABSTRACT

The present invention provides a method for producing condensation aerosols for the treatment of disease and/or chronic, intermittent or acute conditions. These condensation aerosols are produced from drugs including temperature sensitive drugs and small molecule drugs that are coated onto a foil substrate which is heated via electrical resistance heating at precisely controlled temperature profiles with controllable ramp-up and heating rates to vaporize the coated drug which subsequently condenses to form aerosol particles. These condensation aerosols have little or no degradation products. Kits comprising a drug and a device for producing a condensation aerosol are also provided. Also disclosed, are methods for using these aerosols and kits and methods of making the aerosols.

26 Claims, 14 Drawing Sheets

Related U.S. Application Data

(60) Provisional application No. 62/626,388, filed on Feb. 5, 2018, provisional application No. 62/626,396, filed on Feb. 5, 2018, provisional application No. 62/625,757, filed on Feb. 2, 2018.

(51) Int. Cl.
*A24F 40/50* (2020.01)
*A61M 11/00* (2006.01)

(52) U.S. Cl.
CPC ...... *A24F 40/50* (2020.01); *A61M 2205/0233* (2013.01); *A61M 2205/3334* (2013.01); *A61M 2205/3368* (2013.01); *A61M 2205/6054* (2013.01); *A61M 2205/6072* (2013.01); *A61M 2205/8206* (2013.01)

(58) Field of Classification Search
CPC .. A61M 2205/3368; A61M 2205/6054; A61M 2205/6072; A61M 2205/8206; A24F 40/20; A24F 40/50
See application file for complete search history.

(56) References Cited

U.S. PATENT DOCUMENTS

| | | |
|---|---|---|
| 1,535,486 A | 4/1925 | Lundy |
| 1,803,334 A | 5/1931 | Lehmann |
| 1,864,980 A | 6/1932 | Curran |
| 2,084,299 A | 6/1937 | Borden |
| 2,086,140 A | 7/1937 | Silten |
| 2,230,753 A | 2/1941 | Klavehn |
| 2,230,754 A | 2/1941 | Klavehn |
| 2,243,669 A | 5/1941 | Clyne |
| 2,309,846 A | 2/1943 | Holm |
| 2,469,656 A | 5/1949 | Lienert |
| 2,714,649 A | 8/1955 | Critzer |
| 2,741,812 A | 4/1956 | Andre |
| 2,761,055 A | 8/1956 | Ike |
| 2,887,106 A | 5/1959 | Robinson |
| 2,898,649 A | 8/1959 | Murray |
| 2,902,484 A | 9/1959 | Horclois |
| 3,043,977 A | 7/1962 | Morowitz |
| 3,080,624 A | 3/1963 | Webber, III |
| 3,161,478 A | 12/1964 | Chessin |
| 3,164,600 A | 1/1965 | Janssen |
| 3,169,095 A | 2/1965 | Thiel |
| 3,200,819 A | 8/1965 | Gilbert |
| 3,219,533 A | 11/1965 | Mullins |
| 3,282,729 A | 11/1966 | Richardson |
| 3,296,249 A | 1/1967 | Bell |
| 3,299,185 A | 1/1967 | Oda |
| 3,371,085 A | 2/1968 | Reeder |
| 3,393,197 A | 7/1968 | Pachter |
| 3,433,791 A | 3/1969 | Bentley |
| 3,560,607 A | 2/1971 | Hartley |
| 3,701,782 A | 10/1972 | Hester |
| 3,749,547 A | 7/1973 | Gregory |
| 3,763,347 A | 10/1973 | Whitaker |
| 3,773,955 A | 11/1973 | Pachter |
| 3,831,606 A | 8/1974 | Damani |
| 3,847,650 A | 11/1974 | Gregory |
| 3,864,326 A | 2/1975 | Babington |
| 3,882,323 A | 5/1975 | Smolker |
| 3,894,040 A | 7/1975 | Buzby, Jr. |
| 3,909,463 A | 9/1975 | Hartman |
| 3,930,796 A | 1/1976 | Haensel |
| 3,943,941 A | 3/1976 | Boyd |
| 3,949,743 A | 4/1976 | Shanbrom |
| 3,971,377 A | 7/1976 | Damani |
| 3,982,095 A | 9/1976 | Robinson |
| 3,987,052 A | 10/1976 | Hester, Jr. |
| 4,008,723 A | 2/1977 | Borthwick |
| 4,020,379 A | 4/1977 | Manning |
| 4,045,156 A | 8/1977 | Chu |
| 4,079,742 A | 3/1978 | Rainer |
| 4,104,210 A | 8/1978 | Coran |
| 4,121,583 A | 10/1978 | Chen |
| 4,141,369 A | 2/1979 | Burruss |
| 4,160,765 A | 7/1979 | Weinstock |
| 4,166,087 A | 8/1979 | Cline |
| 4,181,757 A | 1/1980 | Youdelis |
| 4,183,912 A | 1/1980 | Rosenthale |
| 4,184,099 A | 1/1980 | Lindauer |
| 4,189,200 A | 2/1980 | Yeager |
| 4,190,654 A | 2/1980 | Gherardi |
| 4,198,200 A | 4/1980 | Fonda |
| RE30,285 E | 5/1980 | Babington |
| 4,219,031 A | 8/1980 | Rainer |
| 4,229,447 A | 10/1980 | Porter |
| 4,229,931 A | 10/1980 | Schlueter |
| 4,232,002 A | 11/1980 | Nogrady |
| 4,236,544 A | 12/1980 | Osaka |
| 4,251,525 A | 2/1981 | Weinstock |
| 4,276,243 A | 6/1981 | Partus |
| 4,280,629 A | 7/1981 | Slaughter |
| 4,284,089 A | 8/1981 | Ray |
| 4,286,604 A | 9/1981 | Ehretsmann |
| 4,291,758 A | 9/1981 | Fujii |
| 4,303,083 A | 12/1981 | Burruss, Jr. |
| 4,340,072 A | 7/1982 | Bolt |
| 4,346,059 A | 8/1982 | Spector |
| 4,347,855 A | 9/1982 | Lanzillotti |
| 4,376,767 A | 3/1983 | Sloan |
| 4,391,285 A | 7/1983 | Burnett |
| 4,419,302 A | 12/1983 | Nishino |
| 4,419,650 A | 12/1983 | John |
| 4,423,071 A | 12/1983 | Chignac |
| 4,474,191 A | 10/1984 | Steiner |
| 4,484,576 A | 11/1984 | Albarda |
| 4,484,577 A | 11/1984 | Sackner |
| 4,508,726 A | 4/1985 | Coleman |
| 4,523,589 A | 6/1985 | Krauser |
| 4,539,575 A | 9/1985 | Nilsson |
| 4,556,539 A | 12/1985 | Spector |
| 4,566,451 A | 1/1986 | Badewien |
| 4,588,425 A | 5/1986 | Usry |
| 4,588,721 A | 5/1986 | Mahan |
| 4,591,615 A | 5/1986 | Aldred |
| 4,605,552 A | 8/1986 | Fritschi |
| 4,617,232 A | 10/1986 | Chandler |
| 4,627,963 A | 12/1986 | Olson |
| 4,647,428 A | 3/1987 | Gyulay |
| 4,647,433 A | 3/1987 | Spector |
| 4,654,370 A | 3/1987 | Marriott, III |
| 4,683,231 A | 7/1987 | Glassman |
| 4,693,868 A | 9/1987 | Katsuda |
| 4,708,151 A | 11/1987 | Shelar |
| 4,714,082 A | 12/1987 | Banerjee |
| 4,722,334 A | 2/1988 | Blackmer |
| 4,734,560 A | 3/1988 | Bowen |
| 4,735,217 A | 4/1988 | Gerth |
| 4,735,358 A | 4/1988 | Morita |
| 4,753,758 A | 6/1988 | Miller |
| 4,755,508 A | 7/1988 | Bock |
| 4,756,318 A | 7/1988 | Clearman |
| 4,765,347 A | 8/1988 | Sensabaugh, Jr. |
| 4,771,795 A | 9/1988 | White |
| 4,774,971 A | 10/1988 | Vieten |
| 4,793,365 A | 12/1988 | Sensabaugh, Jr. |
| 4,793,366 A | 12/1988 | Hill |
| 4,800,903 A | 1/1989 | Ray |
| 4,801,411 A | 1/1989 | Wellinghoff |
| 4,814,161 A | 3/1989 | Jinks |
| 4,819,665 A | 4/1989 | Roberts |
| 4,848,374 A | 7/1989 | Chard |
| 4,852,561 A | 8/1989 | Sperry |
| 4,853,517 A | 8/1989 | Bowen |
| 4,854,331 A | 8/1989 | Banerjee |
| 4,858,630 A | 8/1989 | Banerjee |
| 4,863,720 A | 9/1989 | Burghart |
| 4,881,541 A | 11/1989 | Eger |
| 4,881,556 A | 11/1989 | Clearman |
| 4,889,850 A | 12/1989 | Thornfeldt |

(56) References Cited

U.S. PATENT DOCUMENTS

| | | | |
|---|---|---|---|
| 4,892,109 A | 1/1990 | Strubel | |
| 4,895,719 A | 1/1990 | Radhakrishnun | |
| 4,906,417 A | 3/1990 | Gentry | |
| 4,911,157 A | 3/1990 | Miller | |
| 4,917,119 A | 4/1990 | Potter | |
| 4,917,120 A | 4/1990 | Hill | |
| 4,917,830 A | 4/1990 | Ortiz | |
| 4,917,960 A | 4/1990 | Hornberger | |
| 4,922,901 A * | 5/1990 | Brooks | A61M 16/109 131/273 |
| 4,924,883 A | 5/1990 | Perfetti | |
| 4,928,714 A | 5/1990 | Shannon | |
| 4,935,073 A | 6/1990 | Bartlett | |
| 4,935,624 A | 6/1990 | Henion | |
| 4,941,483 A | 7/1990 | Ridings | |
| 4,947,874 A | 8/1990 | Brooks | |
| 4,947,875 A | 8/1990 | Brooks | |
| 4,950,664 A | 8/1990 | Goldberg | |
| 4,955,945 A | 9/1990 | Weick | |
| 4,959,380 A | 9/1990 | Wilson | |
| 4,963,289 A | 10/1990 | Ortiz | |
| 4,968,885 A | 11/1990 | Willoughby | |
| 4,984,158 A | 1/1991 | Hillsman | |
| 4,989,619 A | 2/1991 | Clearman | |
| 5,016,425 A | 5/1991 | Weick | |
| 5,017,575 A | 5/1991 | Golwyn | |
| 5,019,122 A | 5/1991 | Clearman | |
| 5,020,548 A | 6/1991 | Farrier | |
| 5,027,836 A | 7/1991 | Shannon | |
| 5,033,483 A | 7/1991 | Clearman | |
| 5,038,769 A | 8/1991 | Krauser | |
| 5,042,509 A | 8/1991 | Banerjee | |
| 5,049,389 A | 9/1991 | Radhakrishnun | |
| 5,060,666 A | 10/1991 | Clearman | |
| 5,060,667 A | 10/1991 | Strubel | |
| 5,060,671 A | 10/1991 | Counts | |
| 5,067,499 A | 11/1991 | Banerjee | |
| 5,072,726 A | 12/1991 | Mazloomdoost | |
| 5,076,292 A | 12/1991 | Sensabaugh, Jr. | |
| 5,082,668 A | 1/1992 | Wong | |
| 5,093,894 A | 3/1992 | Deevi | |
| 5,095,921 A | 3/1992 | Loose | |
| 5,099,861 A | 3/1992 | Clearman | |
| 5,105,831 A | 4/1992 | Banerjee | |
| 5,109,180 A | 4/1992 | Boultinghouse | |
| 5,112,598 A | 5/1992 | Biesalski | |
| 5,118,494 A | 6/1992 | Schultz | |
| 5,119,834 A | 6/1992 | Shannon | |
| 5,126,123 A | 6/1992 | Johnson | |
| 5,133,368 A | 7/1992 | Neumann | |
| 5,135,009 A | 8/1992 | Muller | |
| 5,137,034 A | 8/1992 | Perfetti | |
| 5,144,962 A | 9/1992 | Counts | |
| 5,146,915 A | 9/1992 | Montgomery | |
| 5,149,538 A | 9/1992 | Granger | |
| 5,156,170 A | 10/1992 | Clearman | |
| 5,160,664 A | 11/1992 | Liu | |
| 5,164,740 A | 11/1992 | Ivri | |
| 5,166,202 A | 11/1992 | Schweizer | |
| 5,167,242 A | 12/1992 | Turner | |
| 5,168,866 A | 12/1992 | Montgomery | |
| 5,177,071 A | 1/1993 | Freidinger | |
| 5,179,966 A | 1/1993 | Losee | |
| 5,186,164 A | 2/1993 | Raghuprasad | |
| 5,192,548 A | 3/1993 | Velasquez | |
| 5,224,498 A | 7/1993 | Deevi | |
| 5,226,411 A | 7/1993 | Levine | |
| 5,229,120 A | 7/1993 | DeVincent | |
| 5,229,382 A | 7/1993 | Chakrabarti | |
| 5,240,922 A | 8/1993 | O'Neill | |
| 5,249,586 A | 10/1993 | Morgan | |
| 5,255,674 A | 10/1993 | Oftedal | |
| 5,261,424 A | 11/1993 | Sprin | |
| 5,264,433 A | 11/1993 | Sato | |
| 5,269,327 A | 12/1993 | Counts | |
| 5,284,133 A | 2/1994 | Burns | |
| 5,285,798 A | 2/1994 | Banerjee | |
| 5,292,499 A | 3/1994 | Evans | |
| 5,322,075 A | 6/1994 | Deevi | |
| 5,333,106 A | 7/1994 | Lanpher | |
| 5,345,951 A | 9/1994 | Serrano | |
| 5,357,984 A | 10/1994 | Farrier | |
| 5,363,842 A | 11/1994 | Mishelevich | |
| 5,364,838 A | 11/1994 | Rubsamen | |
| 5,366,770 A | 11/1994 | Wang | |
| 5,369,723 A | 11/1994 | Counts | |
| 5,372,148 A | 12/1994 | McCafferty | |
| 5,376,386 A | 12/1994 | Ganderton | |
| 5,388,574 A | 2/1995 | Ingebrethsen | |
| 5,391,081 A | 2/1995 | Lampotang | |
| 5,397,652 A | 3/1995 | Carey | |
| 5,399,574 A | 3/1995 | Robertson | |
| 5,400,808 A | 3/1995 | Turner | |
| 5,400,969 A | 3/1995 | Keene | |
| 5,402,517 A | 3/1995 | Gillett | |
| 5,408,574 A | 4/1995 | Deevi | |
| 5,431,167 A | 7/1995 | Savord | |
| 5,436,230 A | 7/1995 | Soudant | |
| 5,451,408 A | 9/1995 | Mezei | |
| 5,455,043 A | 10/1995 | Fischel-Ghodsian | |
| 5,456,247 A | 10/1995 | Shilling | |
| 5,456,677 A | 10/1995 | Spector | |
| 5,457,100 A | 10/1995 | Daniel | |
| 5,457,101 A | 10/1995 | Greenwood | |
| 5,459,137 A | 10/1995 | Andrasi | |
| 5,462,740 A | 10/1995 | Evenstad | |
| 5,468,936 A | 11/1995 | Deevi | |
| 5,479,948 A | 1/1996 | Counts | |
| 5,496,359 A | 3/1996 | Davidson | |
| 5,501,236 A | 3/1996 | Hill | |
| 5,505,214 A | 4/1996 | Collins | |
| 5,507,277 A | 4/1996 | Rubsamen | |
| 5,511,726 A | 4/1996 | Greenspan | |
| 5,518,179 A | 5/1996 | Humberstone | |
| 5,519,019 A | 5/1996 | Andrasi | |
| 5,554,646 A | 5/1996 | Lloyd | |
| 5,522,385 A | 6/1996 | Lloyd | |
| 5,525,329 A | 6/1996 | Snyder | |
| 5,537,507 A | 7/1996 | Mariner | |
| 5,538,020 A | 7/1996 | Farrier | |
| 5,540,959 A | 7/1996 | Wang | |
| 5,543,434 A | 8/1996 | Weg | |
| 5,544,646 A | 8/1996 | Lloyd | |
| 5,564,442 A | 10/1996 | MacDonald | |
| 5,565,148 A | 10/1996 | Pendergrass | |
| 5,577,156 A | 11/1996 | Costello | |
| 5,584,701 A | 12/1996 | Lampotang | |
| 5,586,550 A | 12/1996 | Ivri | |
| 5,591,409 A | 1/1997 | Watkins | |
| 5,592,934 A | 1/1997 | Thwaites | |
| 5,593,792 A | 1/1997 | Farrier | |
| 5,605,146 A | 2/1997 | Sarela | |
| 5,605,897 A | 2/1997 | Beasley, Jr. | |
| 5,607,691 A | 3/1997 | Hale | |
| 5,613,504 A | 3/1997 | Collins | |
| 5,613,505 A | 3/1997 | Campbell | |
| 5,619,984 A | 4/1997 | Hodson | |
| 5,622,944 A | 4/1997 | Hale | |
| 5,627,178 A | 5/1997 | Chakrabarti | |
| 5,641,938 A | 6/1997 | Holland | |
| 5,649,554 A | 7/1997 | Sprinkel | |
| 5,655,523 A | 8/1997 | Hodson | |
| 5,656,255 A | 8/1997 | Jones | |
| 5,660,166 A | 8/1997 | Lloyd | |
| 5,666,977 A | 9/1997 | Higgins | |
| 5,690,809 A | 11/1997 | Subramaniam | |
| 5,694,919 A | 12/1997 | Rubsamen | |
| 5,718,222 A | 2/1998 | Lloyd | |
| 5,724,957 A | 3/1998 | Rubsamen | |
| 5,725,756 A | 3/1998 | Subramaniam | |
| 5,733,572 A | 3/1998 | Unger | |
| 5,735,263 A | 4/1998 | Rubsamen | |
| 5,738,865 A | 4/1998 | Baichwal | |
| 5,743,250 A | 4/1998 | Gonda | |

(56) References Cited

U.S. PATENT DOCUMENTS

| | | | |
|---|---|---|---|
| 5,743,251 A | 4/1998 | Howell |
| 5,744,469 A | 4/1998 | Tran |
| 5,747,001 A | 5/1998 | Wiedmann |
| 5,756,449 A | 5/1998 | Andersen |
| 5,758,637 A | 6/1998 | Ivri |
| 5,767,117 A | 6/1998 | Moskowitz |
| 5,769,621 A | 6/1998 | Early |
| 5,770,222 A | 6/1998 | Unger |
| 5,771,882 A | 6/1998 | Psaros |
| 5,776,928 A | 7/1998 | Beasley, Jr. |
| 5,804,212 A | 9/1998 | Illum |
| 5,809,997 A | 9/1998 | Wolf |
| 5,817,656 A | 10/1998 | Beasley, Jr. |
| 5,819,756 A | 10/1998 | Mielordt |
| 5,823,178 A | 10/1998 | Lloyd |
| 5,829,436 A | 11/1998 | Rubsamen |
| 5,833,891 A | 11/1998 | Subramaniam |
| 5,840,246 A | 11/1998 | Hammons |
| 5,855,564 A | 1/1999 | Ruskewicz |
| 5,855,913 A | 1/1999 | Hanes |
| 5,858,118 A | 1/1999 | Shah |
| 5,865,185 A | 2/1999 | Collins |
| 5,874,064 A | 2/1999 | Edwards |
| 5,874,481 A | 2/1999 | Weers |
| 5,875,776 A | 3/1999 | Vaghefi |
| 5,878,752 A | 3/1999 | Adams |
| 5,884,620 A | 3/1999 | Gonda |
| 5,890,908 A | 4/1999 | Lampotang |
| 5,894,841 A | 4/1999 | Voges |
| 5,900,249 A | 5/1999 | Smith |
| 5,904,900 A | 5/1999 | Bleuse |
| 5,906,811 A | 5/1999 | Hersh |
| 5,907,075 A | 5/1999 | Subramaniam |
| 5,910,301 A | 6/1999 | Farr |
| 5,915,378 A | 6/1999 | Lloyd |
| 5,918,595 A | 7/1999 | Olsson |
| 5,928,520 A | 7/1999 | Haumesser |
| 5,929,093 A | 7/1999 | Pang |
| 5,934,272 A | 8/1999 | Lloyd |
| 5,934,289 A | 8/1999 | Watkins |
| 5,935,604 A | 8/1999 | Illum |
| 5,938,117 A | 8/1999 | Ivri |
| 5,939,100 A | 8/1999 | Albrechtsen |
| 5,941,240 A | 8/1999 | Gonda |
| 5,944,012 A | 8/1999 | Pera |
| 5,957,124 A | 9/1999 | Lloyd |
| 5,960,792 A | 10/1999 | Lloyd |
| 5,970,973 A | 10/1999 | Gonda |
| 5,971,951 A | 10/1999 | Ruskewicz |
| 5,980,566 A | 11/1999 | Alt |
| 5,985,309 A | 11/1999 | Edwards |
| 5,993,805 A | 11/1999 | Sutton |
| 6,004,516 A | 12/1999 | Rasouli |
| 6,004,970 A | 12/1999 | O'Malley |
| 6,008,214 A | 12/1999 | Kwon |
| 6,008,216 A | 12/1999 | Chakrabarti |
| 6,013,050 A | 1/2000 | Bellhouse |
| 6,014,969 A | 1/2000 | Lloyd |
| 6,014,970 A | 1/2000 | Ivri |
| 6,041,777 A | 3/2000 | Faithfull |
| 6,044,777 A | 4/2000 | Walsh |
| 6,048,550 A | 4/2000 | Chan |
| 6,048,857 A | 4/2000 | Ellinwood, Jr. |
| 6,050,260 A | 4/2000 | Daniell |
| 6,051,257 A | 4/2000 | Kodas |
| 6,051,566 A | 4/2000 | Bianco |
| 6,053,176 A | 4/2000 | Adams |
| RE36,744 E | 6/2000 | Goldberg |
| 6,085,026 A | 7/2000 | Hammons |
| 6,089,857 A | 7/2000 | Matsuura |
| 6,090,212 A | 7/2000 | Mahawili |
| 6,090,403 A | 7/2000 | Block |
| 6,095,134 A | 8/2000 | Sievers |
| 6,095,153 A | 8/2000 | Kessler |
| 6,098,620 A | 8/2000 | Lloyd |
| 6,102,036 A | 8/2000 | Slutsky |
| 6,113,795 A | 9/2000 | Subramaniam |
| 6,117,866 A | 9/2000 | Bondinell |
| 6,125,853 A | 10/2000 | Susa |
| 6,126,919 A | 10/2000 | Stefely |
| 6,131,566 A | 10/2000 | Ashurst |
| 6,131,570 A | 10/2000 | Schuster |
| 6,133,327 A | 10/2000 | Kimura |
| 6,135,369 A | 10/2000 | Prendergast |
| 6,136,295 A | 10/2000 | Edwards |
| 6,138,683 A | 10/2000 | Hersh |
| 6,140,323 A | 10/2000 | Ellinwood, Jr. |
| 6,143,277 A | 11/2000 | Ashurst |
| 6,143,746 A | 11/2000 | Daugan |
| 6,149,892 A | 11/2000 | Britto |
| 6,155,268 A | 12/2000 | Takeuchi |
| 6,158,431 A | 12/2000 | Poole |
| 6,167,880 B1 | 1/2001 | Gonda |
| 6,178,969 B1 | 1/2001 | St. Charles |
| 6,211,171 B1 | 4/2001 | Sawynok |
| 6,228,445 B1 | 5/2001 | Tverberg |
| 6,234,167 B1 | 5/2001 | Cox |
| 6,241,969 B1 | 6/2001 | Saidi |
| 6,250,298 B1 | 6/2001 | Gonda |
| 6,250,301 B1 | 6/2001 | Pate |
| 6,255,334 B1 | 7/2001 | Sands |
| 6,263,872 B1 | 7/2001 | Schuster |
| 6,264,922 B1 | 7/2001 | Wood |
| 6,284,287 B1 | 9/2001 | Sarlikiotis |
| 6,290,986 B1 | 9/2001 | Murdock |
| 6,299,900 B1 | 10/2001 | Reed |
| 6,300,710 B1 | 10/2001 | Nakamori |
| 6,306,431 B1 | 10/2001 | Zhang |
| 6,309,668 B1 | 10/2001 | Bastin |
| 6,309,986 B1 | 10/2001 | Flashinski |
| 6,313,176 B1 | 11/2001 | Ellinwood, Jr. |
| 6,315,985 B1 | 11/2001 | Wu |
| 6,325,475 B1 | 12/2001 | Hayes |
| 6,328,033 B1 | 12/2001 | Avrahami |
| 6,367,481 B1 | 4/2002 | Nichols |
| 6,376,550 B1 | 4/2002 | Raber |
| 6,390,453 B1 | 5/2002 | Frederickson |
| 6,408,854 B1 | 6/2002 | Gonda |
| 6,413,930 B1 | 7/2002 | Ratti |
| 6,420,351 B1 | 7/2002 | Tsai |
| 6,431,166 B2 | 8/2002 | Gonda |
| 6,435,175 B1 * | 8/2002 | Stenzler ............ A61M 15/0065 |
| | | 128/202.25 |
| 6,443,152 B1 | 9/2002 | Lockhart |
| 6,444,326 B1 | 9/2002 | Smith |
| 6,444,665 B1 | 9/2002 | Helton |
| 6,461,591 B1 | 10/2002 | Keller |
| 6,479,074 B2 | 11/2002 | Murdock |
| 6,491,233 B2 | 12/2002 | Nichols |
| 6,501,052 B2 | 12/2002 | Cox |
| 6,506,762 B1 | 1/2003 | Horvath |
| 6,514,482 B1 | 2/2003 | Bartus |
| 6,516,796 B1 | 2/2003 | Cox |
| 6,521,187 B1 | 2/2003 | Papen |
| 6,554,201 B2 | 4/2003 | Klimowicz |
| 6,557,552 B1 | 5/2003 | Cox |
| 6,561,186 B2 | 5/2003 | Casper |
| 6,568,390 B2 | 5/2003 | Nichols |
| 6,568,465 B1 | 5/2003 | Meissner |
| 6,591,839 B2 | 7/2003 | Meyer |
| 6,632,047 B2 | 10/2003 | Vinegar |
| 6,638,981 B2 | 10/2003 | Williams |
| 6,648,950 B2 | 11/2003 | Lee |
| 6,671,945 B2 | 1/2004 | Gerber |
| 6,680,668 B2 | 1/2004 | Gerber |
| 6,681,769 B2 | 1/2004 | Sprinkel |
| 6,681,998 B2 | 1/2004 | Sharpe |
| 6,682,716 B2 | 1/2004 | Hodges et al. |
| 6,684,880 B2 | 2/2004 | Trueba |
| 6,688,313 B2 | 2/2004 | Wrenn |
| 6,694,975 B2 | 2/2004 | Schuster |
| 6,701,921 B2 | 3/2004 | Sprinkel |
| 6,701,922 B2 | 3/2004 | Hindle |
| 6,709,739 B1 | 3/2004 | Mullen |

(56) References Cited

U.S. PATENT DOCUMENTS

| | | |
|---|---|---|
| 6,715,487 B2 | 4/2004 | Nichols |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,728,478 B2 | 4/2004 | Cox |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,772,756 B2 | 8/2004 | Shayan |
| 6,772,757 B2 | 8/2004 | Sprinkel, Jr. |
| 6,776,978 B2 | 8/2004 | Rabinowitz et al. |
| 6,779,520 B2 | 8/2004 | Genova |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,812,432 B1 | 11/2004 | Haluschka |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,979,437 B2 | 12/2005 | Bartus |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,040,314 B2 | 5/2006 | Nguyen |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,066,398 B2 | 6/2006 | Borland |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,088,914 B2 | 8/2006 | Whittle |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,364,897 B2 | 4/2008 | Heaney |
| 7,387,788 B1 | 6/2008 | Carrara |
| 7,402,777 B2 | 7/2008 | Hale et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,459,469 B2 | 12/2008 | Munoz |
| 7,465,435 B2 | 12/2008 | Rabinowitz et al. |
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,494,344 B2 | 2/2009 | Galauner et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,513,781 B2 | 4/2009 | Galauner et al. |
| 7,524,484 B2 | 4/2009 | Rabinowitz et al. |
| 7,537,009 B2 | 5/2009 | Hale et al. |
| 7,540,286 B2 | 6/2009 | Cross et al. |
| 7,550,133 B2 | 6/2009 | Hale et al. |
| 7,581,540 B2 | 9/2009 | Hale et al. |
| 7,585,493 B2 | 9/2009 | Hale et al. |
| 7,601,337 B2 | 10/2009 | Rabinowitz et al. |
| 7,645,442 B2 | 1/2010 | Hale et al. |
| 7,766,013 B2 | 8/2010 | Wensley et al. |
| 7,785,482 B2 | 8/2010 | Subramanian |
| 7,832,655 B2 | 11/2010 | Tollens |
| 7,834,295 B2 | 11/2010 | Sharma et al. |
| 7,913,688 B2 | 3/2011 | Cross et al. |
| 7,923,662 B2 | 4/2011 | Hale et al. |
| 7,942,147 B2 | 5/2011 | Hodges et al. |
| 7,981,401 B2 | 7/2011 | Every et al. |
| 7,987,846 B2 | 8/2011 | Hale et al. |
| 7,988,952 B2 | 8/2011 | Rabinowitz et al. |
| 8,003,080 B2 | 8/2011 | Rabinowitz et al. |
| 8,074,644 B2 | 12/2011 | Hale et al. |
| 8,173,107 B2 | 5/2012 | Rabinowitz et al. |
| 8,235,037 B2 | 8/2012 | Hale et al. |
| 8,288,372 B2 | 10/2012 | Hale et al. |
| 8,333,197 B2 | 12/2012 | Cross et al. |
| 8,387,612 B2 | 3/2013 | Damani et al. |
| 8,425,704 B2 | 4/2013 | Currano |
| 8,506,935 B2 | 8/2013 | Hale et al. |
| 8,684,980 B2 | 4/2014 | Hunter |
| 8,955,512 B2 | 2/2015 | Hale et al. |
| 8,991,387 B2 | 3/2015 | Damani et al. |
| 9,211,382 B2 | 12/2015 | Hale et al. |
| 9,308,208 B2 | 4/2016 | Wensley et al. |
| 9,370,629 B2 | 6/2016 | Damani et al. |
| 9,439,907 B2 | 9/2016 | Hale et al. |
| 9,440,034 B2 | 9/2016 | Hale et al. |
| 9,687,487 B2 | 6/2017 | Hodges et al. |
| 9,724,341 B2 | 8/2017 | Myers et al. |
| 9,763,476 B2 | 9/2017 | Flick |
| 10,166,224 B2 | 1/2019 | Myers et al. |
| 10,179,215 B2 * | 1/2019 | Raichman ............ A61K 36/185 |
| 10,350,157 B2 | 7/2019 | Hale et al. |
| 10,625,033 B2 | 4/2020 | Wensley et al. |
| 10,786,635 B2 | 9/2020 | Sharma et al. |
| 11,642,473 B2 | 3/2023 | Wensley |
| 2001/0020147 A1 | 9/2001 | Staniforth |
| 2001/0039262 A1 | 11/2001 | Venkataraman |
| 2001/0042546 A1 | 11/2001 | Umeda |
| 2002/0031480 A1 | 3/2002 | Peart |
| 2002/0037828 A1 | 3/2002 | Wilson |
| 2002/0058009 A1 | 5/2002 | Bartus |
| 2002/0061281 A1 | 5/2002 | Osbakken |
| 2002/0078955 A1 | 6/2002 | Nichols |

(56) References Cited

U.S. PATENT DOCUMENTS

| | | |
|---|---|---|
| 2002/0086852 A1 | 7/2002 | Cantor |
| 2002/0097139 A1 | 7/2002 | Gerber |
| 2002/0112723 A1 | 8/2002 | Schuster |
| 2002/0117175 A1 | 8/2002 | Kottayil |
| 2002/0176841 A1 | 11/2002 | Barker |
| 2003/0004142 A1 | 1/2003 | Prior |
| 2003/0015196 A1 | 1/2003 | Hodges |
| 2003/0015197 A1* | 1/2003 | Hale ................ A61M 15/0028 128/200.14 |
| 2003/0032638 A1 | 2/2003 | Kim et al. |
| 2003/0033055 A1 | 2/2003 | McRae |
| 2003/0049025 A1 | 3/2003 | Neumann |
| 2003/0051728 A1 | 3/2003 | Lloyd et al. |
| 2003/0062042 A1 | 4/2003 | Wensley |
| 2003/0106551 A1 | 6/2003 | Sprinkel |
| 2003/0118512 A1 | 6/2003 | Shen |
| 2003/0121906 A1 | 7/2003 | Abbott |
| 2003/0131843 A1 | 7/2003 | Lu |
| 2003/0132219 A1 | 7/2003 | Cox |
| 2003/0138508 A1 | 7/2003 | Novack et al. |
| 2003/0156829 A1 | 8/2003 | Cox |
| 2003/0209240 A1 | 11/2003 | Hale |
| 2004/0009128 A1 | 1/2004 | Rabinowitz |
| 2004/0016427 A1 | 1/2004 | Byron |
| 2004/0035409 A1 | 2/2004 | Harwig |
| 2004/0055504 A1 | 3/2004 | Lee |
| 2004/0081624 A1 | 4/2004 | Nguyen |
| 2004/0096402 A1 | 5/2004 | Hodges et al. |
| 2004/0099266 A1 | 5/2004 | Cross |
| 2004/0099269 A1 | 5/2004 | Hale |
| 2004/0101481 A1 | 5/2004 | Hale et al. |
| 2004/0102434 A1 | 5/2004 | Hale |
| 2004/0105818 A1 | 6/2004 | Every et al. |
| 2004/0105819 A1 | 6/2004 | Hale |
| 2004/0170571 A1 | 9/2004 | Rabinowitz et al. |
| 2004/0191322 A1 | 9/2004 | Hansson |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0016550 A1* | 1/2005 | Katase .................... A24F 40/50 131/194 |
| 2005/0034723 A1 | 2/2005 | Bennett et al. |
| 2005/0037506 A1 | 2/2005 | Hale et al. |
| 2005/0051165 A1 | 3/2005 | Cole |
| 2005/0066681 A1 | 3/2005 | Chang |
| 2005/0079166 A1 | 4/2005 | Damani et al. |
| 2005/0121024 A1 | 6/2005 | Langford |
| 2005/0126562 A1 | 6/2005 | Rabinowitz et al. |
| 2005/0131739 A1 | 6/2005 | Rabinowitz et al. |
| 2005/0133025 A1* | 6/2005 | Laiho ................ A61M 15/0045 128/200.23 |
| 2005/0268911 A1 | 12/2005 | Cross |
| 2006/0032496 A1 | 2/2006 | Hale et al. |
| 2006/0032501 A1 | 2/2006 | Hale |
| 2006/0120962 A1 | 6/2006 | Rabinowitz et al. |
| 2006/0193788 A1 | 8/2006 | Hale et al. |
| 2006/0216243 A1 | 9/2006 | Rabinowitz |
| 2006/0216244 A1 | 9/2006 | Rabinowitz |
| 2006/0233717 A1 | 10/2006 | Hale |
| 2006/0233719 A1 | 10/2006 | Rabinowitz |
| 2006/0239936 A1 | 10/2006 | Rabinowitz |
| 2006/0246011 A1 | 11/2006 | Rabinowitz |
| 2006/0246012 A1 | 11/2006 | Rabinowitz |
| 2006/0257328 A1 | 11/2006 | Rabinowitz |
| 2006/0257329 A1 | 11/2006 | Rabinowitz et al. |
| 2006/0269486 A1 | 11/2006 | Rabinowitz |
| 2006/0269487 A1 | 11/2006 | Rabinowitz |
| 2006/0280692 A1 | 12/2006 | Rabinowitz |
| 2006/0286043 A1 | 12/2006 | Rabinowitz |
| 2007/0014737 A1 | 1/2007 | Rabinowitz |
| 2007/0028916 A1 | 2/2007 | Hale |
| 2007/0031340 A1 | 2/2007 | Hale |
| 2007/0122353 A1 | 5/2007 | Hale et al. |
| 2007/0140982 A1 | 6/2007 | Every |
| 2007/0178052 A1 | 8/2007 | Rabinowitz |
| 2007/0286816 A1 | 12/2007 | Hale et al. |
| 2008/0038363 A1 | 2/2008 | Zaffaroni et al. |
| 2008/0110454 A1 | 5/2008 | White |
| 2008/0110872 A1 | 5/2008 | Hale |
| 2008/0175796 A1 | 7/2008 | Rabinowitz |
| 2008/0210225 A1 | 9/2008 | Geiger |
| 2008/0216828 A1 | 9/2008 | Wensley |
| 2008/0257345 A1 | 10/2008 | Snyder |
| 2008/0299048 A1 | 12/2008 | Hale et al. |
| 2008/0306285 A1 | 12/2008 | Hale et al. |
| 2008/0308096 A1 | 12/2008 | Borgschulte |
| 2008/0311176 A1 | 12/2008 | Hale |
| 2009/0062254 A1 | 3/2009 | Hale et al. |
| 2009/0071477 A1 | 3/2009 | Hale |
| 2009/0180968 A1 | 7/2009 | Hale et al. |
| 2009/0229600 A1 | 9/2009 | Hale |
| 2009/0235926 A1 | 9/2009 | Cross |
| 2009/0246147 A1 | 10/2009 | Rabinowitz |
| 2009/0258075 A1 | 10/2009 | Hale |
| 2009/0301363 A1 | 12/2009 | Damani |
| 2010/0006092 A1 | 1/2010 | Hale et al. |
| 2010/0055003 A1 | 3/2010 | Swanson |
| 2010/0055048 A1 | 3/2010 | Hale et al. |
| 2010/0065052 A1 | 3/2010 | Sharma et al. |
| 2010/0068155 A1 | 3/2010 | Lei et al. |
| 2010/0160240 A1 | 6/2010 | Gurd |
| 2010/0163020 A1 | 7/2010 | Hyde |
| 2010/0181387 A1 | 7/2010 | Zaffaroni et al. |
| 2010/0208438 A1 | 8/2010 | Kaltenbacher |
| 2010/0224638 A1 | 9/2010 | Rubner |
| 2010/0276505 A1 | 11/2010 | Smith |
| 2010/0282860 A1 | 11/2010 | Field |
| 2010/0294268 A1 | 11/2010 | Wensley et al. |
| 2010/0300433 A1 | 12/2010 | Sharma et al. |
| 2011/0233043 A1 | 9/2011 | Cross et al. |
| 2011/0240013 A1 | 10/2011 | Hale et al. |
| 2011/0240014 A1 | 10/2011 | Bennett et al. |
| 2011/0240022 A1 | 10/2011 | Hodges et al. |
| 2011/0244020 A1 | 10/2011 | Hale et al. |
| 2011/0245493 A1 | 10/2011 | Rabinowitz et al. |
| 2011/0253135 A1 | 10/2011 | Hale et al. |
| 2012/0048963 A1 | 3/2012 | Sharma et al. |
| 2012/0279068 A1 | 11/2012 | Mahefkey |
| 2013/0032139 A1 | 2/2013 | Hale et al. |
| 2013/0078307 A1 | 3/2013 | Holton |
| 2013/0156823 A1 | 6/2013 | Wu |
| 2013/0180516 A1 | 7/2013 | Damani |
| 2013/0180525 A1 | 7/2013 | Cross et al. |
| 2013/0251813 A1 | 9/2013 | Cawello |
| 2013/0276779 A1 | 10/2013 | Hale |
| 2013/0287851 A1 | 10/2013 | Shaw |
| 2014/0060525 A1 | 3/2014 | Hale et al. |
| 2014/0060532 A1 | 3/2014 | Hodges et al. |
| 2014/0066618 A1 | 3/2014 | Hale et al. |
| 2014/0072605 A1 | 3/2014 | Bennett et al. |
| 2015/0065491 A1 | 3/2015 | Cartt |
| 2015/0157635 A1 | 6/2015 | Hale et al. |
| 2015/0196060 A1 | 7/2015 | Wensley et al. |
| 2015/0250800 A1 | 9/2015 | Hale et al. |
| 2015/0265783 A1 | 9/2015 | Damani et al. |
| 2015/0282527 A1* | 10/2015 | Henry, Jr. ................ G01F 1/28 131/328 |
| 2016/0143364 A1 | 5/2016 | DePiano et al. |
| 2016/0166564 A1 | 6/2016 | Myers et al. |
| 2016/0310692 A1* | 10/2016 | Drew .................. A61M 11/041 |
| 2016/0324845 A1 | 11/2016 | Myers et al. |
| 2016/0374937 A1 | 12/2016 | Hale et al. |
| 2017/0049974 A1 | 2/2017 | Wensley et al. |
| 2017/0105246 A1 | 4/2017 | Cross et al. |
| 2017/0181223 A1* | 6/2017 | Sur ...................... H05B 3/0014 |
| 2017/0281884 A1 | 10/2017 | Hodges et al. |
| 2018/0014575 A1* | 1/2018 | Fursa .................... A24F 40/40 |
| 2018/0021328 A1 | 1/2018 | Myers et al. |
| 2018/0126098 A1 | 5/2018 | Sharma et al. |
| 2019/0021987 A1 | 1/2019 | Sharma |
| 2019/0082736 A1* | 3/2019 | Sur ........................ A24F 40/51 |
| 2019/0098935 A1* | 4/2019 | Phan ...................... C03C 4/02 |
| 2019/0110517 A1* | 4/2019 | Rogers .................... A24F 1/00 |
| 2019/0117909 A1 | 4/2019 | Myers |

(56) References Cited

U.S. PATENT DOCUMENTS

| | | |
|---|---|---|
| 2019/0209546 A1 | 7/2019 | Myers |
| 2020/0246559 A1 | 8/2020 | Wensley et al. |
| 2021/0008300 A1 | 1/2021 | Sharma et al. |
| 2021/0046259 A1 | 2/2021 | Hasegawa et al. |
| 2021/0052830 A1 | 2/2021 | Myers et al. |

FOREIGN PATENT DOCUMENTS

| | | |
|---|---|---|
| CN | 1082365 | 2/1994 |
| CN | 1120109 A | 4/1996 |
| CN | 1176075 | 3/1998 |
| CN | 101437496 A | 5/2009 |
| CN | 107750177 A | 3/2018 |
| CN | 110267662 A | 9/2019 |
| DE | 19854007 | 5/2000 |
| EP | 0039369 | 11/1981 |
| EP | 0274431 | 7/1988 |
| EP | 0277519 | 8/1988 |
| EP | 0358114 | 3/1990 |
| EP | 0430559 | 6/1991 |
| EP | 0492485 | 7/1992 |
| EP | 0606486 | 7/1994 |
| EP | 0734719 | 2/1996 |
| EP | 0967214 | 12/1999 |
| EP | 1080720 | 3/2001 |
| EP | 1177793 | 2/2002 |
| EP | 1222938 | 7/2002 |
| EP | 0808635 B1 | 7/2003 |
| EP | 1578422 B1 | 6/2007 |
| EP | 3268072 | 1/2018 |
| EP | 3551189 | 10/2019 |
| FR | 921852 A | 5/1947 |
| FR | 2428068 A | 1/1980 |
| GB | 502761 | 1/1938 |
| GB | 903866 | 8/1962 |
| GB | 1366041 | 9/1974 |
| GB | 2108390 | 5/1983 |
| GB | 2122903 | 1/1984 |
| HU | 200105 B | 4/1990 |
| HU | 219392 B | 6/1996 |
| JP | 2574120 | 6/1998 |
| JP | 2004-149447 | 5/2004 |
| JP | 2004-281600 | 10/2004 |
| JP | 2004-531555 | 10/2004 |
| JP | 2006-511566 | 4/2006 |
| JP | 2006-523486 | 10/2006 |
| JP | 2008-519766 | 6/2008 |
| JP | 2008-519768 | 6/2008 |
| JP | 2008-530134 | 8/2008 |
| JP | 2010-525354 | 7/2010 |
| JP | 2011-515184 A | 5/2011 |
| JP | 2018-510703 | 4/2018 |
| JP | 6773675 | 10/2020 |
| JP | 2021-511893 | 5/2021 |
| KR | 10-2217768 | 2/2021 |
| MX | 2019-006745 | 10/2019 |
| WO | WO 1985/000520 | 2/1985 |
| WO | WO 1988/008304 | 11/1988 |
| WO | WO 1990/002737 | 3/1990 |
| WO | WO 1990/007333 | 7/1990 |
| WO | WO 1991/007947 | 6/1991 |
| WO | WO 1991/018525 | 12/1991 |
| WO | WO 1992/005781 | 4/1992 |
| WO | WO 1992/015353 | 9/1992 |
| WO | WO 1992/019303 | 11/1992 |
| WO | WO 1993/011817 | 6/1993 |
| WO | WO 1993/012823 | 7/1993 |
| WO | WO 1994/009842 | 5/1994 |
| WO | WO 1994/016717 | 8/1994 |
| WO | WO 1994/016757 | 8/1994 |
| WO | WO 1994/016759 | 8/1994 |
| WO | WO 1994/017369 | 8/1994 |
| WO | WO 1994/017370 | 8/1994 |
| WO | WO 1994/027576 | 12/1994 |
| WO | WO 1994/027653 | 12/1994 |
| WO | WO 1995/031182 | 11/1995 |
| WO | WO 1996/000069 | 1/1996 |
| WO | WO 1996/000070 | 1/1996 |
| WO | WO 1996/000071 | 1/1996 |
| WO | WO 1996/009846 | 4/1996 |
| WO | WO 1996/010663 | 4/1996 |
| WO | WO 1996/013161 | 5/1996 |
| WO | WO 1996/013290 | 5/1996 |
| WO | WO 1996/013291 | 5/1996 |
| WO | WO 1996/013292 | 5/1996 |
| WO | WO 1996/030068 | 10/1996 |
| WO | WO 1996/031198 | 10/1996 |
| WO | WO 1996/037198 | 11/1996 |
| WO | WO 1997/016181 | 5/1997 |
| WO | WO 1997/017948 | 5/1997 |
| WO | WO 1997/023221 | 7/1997 |
| WO | WO 1997/027804 | 8/1997 |
| WO | WO 1997/031691 | 9/1997 |
| WO | WO 1997/035562 | 10/1997 |
| WO | WO 1997/035582 | 10/1997 |
| WO | WO 1997/036574 | 10/1997 |
| WO | WO 1997/040819 | 11/1997 |
| WO | WO 1997/049690 | 12/1997 |
| WO | WO 1998/002186 | 1/1998 |
| WO | WO 1998/016205 | 4/1998 |
| WO | WO 1998/022170 | 5/1998 |
| WO | WO 1998/029110 | 7/1998 |
| WO | WO 1998/031346 | 7/1998 |
| WO | WO 1998/034595 | 8/1998 |
| WO | WO 1998/036651 | 8/1998 |
| WO | WO 1998/037896 | 9/1998 |
| WO | WO 1999/004797 | 2/1999 |
| WO | WO 1999/011311 | 3/1999 |
| WO | WO 1999/016419 | 4/1999 |
| WO | WO 1999/024433 | 5/1999 |
| WO | WO 1999/037347 | 7/1999 |
| WO | WO 1999/037625 | 7/1999 |
| WO | WO 1999/044664 | 9/1999 |
| WO | WO 1999/055362 | 11/1999 |
| WO | WO 1999/059710 | 11/1999 |
| WO | WO 1999/064094 | 12/1999 |
| WO | WO 2000/000176 | 1/2000 |
| WO | WO 2000/000215 | 1/2000 |
| WO | WO 2000/000244 | 1/2000 |
| WO | WO 2000/019991 | 4/2000 |
| WO | WO 2000/027359 | 5/2000 |
| WO | WO 2000/027363 | 5/2000 |
| WO | WO 2000/028844 | 5/2000 |
| WO | WO 2000/028979 | 5/2000 |
| WO | WO 2000/029053 | 5/2000 |
| WO | WO 2000/029167 | 5/2000 |
| WO | WO 2000/035417 | 6/2000 |
| WO | WO 2000/038618 | 7/2000 |
| WO | WO 2000/044350 | 8/2000 |
| WO | WO 2000/044730 | 8/2000 |
| WO | WO 2000/047203 | 8/2000 |
| WO | WO 2000/051491 | 9/2000 |
| WO | WO 2000/064940 | 11/2000 |
| WO | WO 2000/066084 | 11/2000 |
| WO | WO 2000/066106 | 11/2000 |
| WO | WO 2000/066206 | 11/2000 |
| WO | WO 2000/072827 | 12/2000 |
| WO | WO 2000/076673 | 12/2000 |
| WO | WO 2001/005459 | 1/2001 |
| WO | WO 2001/013957 | 3/2001 |
| WO | WO 2001/017568 | 3/2001 |
| WO | WO 2001/019528 | 3/2001 |
| WO | WO 2001/029011 | 4/2001 |
| WO | WO 2001/032144 | 5/2001 |
| WO | WO 2001/041732 | 6/2001 |
| WO | WO 2001/043801 | 6/2001 |
| WO | WO 2001/069136 | 9/2001 |
| WO | WO 2001/080829 | 11/2001 |
| WO | WO 2001/095903 | 12/2001 |
| WO | WO 2002/000198 | 1/2002 |
| WO | WO 2002/024158 | 3/2002 |
| WO | WO 2002/051466 | 7/2002 |
| WO | WO 2002/051469 | 7/2002 |
| WO | WO 2002/056866 | 7/2002 |

(56) References Cited

FOREIGN PATENT DOCUMENTS

| | | |
|---|---|---|
| WO | WO 2002/083119 | 10/2002 |
| WO | WO 2002/094218 | 11/2002 |
| WO | WO 2002/094232 | 11/2002 |
| WO | WO 2002/094234 | 11/2002 |
| WO | WO 2002/094236 | 11/2002 |
| WO | WO 2002/094242 | 11/2002 |
| WO | WO 2002/098389 | 12/2002 |
| WO | WO 2002/098496 | 12/2002 |
| WO | WO 2002/102297 | 12/2002 |
| WO | WO 2003/024456 | 3/2003 |
| WO | WO 2003/037412 | 5/2003 |
| WO | WO 2003/045484 | 6/2003 |
| WO | WO 2003/049535 | 6/2003 |
| WO | WO-2017189883 A1 * 11/2017 .......... A61M 11/042 |
| WO | WO 2018/107045 | 6/2018 |

OTHER PUBLICATIONS

Office Action mailed Aug. 21, 2023 with respect to Canadian App No. 3,090,277 7 pages.
Alexza Pharmaceuticals (2015) "AZ-002 (Staccato alprazolam) in epilepsy patients", Dec. 21, 2015, p. 1-8.
Office Action dated Dec. 13, 2022 with respect to Japanese App No. 2020-541904 (w/English Translation), 7 pages.
Office Action mailed Aug. 16, 2023 with respect to U.S. Appl. No. 15/388,881.
U.S. Appl. No. 13/311,660, filed Dec. 6, 2011, Bennett et al.
U.S. Appl. No. 13/597,865, filed Aug. 29, 2012, Bennett et al.
International Preliminary report on Patentability for PCT/US2019/016398, dated Aug. 4, 2020, 8 pages.
International Search Report and Written Opinion for PCT/US2019/016398, dated Apr. 30, 2019, 14 pages.
U.S. Appl. No. 11/687,466, filed Mar. 16, 2007, Zaffaroni.
U.S. Appl. No. 11/964,630, filed Dec. 26, 2007, Hale.
U.S. Appl. No. 12/111,188, filed Apr. 28, 2008, Hale.
U.S. Appl. No. 12/117,737, filed May 8, 2008, Hale.
U.S. Appl. No. 12/211,247, filed Sep. 16, 2008, Sharma.
U.S. Appl. No. 12/211,554, filed Sep. 16, 2008, Sharma.
U.S. Appl. No. 12/211,628, filed Sep. 16, 2008, Lei.
U.S. Appl. No. 12/245,184, filed Oct. 3, 2008, Hale.
U.S. Appl. No. 12/275,836, filed Nov. 21, 2008, Hale.
U.S. Appl. No. 13/217,385, filed Aug. 25, 2011, Sharma.
U.S. Appl. No. 13/569,006, filed Aug. 7, 2012, Hale.
U.S. Appl. No. 15/262,954, filed Sep. 12, 2016, Hale.
U.S. Appl. No. 15/289,772, filed Oct. 10, 2016, Wensley.
AK Steel (2007) 304/304L Stainless Steel Data Sheet.
AK Steel (2007) 316/316L Stainless Steel Data Sheet.
Alexza Pharmaceuticals (2015) "AZ-002 (Staccato alprazolam) in epilepsy patients", Dec. 21, 2015, p. 1-6.
Anderson (1982) Drug Metabolism Reviews 13(5):799-826 "Recent Advances in Methodology and Concepts for Characterizing Inhalation Pharmacokinetic Parameters in Animals and Man".
Anonymous, (Jun. 1998) Guidance for Industry: Stability testing of drug substances and products, U.S. Department of Health and Human Services, FDA, CDER, CBER, pp. 1-110.
Banhart (2001) Progress in Materials Science, 46:559-632 "Manufacture, characterization and application of cellular metals and metal foams".
Bennett et al. (1981) Annual Surg. 195(6):700-705 "Patient-Controlled Analgesia: A New Concept of Postoperative Pain Relief".
Benowitz (1994) NIDA Research Monography, 2 pages, "Individual Differences in Nicotine Kinetics and Metabolism in Humans".
Bickes and Grubelich (1996) "SCB Ignitioin of Pyrotechnics, thermites, and intermetallics". Explosive Components Department, Sandia National Laboratories. Aug. 20, 1996.
BP: Chemicalsactivities (1999) Product: (Barex) Barrier Resins; Database [Online]; 8 pages; Availabe Web Site: www.bp.com/chemicals/products/product.asp; Last update: Apr. 25, 2016; Accessed on: Aug. 2, 2001.

Brand et al. (Jun. 2000) Journal of Pharmaceutical Sciences 89(6):724-731 "Total Deposition of Therapeutic Particles During Spontaneous and Controlled Inhalations".
Campbell et al. (2001) BMJ 323:1-6 "Are cannabinoids an effective and safe treatment option in the management of pain? A qualitative systemic review".
Carroll et al. (1990) Psychopharmacology (Berl) 102:443-450 "Cocaine-Base Smoking in Rhesus Monkey: Reinforcing and Physiological Effects".
Cichewicz et al. (May 1999) Journal of Pharmacology and Experimental Therapeutics 289(2):859-867, "Enhancement of mu opioid antinociception by oral DELTA 9—tetrahydrocannabinol: Dose response analysis and receptor identification".
Clark and Byron (1986) Z. Erkrank 166:13-24 "Dependence of Pulmonary Absorption Kinetics on Aerosol Particle Size".
Centerwatch.com (2000) Drugs Approved by the FDA—Drug Name: Nicotrol Inhaler; 2 pages; Available Web Site: www.centerwatch.com/patient/drugs/dru202.html; Accessed on: Aug. 2, 2001.
Cleveland Clinic (2010) Article on types and symptoms of epileptic seizure, Dec. 30, 2010.
Communication pursuant to Article 94(3) EPC from European App No. 08754883.0, dated Jun. 4, 2014, 6 pages.
Communication pursuant to Article 94(3) EPC from European App No. 16762425.3, dated Oct. 23, 2019, 8 pages.
Communication pursuant to Article 94(3) EPC from European App No. 16762425.3, dated Dec. 3, 2020, 6 pages.
Dallas et al. (1983) Developments in the Science and Practice of Toxicology, pp. 419-422, "A Small Animal Model for Direct Respiratory and Hemodynamic Measurements in Toxicokinetic Studies of Volatile Chemicals," Hayes, A. W. et al. eds., Elsevier Science Publishers, New York.
Darquenne et al. (1997) American Physiological Society 83(3):966-974, "Aerosol Dispersion in Human Lung: Comparison Between Numerical Simulations and Experiments for Bolus Tests".
Database Biosis "Online!" Biosciences Information Service, Philadelphia, PA 1979, Knight, V. et al., "Amantadine aerosol in humans", database accession No. PREV 198069035552 abstract &Antimicrobial Agents and Chemotherapy 16(5):572-578.
Database WPI, Section CH, Week 198941, Derwent Publications Ltd., London, GB; Class B07, AN 1989-297792 AP002230849 & JP 01 221313 (Nippon Create 1(K), Sep. 4, 1989, abstract.
Davies et al. (1972) Journal of Applied Physiology 32(5):591-600, "Breathing of Half-Micron Aerosols".
Dershwitz et al. (2000) Anesthesiology 93(3): 619-628 "Pharmacokinetics and Pharmacodynamics of Inhaled versus Intravenous Morphine in Healthy Volunteers".
Examination Report for Canadian App No. 2,979,213, dated Jun. 22, 2018, 7 pages.
Examination Report (First) for New Zealand App No. 735414, dated Mar. 19, 2018, 7 pages.
Examination Report (Further) for New Zealand App No. 735414, dated Nov. 6, 2018, 3 pages.
Extended European Search Report for Application No. 17878604.2, dated Jun. 22, 2020, 10 pages.
Faris et al. (2002) International Journal of Cardiology 82:149-158 "Current evidence supporting the role of diuretics in heart failure: a meta analysis of randomized controlled trials".
Feynman et al. (1964) The Feyman Lectures on Physics: Mainly Electromagnetism and Matter "Chapter 32: Refractive Index of Dense Materials" Addison-Wesley: Publishing Company, Inc., Reading, Massachusetts, pp. 32-1-32-13.
Finlay (2001) "The Mechanics of Inhaled Pharmaceutical Aerosols", Academic Press: San Diego Formula 2.39. pp. 3-14 (Table of Contents). pp. v-viii.
French et al. (2015) Epilepsy and Behavior 46:34-50 "The epilepsy foundation's 4th biennial epilepsy pipeline update conference".
Gleeson et al. (1982) Psychopharmacology 78:141-146 "Chlorpromazine Hyperalgesia Antagonizes Clonidine Analgesia, but Enhances Morphine Analgesia in Rats Tested in a Hot-Water Tail-Flick Paradigm".
Gonda (1991) "Particle Deposition in the Human Respiratory Tract," Chapter 176, The Lung: Scientific Foundations. Crystal R.G.and West, J.B. (eds.), Raven Publishers, New York. pp. 2289-2294.

(56) References Cited

OTHER PUBLICATIONS

Graves et al. (1983) Annals of Internal Medicine 99:360-366 "Patient-Controlled Analgesia".
Hamon et al. (1987) Neuropharmacology 26(6):531-539 "Opioid Receptors and Neuropeptides in the CNS in Rats Treated Chronically with Amoxapine and Amitriptyline".
Hatsukami et al. (May 1990) Pharmacology Biochemistry & Behavior 36:1-7 "A Method for Delivery of Precise Doses of Smoked Cocaine-Base to Human".
Heyder et al. (1986) J. Aerosol Sci. 17(5):811-822 "Deposition of Particles in the Human Respiratory Tract in the Size Range 0.005-15 μm".
Huizer (1987) Pharmaceutisch Weekblad Scientific Edition 9(4):203-211 "Analytical Studies on Illicit Heron. V. Efficacy of Volitization During Heroin Smoking".
Hurt and Robertson (1998) JAMA 280(13):1173-1181 "Prying Open the Door to the Tobacco Industry's Secrets About Nicotine: The Minnesota Tobacco Trial".
Hwang (1999) Wall Street Journal, Jun. 28, 1999, pp. 1-3 "Tobacco: R. J. Reynolds Hopes to Spin Nicotine Into Drugs".
International Preliminary Report on Patentability from PCT/US2008/056452 dated Sep. 15, 2009.
International Search Report and Written Opinion for PCT/US2008/056452 dated Jan. 22, 2009.
International Search Report and Written Opinion for PCT/US2014/046288 dated Oct. 2, 2014, 9 pages.
International Preliminary Report on Patentability for PCT/US2016/021554, dated Sep. 12, 2017, 7 pages.
International Search Report and Written Opinion for PCT/US2016/021554, dated May 27, 2016.
International Preliminary Report on Patentability for PCT/US2017/065347, dated Jun. 11, 2019.
International Search Report and Written Opinion for PCT/US2017/065347, dated Feb. 22, 2018.
James et al. (1991) Radiation Protection Dosimetry 38(1/3):159-165 "The Respiratory Tract Deposition Model Proposed by the ICRP Task Group".
Kexun XU (1989) "Handbook of Organic Chemical Material and Intermediates," Dec. 31, 1989, pp. 490-491 (English relevance is Office Action mailed Jan. 30, 2018 with respect to Chinese App. No. 201480050267X w/English Translation).
Kim and Patel (1994) Tet. Letters 35:5603-5606 "'BOP' As a Reagent for Mild and Efficient Preparation of Esters".
Lichtman et al. (1996) Journal of Pharmacology and Experimental Therapeutics 279:69-76 "Inhalation Exposure to Volatilized Opioids Produces Antinociception in Mice".
Lichtman et al. (2000) European Journal of Pharmacology 399:141-149 "Pharmacological Evaluation of Aerosolized Cannabinoids in Mice".
Lopez (Jul. 26, 1999) "UK Researcher Develops Nicotinic Drugs with R. J. Reynolds", 1 page; Available Web Site: www.eurekalert.org/pub_releases/1999-07/UoKM-Urdn-260799.php; Last Update: Mar. 16, 2002; Accessed on: Oct. 1, 2002.
Lynch (2001) J. Psychiatry Neuroscience 26:30-36 "Antidepressants as analgesics: a review of randomized controlled trials".
Magnusson et al. (2000) Brain Research 855:260-266 "The Involvement of Dopamine in Nociception: the role of D1 and D2 Receptors in the Dorsolateral Striatum".
Martin and Lue (May/Jun. 1989) Journal of Analytical Toxicology 13:158-162 "Pyrolysis and Volatilization of Cocaine".
Mattox and Carroll (1996) Psychopharmacology 125:195-201 "Smoked Heroin Self-Administration in Rhesus Monkeys".
McCormick et al. (1988) British Journal of Anesthesia 80(4):564-565 "Bronchospasm During Inhalation of Nebulized Midazolam".
McGee et al. (1979) American Journal of Hospital Pharmacy 36:633-640 "Phenotiazine Analgesia—Fact or Fantasy?".
Meng et al. (1997) NIDA Research Monogragh 173:201-224 "Inhalation Studies with Drugs of Abuse".
Meng et al. (1999) Drug and Alcohol Dependence 53:111-120 "Pharmacological effects of methamphetamine and other stimulants via inhalation exposure".
NS Healthcare (2014) (hllps://www.ns-healthcare.com/analysis/elegant-simplicity-single-dose-disposable-inhalers-4214657/) Jul. 4, 2014.
Office Action mailed Mar. 24, 2017 with respect to Canadian App No. 2,918,145, 4 pages.
Office Action mailed Jun. 22, 2018 with respect to Canadian App No. 2,979,213, 7 pages.
Office Action mailed Feb. 3, 2020 with respect to Canadian App No. 2,979,213, 5 pages.
Office Action mailed Jul. 8, 2020 with respect to Canadian App No. 3,046,385, 6 pages.
Office Action mailed Jan. 30, 2018 with respect to Chinese App No. 201480050267.X (w/English Translation).
Office Action mailed Nov. 29, 2019 with respect to Chinese App No. 201680027355.7 (wEnglish Translation), 15 pages.
Office Action mailed Apr. 15, 2021 with respect to Chinese App No. 201680027355.7 (wEnglish Translation).
Office Action mailed Mar. 26, 2018 with respect to Japanese App No. 2016-525796 (w/English Translation).
Office Action mailed Oct. 29, 2018 with respect to Japanese App No. 2017-548052 (w/English Translation).
Office Action mailed Sep. 20, 2019 with respect to Japanese App No. 2017-548052 (w/English Translation), 6 pages.
Office Action mailed Jul. 7, 2020 with respect to Japanese App No. 2019-531043 (w/English Translation) 12 pages.
Office Action mailed Feb. 2, 2021 with respect to Japanese App No. 2019-531043 (w/English Translation).
Office Action mailed Jan. 26, 2007 with respect to U.S. Appl. No. 10/057,198.
Office Action mailed Jul. 3, 2006 with respect to U.S. Appl. No. 10/057,198.
Office Action mailed Sep. 20, 2005 with respect to U.S. Appl. No. 10/057,198.
Office Action mailed Dec. 4, 2003 with respect to U.S. Appl. No. 10/057,198.
Office Action mailed Jun. 5, 2007 with respect to U.S. Appl. No. 10/057,197.
Office Action mailed Sep. 21, 2006 with respect to U.S. Appl. No. 10/057,197.
Office Action mailed Jan. 12, 2005 with respect to U.S. Appl. No. 10/057,197.
Office Action mailed Jun. 3, 2004 with respect to U.S. Appl. No. 10/057,197.
Office Action mailed Dec. 15, 2003 with respect to U.S. Appl. No. 10/057,197.
Office Action mailed Dec. 28, 2007 with respect to U.S. Appl. No. 10/146,080.
Office Action mailed Mar. 20, 2007 with respect to U.S. Appl. No. 10/146,080.
Office Action mailed Jun. 5, 2006 with respect to U.S. Appl. No. 10/146,080.
Office Action mailed Aug. 25, 2005 with respect to U.S. Appl. No. 10/146,080.
Office Action mailed Feb. 27, 2004 with respect to U.S. Appl. No. 10/146,080.
Office Action mailed Oct. 30, 2007 with respect to U.S. Appl. No. 10/146,086.
Office Action mailed Feb. 12, 2007 with respect to U.S. Appl. No. 10/146,086.
Office Action mailed Dec. 13, 2005 with respect to U.S. Appl. No. 10/146,086.
Office Action mailed Nov. 21, 2007 with respect to U.S. Appl. No. 10/146,088.
Office Action mailed Sep. 28, 2007 with respect to U.S. Appl. No. 10/146,088.
Office Action mailed Feb. 16, 2007 with respect to U.S. Appl. No. 10/146,088.
Office Action mailed Aug. 13, 2003 with respect to U.S. Appl. No. 10/153,313.

(56) References Cited

OTHER PUBLICATIONS

Office Action mailed Mar. 8, 2005 with respect to U.S. Appl. No. 10/718,982.
Pankow et al. (1997) Environ. Sci. Technol. 31:2428-2433 "Conversion of Nicotine in Tobacco Smoke to Its Volatile and Available Free-Base Form through the Action of Gaseous Ammonia".
Pankow (2000) ACS Conference—San Francisco—Mar. 26, 2000, pp. 1-8 "Chemistry of Tobacco Smoke".
Pfeiffer (1982) Geriatrics 37(2):67-76 "Drugs for pain in the elderly".
Poochikian and Bertha (2000) Resp. Drug Deliv. VII: 109-115 "Inhalation Drug Product Excipient Controls: Significance and Pitfalls".
Rapoport and Sheftell (1997) CNS Drugs 7(1):37-46 "Intranasal Medications for the Treatment of Migraine and Cluster Headache".
Reticulated Vitreous Carbon (1997) Flyer for ERG Materials and Aerospace Corp.
Schreiber et al. (1999) Pharmacology Biochemistry and Behavior 64(1):75-80 "The Atypical Neuroleptics Clozapine and Olanzapine Differ Regarding Their Antinociceptive Mechanisms and Potency".
ScienceDaily Magazine (Jul. 1999) "University of Kentucky Researcher Develops Nicotinic Drugs with R. J. Reynolds"; 2 pages; Availabe Web Site: www.sciencedaily.com/releases/1999/07/990728073542.htm; Last update: Mar. 14, 2002; Accessed on: Sep. 23, 2002.
Seeman et al. (1999) J. Agric. Food Chem. 47(12):5133-5145 "The Form of Nicotine in Tobacco. Thermal Transfer of Nicotine and Nicotine Acid Salts to Nicotine in the Gas Phase".
Sekine and Nakahara (1987) Journal of Forensic Science 32(5): 1271-1280 "Abuse of Smoking Methamphetamine Mixed with Tobacco: 1. Inhalation Efficiency and Pyrolysis Products of Methamphetamine".
Streitwieser and Heathcock, eds., (1981) "Introduction to Organic Chemistry" Second edition, Macmillan Publishing Co., Inc., New York, pp. ix-xvi. (Table of Contents).
Tsantilis et al. (2001) Aerosol Science and Technology 34:237-246 "Sintering Time for Silica Particle Growth".
U.S. Appl. No. 11/687,466, filed Mar. 16, 2007, Zaffaroni et al.
U.S. Appl. No. 12/211,247, filed Sep. 16, 2008, Sharma et al.
U.S. Appl. No. 12/211,554, filed Sep. 16, 2008, Sharma et al.
U.S. Appl. No. 12/211,628, filed Sep. 16, 2008, Lei et al.
U.S. Appl. No. 12/352,582, filed Jan. 12, 2009, Hale et al.
U.S. Appl. No. 12/413,339, filed Mar. 27, 2009, Rabinowitz et al.
U.S. Appl. No. 12/471,070, filed May 22, 2009, Hale et al.
U.S. Appl. No. 12/485,704, filed Jun. 16, 2009, Damani et al.
U.S. Appl. No. 12/490,102, filed Jun. 23, 2009, Hale et al.
Vapotronics, Inc. (1998) "Vapotronics is creating global opportunities in the drug delivery and smoking replacement markets with an innovative digital inhaler technology platform"; Available Web Site: www.vapotronics.com.au/banner.htm; 11 pages; Accessed on: Jun. 5, 2000.
Vaughan (1990) J. Aerosol Sci. 21(3): 453-462 "The Generation of Monodisperse Fibres of Caffeine".
Ward et al. (1997) Clinical Pharmacology & Therapeutics 62(6):596-609 "Morphine Pharmacokinetics after Pulmonary Administration from a Novel Aerosol Delivery System".
Williams (Feb. 8, 1999) "Rhone-Poulenc Rorer Inc. and Targacept Inc. Announce Alliance to Develop New Drugs to Treat Alzheimer's and Parkinson's Diseases"; 1 page; Available Web Site: www.rpr.rpna.com/ABOUT_RPR/pressrels/1999/990209-targa.html; Last update: Oct. 11, 1999; Accessed on: Jan. 28, 2000.
Wilson, et al. (1979) Proceedings of the Society for Experimental Bioloy and Medicine 161(3):350-354, Biosis Database Accession No. PREV198069008137, "Amatadine Aerosol Particle Aerosol Generation and Delivery to Man".
Wood et al. (1996) Pharmacology Biochemistry & Behavior 53(1):57-66 "Methylecgonidine Coats the Crack Particle".
Wood et al. (1996) Pharmacology Biochemistry & Behavior 55(2):237-248 "Generation of Stable Test Atmospheres of Cocaine Base and Its Pyrolyzate, Methylecgonidine, and Demonstration of Their Biological Activity".
Communication pursuant to Article 94(3) EPC from European App No. 19747391.1 dated Jan. 9, 2024, 5 pages.
Extended European Search Report for Application No. 19747391.1, dated Sep. 30, 2021, 8 pages.
GA Sciences Education Foundation (2002) p. 30-31 "Oxidation Resistant Materials".
Le (2004) Acta Materialia 52:911-920 "Surface Oxide Fracture in Cold Aluminum Rolling".
Office Action dated Aug. 7, 2023 with respect to Japanese App No. 2020-541904 (w/English Translation), 5 pages.
Office Action mailed Oct. 16, 2023 with respect to Korean App No. 10-2020-7024744 (w/English Translation), 21 pages.
Office Action mailed Apr. 17, 2023 with respect to U.S. Appl. No. 16/044,224.
Office Action Mailed Dec. 7, 2023 with respect to U.S. Appl. No. 16/966,785.

* cited by examiner

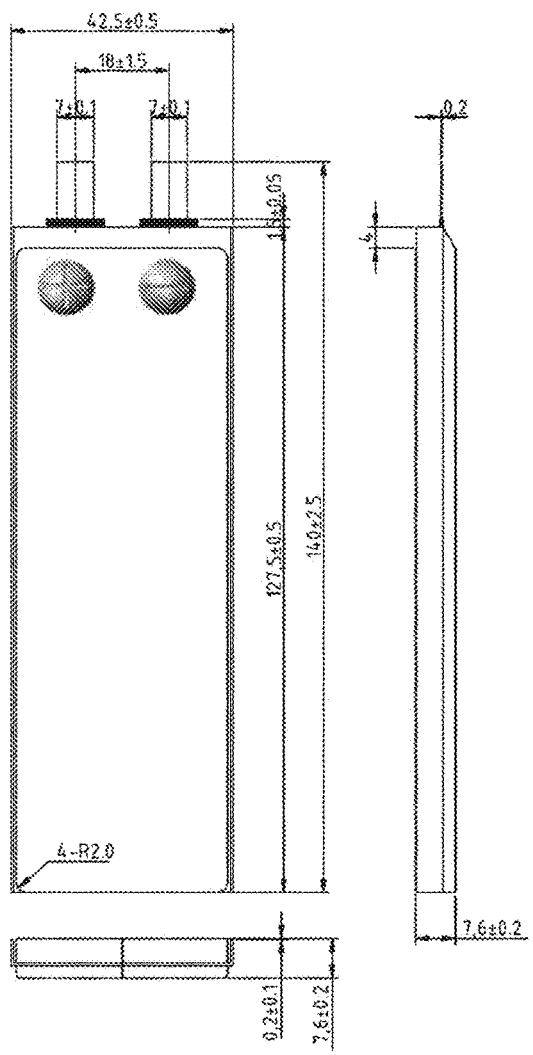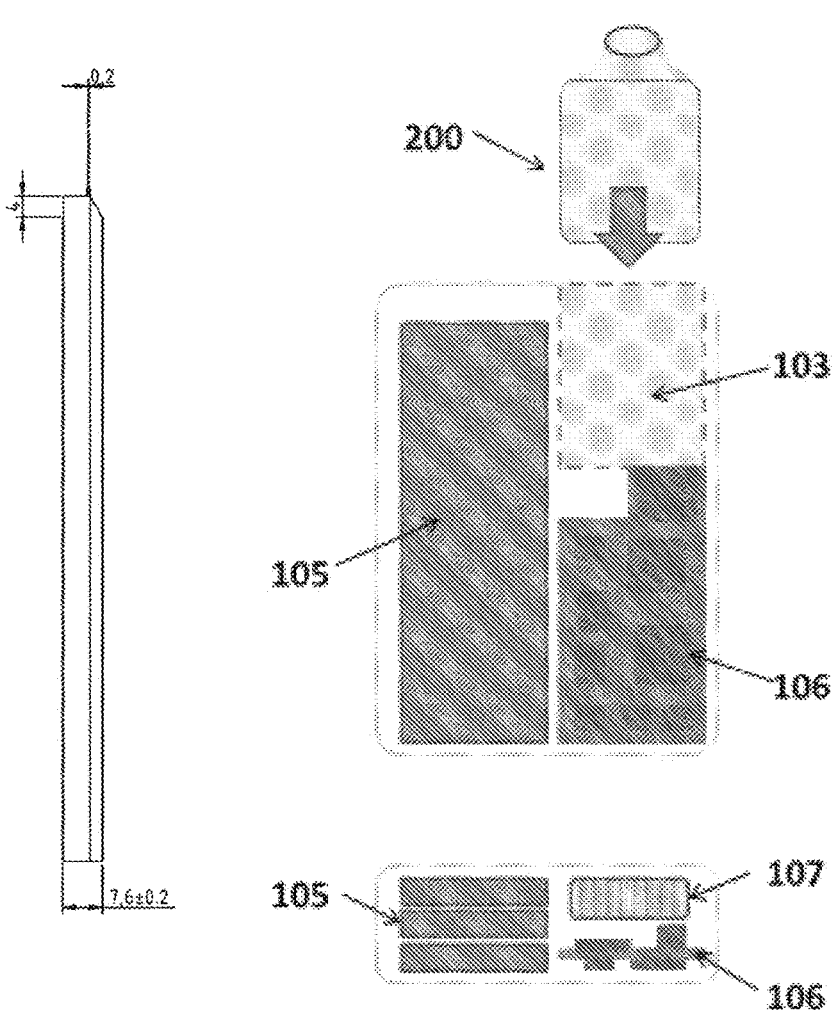
FIG. 22
FIG. 23

ELECTRICAL CONDENSATION AEROSOL DEVICE

CROSS-REFERENCE TO RELATED APPLICATION

This application is a continuation of U.S. application Ser. No. 16/966,785, filed on Jul. 31, 2020, entitled "ELECTRICAL CONDENSATION AEROSOL DEVICE", which application claims priority to and is a 35 U.S.C. § 371 national phase application of PCT/US19/16398 (WO2019/152873), filed on Feb. 1, 2019, entitled "ELECTRICAL CONDENSATION AEROSOL DEVICE", which application claims priority to and the benefit of U.S. Provisional Application Nos. 62/625,757, filed Feb. 2, 2018 entitled "ELECTRICAL CONDENSATION AEROSOL DEVICE" and U.S. Provisional Application No. 62/626,388, filed Feb. 5, 2018, entitled "LASER WELDING DISSIMILAR METALS TO CREATE AN ELECTRICAL RESISTANCE CIRCUIT FOR A CONDENSATION AEROSOL DEVICE", and U.S. Provisional Application No. 62/626,396, filed Feb. 5, 2018, entitled "HANDHELD, MULTIDOSE, ELECTRICALLY HEATED, CONDENSATION AEROSOL DEVICE". The entire disclosures of which are incorporated herein by reference in their entirety.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

TECHNICAL FIELD

The present disclosure relates generally to the field of drug aerosols and methods for delivery of aerosols and kits for delivering drug aerosols. More specifically, the invention relates to a device that generates a condensation drug aerosol via electrical heating of a foil substrate which is coated with the drug where the drug itself is vaporized. The drug may be sensitive to degradation during the vaporization process which may be temperature dependent. The drug purity, emitted dose, particle size and stability as an aerosol is benefited through the electrical condensation drug aerosol device described herein.

BACKGROUND

Currently, there are a number of approved devices for the inhalation delivery of drugs, including dry powder inhalers, nebulizers, and pressurized metered dose inhalers. Rapid vaporization of thin films of drugs at temperatures up to 600° C. in less than 500 ms in an air flow can produce drug aerosols having high yield and high purity with minimal degradation of the drug. Condensation drug aerosols can be used for effective pulmonary delivery of drugs using inhalation medical devices. Devices and methods in which thin films of drugs deposited on metal substrates are vaporized by electrically resistive heating have been demonstrated.

The development of inhalable drug formulations, especially formulations for systemic delivery by inhalation is desirable as it enables a minimally invasive, efficient and rapid route of administration. Inhalation aerosols from dry powder inhalers, nebulizers, and pressurized metered dose inhalers typically include excipients or solvents to increase stability or deliverability of these drugs in an aerosol form. These typical inhalation devices do not adequately control the emitted dose, particle size and fine respirable fraction of the drug aerosols generated. As a result, aerosols generated from these types of devices are inefficient for systemic drug delivery via the pulmonary route.

The present disclosure overcomes the foregoing discussed disadvantages and problems encountered with other inhalation technologies and provides a mechanism to control degradation, including thermal degradation, during drug vaporization, making it possible to produce aerosols with a high level of purity of drug compounds with respirable aerosol particle size, consistent fine respirable fraction and emitted dose ideally suited for systemic drug delivery by inhalation.

Use of batteries to power handheld devices has proved problematic. Traditional battery types intended for use in portable handheld devices include alkaline, nickel cadmium (Ni—Cd) and nickel metal hydride (NiMH). These battery chemistries are suitable for applications where the electrical current draw requirement is low, such as when the amount of drug to be vaporized is small (less than 200 micrograms) and thus requiring a relatively small foil substrate surface area to heat. However, when the drug load on the foil substrate is larger, such as in the 0.5 mg to 10 mg range, significantly greater power is required. For these larger drug loads, traditional battery chemistries are not capable of delivering the high current needed to rapidly heat the foil substrate for efficient vaporization of a drug film. In addition, some of these battery chemistries are susceptible to a memory effect and lose capacity after repeated charging and discharging cycles.

One method of achieving a high discharge current needed for rapidly heating a foil substrate is to use supercapacitors. However, supercapacitors capable of delivering the high current needed for larger drug loads are relatively large for a handheld drug delivery device; about 4 to 6 supercapacitors, each of which are about the size of C or D size batteries are required to deliver the necessary power. In addition, a separate power source is required to charge the supercapacitors making the device less portable.

It is desirable to provide a handheld condensation aerosol drug delivery device wherein compact batteries capable of high power output provide the power necessary to rapidly heat a foil substrate to vaporize a drug. The provision of such a device is an object of the present invention.

It is desirable to provide a device wherein dissimilar metals are joined together to form an electrical circuit wherein one component of the circuit is comprised of a foil substrate which is coated with a drug. Driving electrical current through the circuit yields uniform electrical resistance, thus heating of the foil substrate which vaporizes the drug coated on the foil substrate that subsequently condenses to form aerosol particles for efficient drug delivery via inhalation. The provision of such a device is an object of the present invention.

SUMMARY OF THE EMBODIMENTS

The present invention provides a drug delivery article comprising: an electrically conductive foil substrate; a drug composition comprising the drug coated on a defined portion of the surface of the substrate, wherein the coated drug film has a defined thickness which may be uniform or applied with an intentional thickness gradient; an electrical current delivery device to drive a precise electrical current profile through the substrate to affect electrical resistive heating at a rate that achieves a precise temperature profile sufficient to vaporize all or a portion of the coated drug composition within a period of three seconds or less; and an airway which directs inhalation air over the surface of the substrate to entrain and condense the vaporized drug composition into condensation aerosol particles which exit the mouthpiece end of the airway into the user's mouth to reach the deep lung via the airway passages to effect systemic drug delivery. The aerosol drug composition comprises a therapeutically effective amount of the drug. The drug film has a thickness between 0.01 and 50 μm. The drug film has a thickness between 0.01 and 20 μm. The drug selected may be sensitive to temperatures associated with the vaporization process. The drug selected may be sensitive to degradation associated with the vaporization process. The drug selected may benefit by the use of a heating device described herein wherein the heating provides a rapid, consistent and reproducible heating profile. The benefits may include improved drug purity, diminished degradation and increased deposition into the deep part of the lungs (alveoli).

In one embodiment, the drug delivery device comprises the mapping of the drug coating area on the substrate by using thermal images of the substrate surface captured during electrical resistance heating to identify the regions of the substrate which, in the presence of a varying range of air flow rates, develop the target surface temperatures that are optimal for vaporization of the coated drug substance. In one embodiment, numerical modeling tools such as computational fluid dynamics (CFD) analysis to model fluid flow and heat transfer is used to predict the surface temperature gradients of the substrate during electrical resistance heating in the presence of a varying range of air flow rates to identify the regions of the substrate that are optimal for vaporization of the coated drug substance in order to map specific areas of the substrate for drug coating. In one embodiment, the drug delivery device comprises the drug coated on specific regions comprising the upstream edge to mid-point of the foil substrate (FIG. 14). In one embodiment, the drug delivery device comprises the drug coated in specific regions comprising the mid-point to downstream edge of the foil substrate (FIG. 13). The drug coating area may be in various configurations including, but not limited to a trapezoidal shape (FIG. 15), a crescent shape, a rectangular shape or a square shape. The drug is coated in specific regions of the substrate where the substrate temperature is optimal for vaporization and avoids regions of the substrate where the substrate temperature may be too hot which may cause generation of impurities during vaporization or where the substrate temperature may be too low which may cause dissociation of the drug into undesired constituent parts and/or reduced emitted dose. The shape of the drug coating area may follow a temperature map of the substrate during heating to allow for coating of the drug in reference to the regions of the substrate where the temperature profile is optimal for vaporization of the drug substance during heating of the substrate.

In one embodiment, the disclosure teaches a method of treating a condition where rapid delivery of a drug is optimal for treatment wherein the above described device is used with a drug. The drug may be a vaporization temperature and/or degradation sensitive drug.

In one embodiment, the disclosure teaches a method of treating a condition where rapid delivery of a drug is optimal for treatment wherein the above described device is used with a vaporization temperature and/or degradation sensitive drug. In one embodiment, the disclosure teaches a method of treating a condition where rapid delivery of a drug is optimal for treatment wherein the above described device is used for the drug delivery of small molecules, wherein the molecular weight is less than 600 g/mol. In one embodiment, the disclosure teaches a method of treating a condition where rapid delivery of a drug is optimal for treatment wherein the above described device is used for the drug delivery of small molecules, wherein the molecular weight is less than 500 g/mol. In one embodiment, the disclosure teaches a method of treating a condition where rapid delivery of a drug is optimal for treatment wherein the above described device is used for the drug delivery of small molecules, wherein the molecular weight is less than 400 g/mol. In one embodiment, the disclosure teaches a method of treating a condition where rapid delivery of a drug is optimal for treatment wherein the above described device is used for the drug delivery of small molecules, wherein the molecular weight is less than 300 g/mol.

In one embodiment, the disclosure teaches a method of treating a condition in a patient, said method comprising: (a) providing a device for producing a condensation aerosol with vaporization temperature sensitive drugs or drugs sensitive to degradation, comprising an electrically resistive heating element comprising a metal foil substrate configured to vaporize a drug substance disposed thereon, wherein the drug is coated on the substrate in such a way to enhance the efficiency of heating of the drug and minimize degradation of the drug during vaporization; a controller that delivers electrical current following a precise, controlled electrical current delivery profile to the foil substrate, thereby effecting a rapid, yet controlled temperature rise in the foil substrate causing the drug substance coated on the substrate to vaporize and a means for condensing the vaporized substance to produce a condensation aerosol which has a controlled particle size distribution; and (b) administering the drug to the subject through inhalation to the alveolar region of the lung. This method can be used to treat conditions including Parkinson's disease (including an off episode related to Parkinson's Disease), Movement Disorders (Restless Legs Syndrome, Dystonia, Chorea, Huntington's Disease, Ataxia, Tremor-Essential Tremor, Tics, Gait, Stiff Person Syndrome, Myoclonus and Startle), Cyclic Vomiting Syndrome, Treatment Resistant Depression, Sleep Disorders (e.g. Middle of the Night Insomnia), Breakthrough Pain, Pulmonary arterial hypertension, Migraine, Smoking Cessation, Pain management, nausea, seizures, Dyspnea with congestive heart failure, Alzheimer's disease, Erectile Dysfunction, Gout, Hyperkinetic Disorders, Weight management (e.g. obesity, binge eating), Addiction Abuse (e.g. smoking, alcohol, narcotics), Central Nervous System Disorders, Urinary Tract Disorders, Vertigo, Diabetes, Respiratory Diseases, Osteoporosis, Measles, Antibiotics, Anxiety, Analgesia, Agitation, and any condition wherein it is advantageous for rapid delivery of the drug into the circulatory system.

In one embodiment, the disclosure teaches a method for treating a condition in a subject in need thereof, the method comprising administering a drug by inhalation, wherein the drug is a vaporization temperature sensitive drug and wherein the drug is administered in the form of a condensation aerosol. In one embodiment, at least 80% by weight of the drug aerosol particles have a size less than 5 micron. In one embodiment, at least 90% by weight of the drug aerosol particles have a size less than 5 micron. In one embodiment, at least 93% by weight of the drug aerosol particles have a size less than 5 micron. In one embodiment, at least 95% by weight of the drug aerosol particles have a size less than 5 micron. In one embodiment, at least 97% by weight of the drug aerosol particles have a size less than 5 micron. In one embodiment, at least 99% by weight of the drug aerosol particles have a size less than 5 micron. In one embodiment, the condensation aerosol particles are characterized by less than 15% drug degradation products. In one embodiment, the condensation aerosol particles are characterized by less than 10% drug degradation products. In one embodiment, the condensation aerosol particles are characterized by less than 9% drug degradation products. In one embodiment, the condensation aerosol particles are characterized by less than 8% drug degradation products. In one embodiment, the condensation aerosol particles are characterized by less than 7% drug degradation products. In one embodiment, the condensation aerosol particles are characterized by less than 6% drug degradation products. In one embodiment, the condensation aerosol particles are characterized by less than 5% drug degradation products. In one embodiment, the condensation aerosol particles are characterized by less than 4% drug degradation products. In one embodiment, the condensation aerosol particles are characterized by less than 3% drug degradation products. In one embodiment, the condensation aerosol particles are characterized by less than 2% drug degradation products. In one embodiment, the condensation aerosol particles are characterized by less than 1% drug degradation products.

In one embodiment, the disclosure teaches a composition for delivery of a drug comprising a device which has a precise amount of drug coated on a foil substrate, wherein the device has a means to drive a precise electrical current profile through the substrate to affect electrical resistive heating at a rate that achieves a precise temperature profile sufficient to vaporize all or a portion of the coated drug composition, a condensation aerosol a) formed by volatilizing a drug composition under conditions effective to produce a heated vapor of said drug composition and condensing the heated vapor of the drug composition to form condensation aerosol particles, b) wherein said condensation aerosol particles are characterized by less than 10% drug degradation products, c) wherein the aerosol MMAD is less than 5 μm, and d) wherein the drug is sensitive to degradation. In one embodiment the aerosol MMAD is less than 3.5 μm. In one embodiment, a portion of the drug coated that is vaporized is at least 99.5% of the drug. In one embodiment, a portion of the drug coated that is vaporized is at least 99% of the drug. In one embodiment, a portion of the drug coated that is vaporized is at least 95% of the drug. In one embodiment, a portion of the drug coated that is vaporized is at least 90% of the drug. In one embodiment, a portion of the drug coated that is vaporized is at least 85% of the drug. In one embodiment, a portion of the drug coated that is vaporized is at least 80% of the drug. In one embodiment, a portion of the drug coated that is vaporized is at least 75% of the drug. In one embodiment, a portion of the drug coated that is vaporized is at least 70% of the drug. In one embodiment, a portion of the drug coated that is vaporized is at least 65% of the drug. In one embodiment, a portion of the drug coated that is vaporized is at least 60% of the drug. In one embodiment, a portion of the drug coated that is vaporized is at least 55% of the drug. In one embodiment, a portion of the drug coated that is vaporized is at least 50% of the drug. In one embodiment, a portion of the drug coated that is vaporized is at least 45% of the drug. In one embodiment, a portion of the drug coated that is vaporized is at least 40% of the drug. In one embodiment, a portion of the drug coated that is vaporized is at least 35% of the drug. In one embodiment, a portion of the drug coated that is vaporized is at least 30% of the drug. In one embodiment, a portion of the drug coated that is vaporized is at least 25% of the drug. In one embodiment, a portion of the drug coated that is vaporized is at least 20% of the drug. In one embodiment, a portion of the drug coated that is vaporized is at least 15% of the drug. In one embodiment, a portion of the drug coated that is vaporized is at least 10% of the drug.

The condensation aerosols of the various embodiments are typically formed by preparing a film containing a drug composition of a desired thickness on a heat-conductive and impermeable substrate and heating said substrate to vaporize said film, and cooling said vapor thereby producing aerosol particles containing said drug composition. Rapid heating in combination with the gas flow helps reduce the amount of decomposition. Thus, a heat source is used that typically heats the substrate to a temperature greater than 200° C., preferably at least 250° C., more preferably at least 300° C. or 350° C. and produces substantially complete volatilization of the drug composition from the substrate within a period of 3 seconds, preferably, within 1 second, and more preferably, within 0.5 seconds. Optimal temperature ranges for vaporization of drugs are dependent on the physical characteristics of the specific drug being vaporized. Typically, the air flow rate over the vaporizing compound is between about 4 and 80 L/minute.

The film thickness in any of the embodiments of this invention is such that an aerosol formed by vaporizing the compound by heating the substrate and condensing the vaporized compound contains 10% by weight or less drug-degradation product. The use of thin films allows a more rapid rate of vaporization and hence, generally, less thermal drug degradation. Typically, the film has a thickness between 0.01 and 50 μm or between 0.01 and 20 μm. In some variations, the film has a thickness between 0.01 and 15 μm. In some variations, the film has a thickness between 0.01 and 10 μm. In some variations, the film has a thickness between 0.01 and 5 μm. In some variations, the film has a thickness between 4 and 10 μm. In some variations, the film has a thickness between 5 and 10 μm. In some variations, the film has a thickness between 3 and 9 μm. The selected area of the substrate surface expanse and film thickness is such as to yield an effective human therapeutic dose of the drug aerosol. In some variations the thickness of the drug is determined by thermal mapping.

During the condensation stage the MMAD of the aerosol is increasing over time. Typically, in variations of the invention, the MMAD increases within the size range of 0.01-3 μm as the vapor condenses as it cools by contact with the carrier gas then further increases as the aerosol particles collide with each other and coagulate into larger particles. Most typically, the MMAD grows from <0.5 μm to >1 μm in less than 1 second. Thus typically, immediately after condensing into particles, the condensation aerosol MMAD doubles at least once per second, often at least 2, 4, 8, or 20 times per second. In other variations, the MMAD increases within the size range of 0.1 to 3 μm. In some variations, the carrier gas is air. In some variations, other gases or a combination of various gases may be used.

Various modifications and additions can be made to the embodiments discussed without departing from the scope of the invention. For example, while the embodiments described above refer to particular features, the scope of this invention also included embodiments having different combination of features and embodiments that do not include all of the above described features.

Accordingly, one aspect of the present disclosure teaches a handheld aerosol drug delivery device comprising: an electrically conductive substrate; a drug layer capable of vaporization upon being heated to a target temperature coated on the exterior surface of the substrate; an electrical circuit to control and direct electrical current in a precise delivery profile at a precise voltage; a means to sense the start of inhalation by a subject and utilize the signal triggered by the inhalation to initiate heating of the substrate; and a power supply comprising lithium polymer batteries.

One aspect of the present disclosure provides the handheld drug supply unit wherein the lithium polymer batteries have current output capabilities greater than 40 to 50 amps.

One aspect of the present disclosure provides for the size of the handheld drug supply unit is less than six inches in height and width.

One aspect of the present disclosure provides that three batteries connected in series are used in the device to generate at least 10 V.

One aspect of the present disclosure provides that the batteries are custom designed to fit within the handheld device, given size and shape limitations.

The device for forming a drug aerosol comprises an element configured to heat the composition to form a vapor, an element allowing the vapor to condense to form a condensation aerosol, and an element permitting a user to inhale the condensation aerosol. The element configured to heat the composition comprises a heat-conductive substrate and formed on the substrate is typically a drug composition film containing an effective dose of drug when the drug is administered in an aerosol form. An electrical power source is available to drive electrical resistance heating of the substrate to produce a substrate temperature, typically that is greater than 300° C., to substantially volatilize the drug composition film from the substrate in a period of 2 seconds or less, more preferably, in a period of 500 milliseconds or less. The electrical power source is in the form of lithium batteries capable of delivering power of up to 400 to 700 W. The device may further comprise features such as breath-actuation, lockout elements, dose counting/logging or anti-tampering methods.

In yet another aspect, the disclosure teaches kits for delivering drug aerosol comprising a thin film of a drug composition and a device for dispensing said film as a condensation aerosol. Typically, the film thickness is between 0.5 and 30 μm. The film can comprise pharmaceutically acceptable excipients and is typically heated at a rate so as to substantially volatilize the film in 500 milliseconds or less. In other embodiments, the drug film is heated at a rate so as to substantially volatize the film in 1000 milliseconds or less.

Accordingly, one aspect of the present disclosure teaches use of laser welding to attach two dissimilar metals for the purpose of creating an electrical resistance circuit, where one metal is copper and the other metal is stainless steel, where the stainless steel is coated with a drug which is vaporized, where the vapor then condenses to form an aerosol which has particles suitable to delivery to the deep lung, where the particles are entrained in air flow through an airway, where the airflow is the result of inhalation by the subject.

One aspect of the present disclosure provides the laser welding yielding a stainless steel foil substrate to copper wherein the heating of the substrate is uniform once the drug delivery device is activated.

One aspect of the present disclosure provides an electrical resistance circuit for a condensation aerosol device, wherein laser welding is used to weld two dissimilar metals in the electrical resistance circuit.

One aspect of the present disclosure provides a that the two dissimilar metals in the electrical resistance circuit are copper and stainless steel.

One aspect of the disclosure provides a handheld medical device suitable to generate a drug condensation aerosol by thermal vaporization of a drug comprising: one or more air inlets, one or more air outlets, one or more batteries to provide electric current, one or more connectors to electrically connect the device to a disposable cartridge comprising a drug composition coated on a foil substrate, and one or more electrical current delivery devices to control the release of electric current to the disposable cartridge, wherein: said air inlets and air outlets define an airway; at least one of the air outlets is configured as a housing to attach said disposable cartridge; said electrical current delivery devices are configured to drive a precise electrical current profile to the foil substrate of the disposable cartridge to affect electrical resistive heating at a rate that achieves a precise temperature profile with a controllable ramp-up to a target temperature and heating rate, and the temperature profile is suitable to vaporize a therapeutically effective amount of the drug composition coated on the fil substrate of the cartridge within a period of 3 seconds or less followed by condensation inside the cartridge of the resulting vapor to form drug aerosol particles. The ramp-up target temperature is between 150 and 550° C.; 250 and 450° C.; 200 and 500° C.; 300 and 450° C.; or 340 and 440° C. The ramp-up time is between 50 and 200 ms; 50 and 80 ms; or 50 and 115 ms. The foil substrate is heated at 3 to 10° C./ms or 4 to 10° C./ms. The heating rate is selected from one or more of plateau heating, tampered cooling and progressive heating. This heating rate can be selected once the ramp-up temperature is achieved. The batteries are able to provide a peak electric current higher than; 30 A and a voltage of 8-13 V; or 100 A and a voltage of 9-12 V. In one embodiment, the batteries are lithium polymer batteries. The device may comprise a means for detecting the inhalation of the user. In one embodiment, a flow switch, flow sensor or a temperature sensor is used to detect inhalation. In one embodiment, a flow switch, flow sensor or a temperature sensor is used to as a breath actuator. In one embodiment, the device comprises a device enclosure. In one embodiment, the interior walls of the device enclosure comprise antistatic material. In one embodiment, the housing of the device comprises antistatic material. The antistatic material may be coated on the housing of the airway. The device may have a means for detecting or verifying the correct attachment of the disposable cartridge into the housing of the device. The verification of the correct attachment can be made through verification of electrical contact, a proximity sensor, a mechanical or optical switch. In one embodiment, the device has determinants to control orientation. One embodiment includes a symmetrical cartridge to determine orientation.

In one embodiment, the device comprises a means for uniquely recognizing the disposable cartridge. The recognition of the disposable cartridge includes the following: RFID, bar code or, QR code, read/write chip or combinations thereof. The device may comprise a means for controlling the temperature of the foil substrate in the disposable cartridge by sensing the temperature and feeding the foil substrate temperature information to the electrical current delivery device to modify the electric current delivery in order to achieve the required temperature; through the measurement of electrical resistance across the foil substrate, including taking an optical measurement. Control of the temperature of the foil substrate in the disposable cartridge may comprise direct contact measurement with a thermocouple.

The disposable cartridge may comprise an identification (ID). The device may store the cartridge ID after it is inserted into the device to determine the status (used or unused) of the cartridge. Other features may include: lockout timer: timer to limit frequency of dosing; dosing reminder: device to remind patient to take drug; dose log: capture time and date each time dose is taken; Device Access Security: biometric or other method to restrict access to device operation; Battery charge indicator; Bluetooth connectivity: device paired to mobile device. Signal sent when dose is taken. A mobile device application can be set up to alert others (physician, family members, care taker, etc.) a dose has been taken.

The device may comprise a pneumatic sealing interface between the air outlet of the device and the air inlet of the cartridge.

In one embodiment, the disclosure teaches a disposable cartridge comprising: a chamber, one or more air inlets connected to the chamber, one or more air outlets connected to the chamber, at least one of the air outlets is adapted as a mouthpiece, an airway defined by the air inlets, the chamber and the air outlets, a foil substrate having an impermeable surface with or without perforations, means for holding a foil substrate in the chamber, a drug composition coated on at least a portion of the foil substrate in the form of a film having a thickness between 0.01 and 50 µm, one or more connectors to electrically connect the disposable cartridge to a handheld medical device, means for condensing a vaporized drug within the chamber to produce condensation aerosol particles, which are entrained in the airflow through the airway and flow through the mouthpiece; wherein at least one air inlet is adapted to be attached to the handheld medical device; the foil substrate is an electrically conductive foil substrate and has means to receive electricity from the handheld medical device to achieve a precise temperature profile with a controllable ramp-up to a target temperature and heating rate in order to vaporize a therapeutically effective amount of the drug composition followed by condensation inside the cartridge of the resulting vapor to form aerosol particles. The foil substrate may be positioned substantially parallel to the airway. The foil substrate may be a metal foil substrate. The foil substrate may be a stainless steel foil substrate.

The composition comprising a drug has a thickness between 0.01 and 20 microns. In one embodiment, the foil substrate and the connectors are electrically connected through a connection circuit to define an electrical resistance circuit wherein the connection circuit and the foil substrate are made of the same or different metals. In one embodiment, the foil substrate and the connection circuit are made of different metals; one metal is copper and the other metal is stainless steel. In one embodiment, one metal is nickel and one is stainless steel. Other combinations of metals include gold and stainless steel, brass and stainless steel, and aluminum and stainless steel.

In one embodiment, the foil substrate and the connection circuit are laser welded, joined together by crimping or clamping. In one embodiment, the connection circuit is a printed circuit board or flex circuit. In one embodiment, the foil substrate and the connection circuit results in uniform heating of the foil substrate. In one embodiment, the drug composition coated on at least a portion of the foil substrate exhibits different film thicknesses at different areas of the coating. The drug composition coated on at least a portion of the foil substrate can be applied in different shapes including trapezoidal or crescent, and can be applied in different regions of the foil substrate including the geometric center of the shape applied is closer to the upstream edge than to the downstream edge of the foil substrate or the geometric center of the shape applied is closer to the downstream edge than to the upstream edge of the foil substrate.

In one embodiment, the disclosure teaches a method for delivery of a drug with a handheld device. In one embodiment, the disclosure teaches a method of treatment for a patient with the handheld device. In one embodiment, the disclosure teaches a kit comprising a handheld delivery device including instructions for use.

In one embodiment, the disclosure teaches the drug corresponding to a specific condition. For instance, when the drug is loxapine the disease, condition or episode is agitation, including: rapidly control mild to moderate agitation in adults with schizophrenia or bipolar disorder, or acute treatment of agitation associated with schizophrenia or bipolar I disorder in adults. Treating with benzodiazepines such as alprazolam or estazolam, wherein the disease, condition or episode is treatment of seizures, including epileptic seizures. When the drug is fentanyl, the disease, condition or episode is breakthrough pain; when the drug is zaleplon or almorexant, the disease, condition or episode is sleep disorders including: middle of the night awakening, or middle of the night insomnia; when the drug is apomorphine, pergolide, pramipexole or ropinirole, the disease, condition or episode is Parkinson's disease (including off-episodes in Parkinson's disease) and restless leg syndrome; when the drug is granisetron, ondansetron or palonosetron, the disease, condition or episode is: nausea, vomiting or cyclic vomiting syndrome; or when the drug is nicotine or nicotine meta-salicylate, the disease, condition or episode is treatment of nicotine craving and/or effecting cessation of smoking.

In one embodiment, the drug is a free base. In one embodiment, the drug is a salt.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIG. 18 shows an example of a drug that can withstand a large range of vaporization temperatures.

FIG. 19 shows an example of a drug that is sensitive to vaporization temperature.

FIG. 22 shows a commercially available lithium polymer battery suitable for use in a portable handheld condensation aerosol drug delivery device.

FIG. 23 shows a portable, handheld, battery operated, electrically heated, condensation aerosol drug delivery device concept layout.

DETAILED DESCRIPTION

Figure 1:
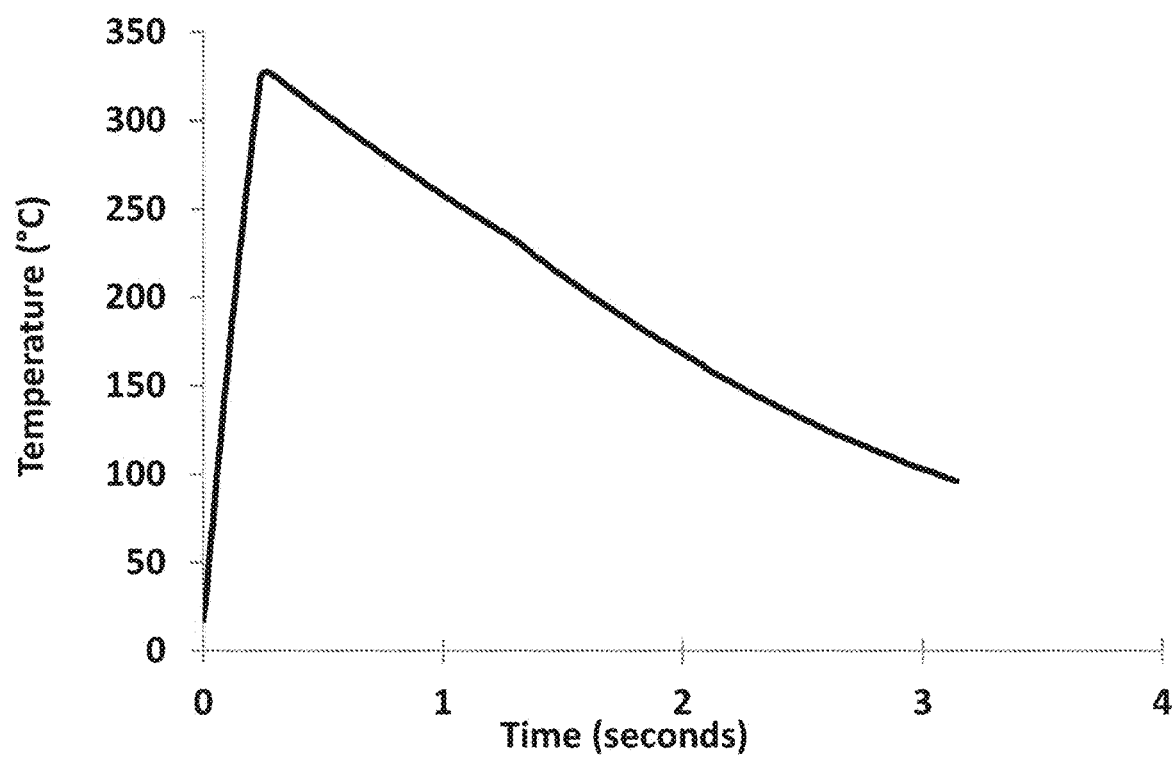
FIG. 1 shows an initial ramp-up heating temperature versus time chart.

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described and claimed herein, and while various features are ascribed to different embodiments, it should be appreciated that the features described with respect to one embodiment may be incorporated with other embodiments as well. By the same token, however, no single feature or features of any described or claimed embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Embodiment 1

A handheld medical device (100) suitable to generate a drug condensation aerosol by thermal vaporization of a drug comprising:
 a) one or more air inlets (107);
 b) one or more air outlets (103);
 c) one or more batteries (105) to provide electric current;
 d) one or more connectors to electrically connect the device (100) to a disposable cartridge (200) comprising a drug composition (210) coated on a foil substrate (209); and
 e) one or more electrical current delivery devices (106) to control the release of electric current to the disposable cartridge (200);
wherein:
 said air inlets (107) and air outlets (103) define an airway;
 at least one of the air outlets (103) is configured as a housing to attach said disposable cartridge (200);
 said electrical current delivery devices (106) are configured to drive a precise electrical current profile to the foil substrate (209) of the disposable cartridge (200) to affect electrical resistive heating at a rate that achieves a precise temperature profile with a controllable ramp-up to a target temperature and heating rate; and
 the temperature profile is suitable to vaporize a therapeutically effective amount of the drug composition (210) coated on the foil substrate (209) of the cartridge (200) within a period of 3 seconds or less followed by condensation inside the cartridge of the resulting vapor to form drug aerosol particles.

Embodiment 2

The device of the previous embodiment, wherein said ramp-up target temperature is between 150 and 550° C. or between 250 and 450° C.

Embodiment 3

The device of the previous embodiment, wherein said ramp-up target temperature is between 200 and 500° C.

Embodiment 4

The device of the previous embodiment, wherein said ramp-up target temperature is between 300 and 450° C. or between 250 and 450° C.

Embodiment 5

The device of any of the previous embodiments, wherein the ramp-up time is between 50 and 200 ms.

Embodiment 6

The device of any of the previous embodiment, wherein the ramp-up time is between 50 and 115 ms or between 50 and 80 ms.

Embodiment 7

The device of any of the previous embodiments, wherein the foil substrate (209) is heated at 3 to 10° C./ms in the ramp-up time or at 4 to 10° C. in the ramp-up time.

Embodiment 8

The device of any of the previous embodiments, wherein said heating rate is selected from one or more of plateau heating, tampered cooling and progressive heating.

Embodiment 9

The device of any of the previous embodiments, wherein the batteries (105) are able to provide a peak electric current higher than 30 A and a voltage of 8-13 V.

Embodiment 10

The device of the previous embodiment, wherein the batteries (105) are able to provide a peak electric current higher than 100 A and a voltage of 9-12 V.

Embodiment 11

The device of any of the previous embodiments, wherein the batteries (105) are lithium polymer batteries.

Embodiment 12

The device of any of the previous embodiments, which further comprises means for detecting the inhalation of the user.

Embodiment 13

The device of embodiment 12, wherein said means for detecting the inhalation of the user comprise a flow sensor.

Embodiment 14

The device of embodiment 12, wherein said means for detecting the inhalation of the user comprise a flow switch.

Embodiment 15

The device of embodiment 12, wherein said means for detecting the inhalation of the user comprise a temperature sensor.

Embodiment 16

The device of any of the previous embodiments, which further comprises a device enclosure (108).

Embodiment 17

The device of the previous embodiment, wherein the interior walls of the device enclosure (108) comprise antistatic material.

Embodiment 18

The device of any of the previous embodiments, which further comprises means for verifying the correct attachment (103A) of the disposable cartridge (200) into the housing of the device (103).

Embodiment 19

The device of embodiment 18, wherein the means for verifying the correct attachment (103A) of the disposable cartridge (200) into the housing of the device (103) comprise verification of electrical contact.

Embodiment 20

The device of embodiment 18, wherein the means for verifying the correct attachment (103A) of the disposable cartridge (200) into the housing of the device (103) comprise a proximity sensor.

Embodiment 21

The device of embodiment 18, wherein the means for verifying the correct attachment (103A) of the disposable cartridge (200) into the housing of the device (103) comprise a mechanical or optical switch.

Embodiment 22

The device of any of the previous embodiments, which further comprises means for uniquely recognizing the disposable cartridge (200).

Embodiment 23

The device of embodiment 22, wherein the means for uniquely recognizing the disposable cartridge (200) are selected from RFID tag, bar code. QR code, read/write chip or combinations thereof.

Embodiment 24

The device of any of the previous embodiments, which further comprises means for controlling the temperature of the foil substrate (209) in the disposable cartridge (200) by sensing the temperature of the foil substrate (209) and feeding the foil substrate temperature information to the electrical current delivery device (106) to modify the electric current delivery in order to achieve the required temperature.

Embodiment 25

The device of embodiment 24, wherein the means for controlling the temperature of the foil substrate (0.209) in the disposable cartridge (200) comprise the measurement of electrical resistance across the foil substrate.

Embodiment 26

The device of embodiment 24, wherein the means for controlling the temperature of the foil substrate (209) in the disposable cartridge (200) comprise optical measurement.

Embodiment 27

The device of embodiment 24, wherein the means for controlling the temperature of the foil substrate (209) in the disposable cartridge (200) comprise direct contact measurement with a thermocouple.

Embodiment 28

The device of any of the previous embodiments, which further comprises a pneumatic sealing interface between the air outlet (103) of the device (100) and the air inlet (220) of the cartridge (200).

Embodiment 29

A disposable cartridge (200) comprising:
a) a chamber;
b) one or more air inlets (220) connected to the chamber;
c) one or more air outlets (202) connected to the chamber,
d) an airway (203) defined by the air inlets (220), the chamber and the air outlets (202);
e) a foil substrate (209) having an impermeable surface with or without perforations;
f) means for holding a foil substrate (204) in the chamber;
g) a drug composition (210) coated on at least a portion of the foil substrate (209) in the form of a film having a thickness between 0.01 and 50 µm;
h) one or more connectors (208) to electrically connect the disposable cartridge (200) to a handheld medical device (100); and
i) means for condensing a vaporized drug within the chamber to produce condensation aerosol particles, which are entrained in the airflow through the airway (203) and flow through the mouthpiece (202);
wherein
at least one air inlet (220) is configured to be attached to the handheld medical device (100);
at least one of the air outlets (202) is configured as a mouthpiece; and
the foil substrate (209) is an electrically conductive foil substrate and has means to receive electricity from the handheld medical device (100) to achieve a precise temperature profile with a controllable ramp-up to a target temperature and heating rate in order to vaporize a therapeutically effective amount of the drug composition followed by condensation inside the cartridge of the resulting vapor to form drug aerosol particles.

Embodiment 30

The cartridge of embodiment 29, wherein the foil substrate is positioned substantially parallel to the airway (203).

Embodiment 31

The cartridge of any of embodiments 29 to 30, wherein the foil substrate (209) is a metal foil substrate.

Embodiment 32

The cartridge of any of embodiments 29 to 31, wherein the foil substrate (209) is a stainless steel foil substrate.

Embodiment 33

The cartridge of any of embodiments 29 to 32, wherein the drug composition (210) has a thickness between 0.01 and 20 µm.

Embodiment 34

The cartridge of any of embodiments 29 to 33, wherein the foil substrate (209) and the connectors (208) are electrically connected through a connection circuit to define an electrical resistance circuit wherein the connection circuit and the foil substrate are made of the same or different metals.

Embodiment 35

The cartridge of embodiment 34, wherein the foil substrate (209) and the connection circuit are made of different metals; one metal is copper and the other metal is stainless steel. In another embodiment one metal is nickel and one is stainless steel. Other combinations of metals include gold and stainless steel, brass and stainless steel, and aluminum and stainless steel.

Embodiment 36

The cartridge of embodiment 35, wherein the foil substrate (209) and the connection circuit are laser welded.

Embodiment 37

The cartridge of embodiment 35, wherein the foil substrate (209) and the connection circuit are joined together by crimping.

Embodiment 38

The cartridge of embodiment 35, wherein the foil substrate (209) and the connection circuit are joined together by clamping.

Embodiment 39

The cartridge of any of the embodiments 34 to 38, wherein the connection circuit is a printed circuit board (211) or flex circuit (204).

Embodiment 40

The cartridge of any of embodiments 34 to 39, wherein the foil substrate (209) and the connection circuit results in uniform heating of the foil substrate (209).

Embodiment 41

The cartridge of any of embodiments 29 to 40, wherein the drug composition (210) coated on at least a portion of the foil substrate (209) exhibits different film thickness at different areas of the coating.

Embodiment 42

The cartridge of any of embodiments 29 to 41, wherein the drug composition (210) coated on at least a portion of the foil substrate (209) is applied in a given shape.

Embodiment 43

The cartridge of embodiment 42, wherein the applied shape is trapezoidal.

Embodiment 44

The cartridge of embodiment 42, wherein the applied shape is crescent.

Embodiment 45

The cartridge of any of embodiments 42 to 44, wherein the geometric center of the shape is closer to the upstream edge than to the downstream edge of the foil substrate (209).

Embodiment 46

The cartridge of any of embodiments 42 to 44, wherein the geometric center of the shape is closer to the downstream edge than to the upstream edge of the foil substrate (209).

Embodiment 47

The cartridge of any of embodiments 29 to 46, wherein the drug is selected from acetaminophen, amantadine, atenolol, bromazepam, brompheniramine maleate, caffeine, celecoxib, clofazimine, clonidine, codeine, cyproheptadine, dapsone, diclofenac ethyl ester, diflunisal, fenfluramine, flumazenil, flurbiprofen, galanthamine, hydromorphone, indomethacin norcholine ester, ketorolac methyl ester, ketorolac norcholine ester, melatonin, memantine, methadone, morphine, nabumetone, naproxen, orphenadrine, phenytoin, pindolol, procainamide, propafenone, quinidine, quinine, spironolactone, thalidomide, theophylline, tramadol hydrochloride, trazodone, triamterene, ketotifen, brompheniramine, butorphanol, diazepam, estazolam, ketamine, meperidine, oxycodone, chlorpheniramine, doxylamine, ethacrynic acid, flunitrazepam, haloperidol, lidocaine, loxapine succinate, olanzapine, tacrine, trifluoperazine, amoxapine, chlorzoxazone, ibuprofen, loxapine, maprotiline, pergolide, piribedil, protriptyline HCl, tocainide, zonisamide, azatadine, chlorpheniramine maleate, cyproheptadine HCl, flecainide, isocarboxazid, ketoprofen ethyl ester, loratadine, methoxsalen, propranolol, testosterone, benztropine, clozapine, midazolam, paroxetine, sertraline, valproic acid, zaleplon, clomipramine, loperamide, mexiletine HCl, venlafaxine, amitriptyline, betahistine, naratriptan, pramipexole, sildenafil, terbutaline, vitamin E, flurazepam, metoprolol, naloxone, rizatriptan, selegiline, tadalafil, triazolam, trimipramine, bupropion HCl, doxepin, imipramine, lamotrigine, metaproterenol, metoclopramide, morphine, nortriptyline, perphenazine, quetiapine, ciclesonide, alprazolam, carbinoxamine maleate, cyclobenzaprine, disopyramide, ephedrine, granisetron, indomethacin, indomethacin ethyl ester, indomethacin methyl ester, ketoprofen methyl ester, ketorolac ethyl ester, mirtazapine, nalbuphine, nicotine, ropinirole, ropinirole fumarate, acebutolol, hydroxychloroquine, meperidine, estradiol, fenoprofen, prochlorperazine, toremifene, hydroxyzine, atropine, buprenorphine, bumetanide, fentanyl, ibutilide, pyrilamine, zolmitriptan, zotepine, chlordiazepoxide, citalopram, ketoprofen, pergolide, ropinirole HCl, rotigotine, efavirenz, zopiclone, sumatriptan, bergapten, buspirone HCl, eletriptan, nortriptyline, colchicine, flunisolide, nefazodone, rofecoxib, tranylcypromine HCl, fluoxetine, promethazine, trimipramine maleate, meclizine, diltiazem, temazepam, tolterodine, valdecoxib, apomorphine diacetate, donepezil, sotalol, tramadol, cinnarizine, isotretinoin, zolpidem, buspirone, chlorpromazine, albuterol, verapamil, naltrexone, telmisartan, hyoscyamine, tranylcypromine, esmolol, pioglitazone, treprostinil, dipyridamole, apomorphine HCl, linezolid, carbinoxamine, butorphanol tartrate, clemastine, fluconazole, tolfenamic acid, lovastatin, apomorphine HCl diacetate, promazine, sibutramine, astemizole, diphenhydramine, pyrilamine maleate, diphenhydramine HCl, fluphenazine, citalopram, triamcinolone acetonide, fluticasone propionate, buprenorphine HCl, tamoxifen, aripiprazole, frovatriptan, nefazodone, protriptyline, oxybutynin, meclizine, benazepril, ethambutol, scopolamine, nicotine salts, treprostinil salts, ondansetron, palonosetron HCl, tizanidine, almorexant or mixtures thereof. In one embodiment, the drug is a free base. In one embodiment, the drug is a salt.

Embodiment 48

The cartridge of any of embodiments 29 to 47, wherein the drug is selected from loxapine, alprazolam, estazolam, fentanyl, tizanidine, zaleplon, almorexant, apomorphine, pergolide, pramipexole, ropinirole, nicotine, granisetron, ondansetron, palonosetron, any pharmaceutically acceptable salts or mixtures thereof.

Embodiment 49

The cartridge of any of embodiments 29 to 48, wherein the drug is nicotine or nicotine meta salicylate.

Embodiment 50

The cartridge of any of embodiments 29 to 48, wherein the drug is apomorphine or apomorphine hydrochloride

Embodiment 51

The cartridge of any of embodiments 29 to 48, wherein the drug, is palonosetron or palonosetron hydrochloride.

Embodiment 52

The cartridge of any of embodiments 29 to 51, wherein the chamber comprises antistatic material on at least part of its internal walls.

Embodiment 53

The cartridge of any of embodiments 29 to 52, wherein at least 50% by weight of the drug aerosol particles generated have a particle size, defined as MMAD, of less than 5 μm.

Embodiment 54

The cartridge of any of embodiments 29 to 53, wherein at least 90% by weight of the drug aerosol particles generated have a particle size, defined as MMAD, of less than 5 μm.

Embodiment 55

The cartridge of any of embodiments 29 to 54, wherein said drug aerosol particles comprise less than 10% of drug degradation products.

Embodiment 56

The cartridge of any of embodiments 29 to 55, wherein said drug composition (210) coated on the foil substrate (209) comprises more than 90% of the drug.

Embodiment 57

The cartridge of any of embodiments 29 to 56, which further comprises means for verifying its correct attachment into the housing (103) of the handheld medical device (100).

Embodiment 58

The cartridge of embodiment 57, wherein said means for verifying its correct attachment comprise verification of electrical contact.

Embodiment 59

The cartridge of embodiment 57, wherein said means for verifying its correct attachment comprise a proximity sensor.

Embodiment 60

The cartridge of embodiment 57, wherein said means for verifying its correct attachment comprise a mechanical or optical switch.

Embodiment 61

The cartridge of any of embodiments 29 to 60, which comprises means for being uniquely recognized by the handheld medical device (100).

Embodiment 62

The cartridge of embodiment 61, wherein said means for being uniquely recognized are selected from the list consisting of RFID tag, bar code, QR code, read/write chip and combinations thereof.

Embodiment 63

The cartridge of any of embodiments 29 to 62, which comprises means for detecting the inhalation of the user.

Embodiment 64

The cartridge of embodiment 63, wherein said means for detecting inhalation comprise a flow sensor.

Embodiment 65

The cartridge of embodiment 63, wherein said means for detecting inhalation comprise a flow switch.

Embodiment 66

The cartridge of embodiment 63, wherein said means for detecting inhalation comprise a temperature sensor.

Embodiment 67

The cartridge of any of embodiments 30 to 66, which further comprises means for distributing the airflow from the air inlets (220).

Embodiment 68

The cartridge of the previous embodiment, wherein said means for distributing the airflow is a perforated bulkhead (206).

Embodiment 69

The cartridge of any of embodiments 30 to 68, which comprises a pneumatic sealing interface between the air outlet of the device (205) and the air inlet of cartridge (220).

Embodiment 70

The cartridge (200) of any of embodiments 29 to 69, wherein the handheld medical device (100) is the device of any of embodiments 1 to 28.

Embodiment 71

The device (100) of any of embodiments 1 to 28, wherein the cartridge (200) is the cartridge of any of embodiments 29 to 70.

Embodiment 72

A method of treating a condition or episode in a subject comprising:
(a) providing the disposable cartridge (200) as defined in any of embodiments 29 to 70;
(b) attaching said disposable cartridge (200) to the handheld medical device (100) as defined in any of embodiments 1 to 28 or 71; and
(c) administering the drug to the subject through inhalation for pulmonary delivery.

Embodiment 73

The method of treatment of embodiment 72, wherein:
a) when the drug is loxapine, the condition or episode is agitation, comprising:
  a. rapidly control mild to moderate agitation in adults with schizophrenia or bipolar disorder, or
  b. acute agitation associated with schizophrenia or bipolar I disorder in adults;
b) when the drug is alprazolam or estazolam, the condition or episode is epilepsy, wherein epilepsy comprises seizures;
c) when the drug is fentanyl, the condition or episode is breakthrough pain;
d) when the drug is zaleplon or almorexant, the condition or episode is a sleep disorder comprising:
  a. middle of the night awakening, or
  b. middle of the night insomnia;

e) when the drug is apomorphine, pergolide, pramipexole or ropinirole, the condition or episode is Parkinson's disease (including off-episodes in Parkinson's disease);
f) when the drug is granisetron, ondansetron or palonosetron, the condition or episode is:
  a. nausea,
  b. vomiting or
  c. cyclic vomiting syndrome; or
g) when the drug is nicotine or nicotine meta-salicylate, the condition or episode is nicotine craving and/or effecting cessation of smoking.

Embodiment 74

The device (100) of any of embodiments 1 to 28 or 71 for use in therapy.

Embodiment 75

The device for use of embodiment 74 wherein:
a) when the drug is loxapine, the condition or episode is agitation, comprising:
  a. rapidly control mild to moderate agitation in adults with schizophrenia or bipolar disorder, or
  b. acute agitation associated with schizophrenia or bipolar I disorder in adults;
b) when the drug is alprazolam or estazolam, the condition or episode is epilepsy, wherein epilepsy comprises seizures;
c) when the drug is fentanyl, the condition or episode is breakthrough pain;
d) when the drug is zaleplon or almorexant, the condition or episode is a sleep disorder comprising:
  a. middle of the night awakening, or
  b. middle of the night insomnia;
e) when the drug is apomorphine, pergolide, pramipexole or ropinirole, the condition or episode is Parkinson's disease (including off-episodes in Parkinson's disease);
f) when the drug is granisetron, ondansetron or palonosetron, the condition or episode is:
  a. nausea,
  b. vomiting or
  c. cyclic vomiting syndrome; or
g) when the drug is nicotine or nicotine meta-salicylate, the condition or episode is nicotine craving and/or effecting cessation of smoking.

Embodiment 76

The cartridge (200) of any of embodiments 29 to 70 for use in therapy.

Embodiment 77

The cartridge for use of embodiment 76 wherein:
a) when the drug is loxapine, the condition or episode is agitation, comprising:
  a. rapidly control mild to moderate agitation in adults with schizophrenia or bipolar disorder, or
  b. acute agitation associated with schizophrenia or bipolar I disorder in adults;
b) when the drug is alprazolam or estazolam, the condition or episode is epilepsy, wherein epilepsy comprises seizures;
c) when the drug is fentanyl, the condition or episode is breakthrough pain;
d) when the drug is zaleplon or almorexant, the condition or episode is a sleep disorder comprising:
  a. middle of the night awakening, or
  b. middle of the night insomnia;
e) when the drug is apomorphine, pergolide, pramipexole or ropinirole, the condition or episode is Parkinson's disease (including off-episodes in Parkinson's disease);
f) when the drug is granisetron, ondansetron or palonosetron, the condition or episode is:
  a. nausea,
  b. vomiting or
  c. cyclic vomiting syndrome; or
g) when the drug is nicotine or nicotine meta-salicylate, the condition or episode is nicotine craving and/or effecting cessation of smoking.

Embodiment 78

The cartridge (200) of any of embodiments 29 to 70 attached to the device (100) of embodiments 1 to 28 or 71 for use in therapy.

Embodiment 79

The cartridge attached to the device for use of embodiment 78 wherein:
a) when the drug is loxapine, the condition or episode is agitation, comprising:
  a. rapidly control mild to moderate agitation in adults with schizophrenia or bipolar disorder, or
  b. acute agitation associated with schizophrenia or bipolar I disorder in adults;
b) when the drug is alprazolam or estazolam, the condition or episode is epilepsy, wherein epilepsy comprises seizures;
c) when the drug is fentanyl, the condition or episode is breakthrough pain;
d) when the drug is zaleplon or almorexant, the condition or episode is a sleep disorder comprising:
  a. middle of the night awakening, or
  b. middle of the night insomnia;
e) when the drug is apomorphine, pergolide, pramipexole or ropinirole, the condition or episode is Parkinson's disease (including off-episodes in Parkinson's disease);
f) when the drug is granisetron, ondansetron or palonosetron, the condition or episode is:
  a. nausea.
  b. vomiting or
  c. cyclic vomiting syndrome; or
g) when the drug is nicotine or nicotine meta-salicylate, the condition or episode is nicotine craving and/or effecting cessation of smoking.

Embodiment 80

A kit comprising:
a) one handheld medical device (100) as defined in any of embodiments 1 to 28 or 71;
b) one or more disposable cartridge (200) as defined in any of embodiments 29 to 70; and
c) instructions to attach said disposable cartridge (200) to said handheld medical device (100) and to use them.

Embodiment 81

The kit of embodiment 80, wherein the instructions comprise any of the uses of any of embodiments 72 to 79.

Embodiment 82

A kit comprising:

a) one or more disposable cartridge (200) as defined in any of embodiments 29 to 70; and b) instructions to attach said disposable cartridge (200) to the handheld medical device (100) as defined in any of embodiments 1 to 28 or 71 and to use them.

Embodiment 83

The kit of embodiment 82, wherein the instructions comprise any of the uses of any of embodiments 72 to 79.

Embodiment 84

A kit comprising:

a) one handheld medical device (100) as defined in any of embodiments 1 to 28 or 71; and b) instructions to attach the disposable cartridge (200) as defined in any of embodiments 29 to 70 to said handheld medical device and to use them.

Embodiment 85

The kit of embodiment 84, wherein the instructions comprise any of the uses of any of embodiments 72 to 79.

FIG. 1 shows a temperature to time chart of initial ramp-up heating. The foil substrate is rapidly heated to a target temperature and is allowed to cool freely.

Figure 2:
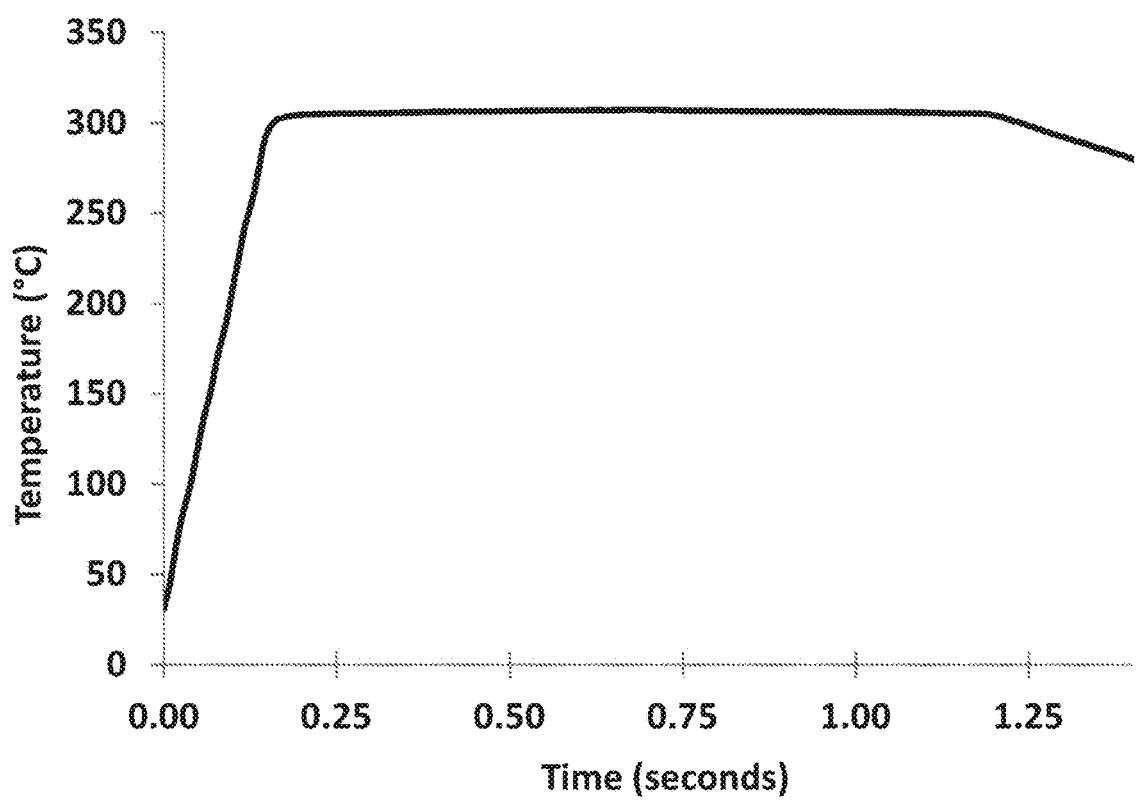
FIG. 2 shows a plateau heating temperature versus time chart.

FIG. 2 shows a temperature to time chart of plateau heating. The foil substrate is rapidly heated to a target temperature by the initial ramp-up heating and then the temperature is maintained at approximately ±1° C. of the target temperature for 1 s.

Figure 3:
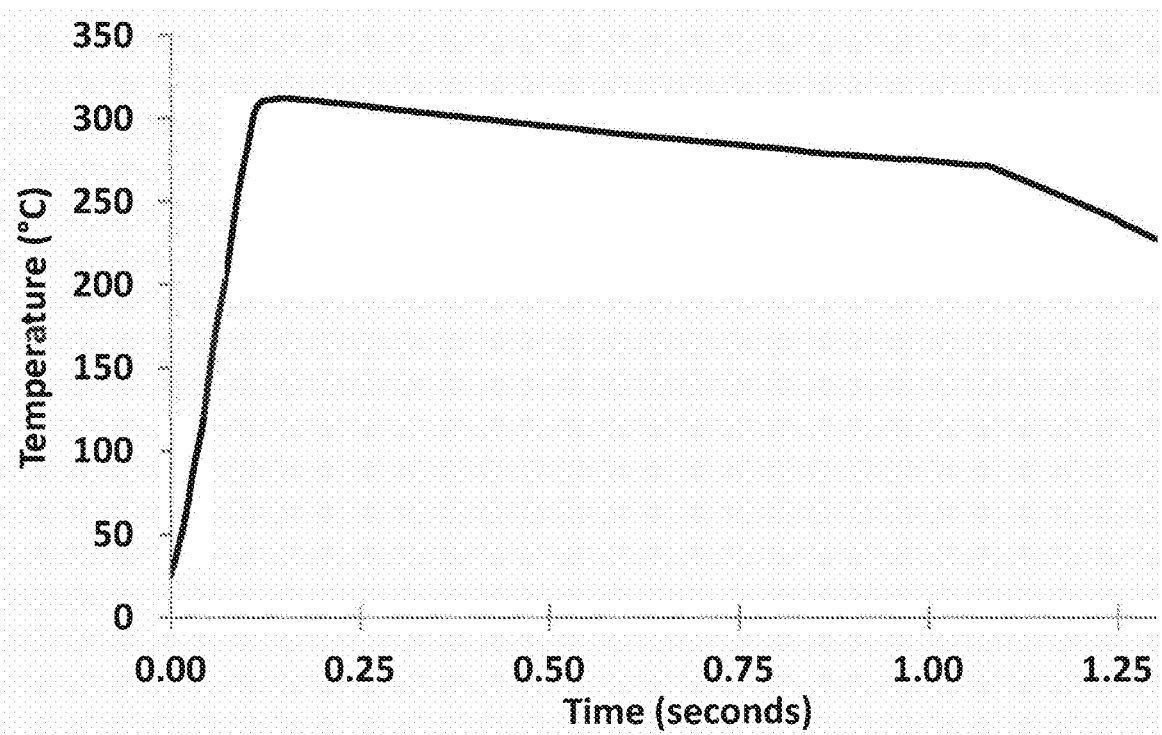
FIG. 3 shows a tempered cooling temperature versus time chart.

FIG. 3 shows a temperature to time chart of tampered cooling. The foil substrate is rapidly heated to a target temperature by the initial ramp-up heating and then the temperature is allowed to go down, in this specific example about 40° C. during 1 s.

Figure 4:
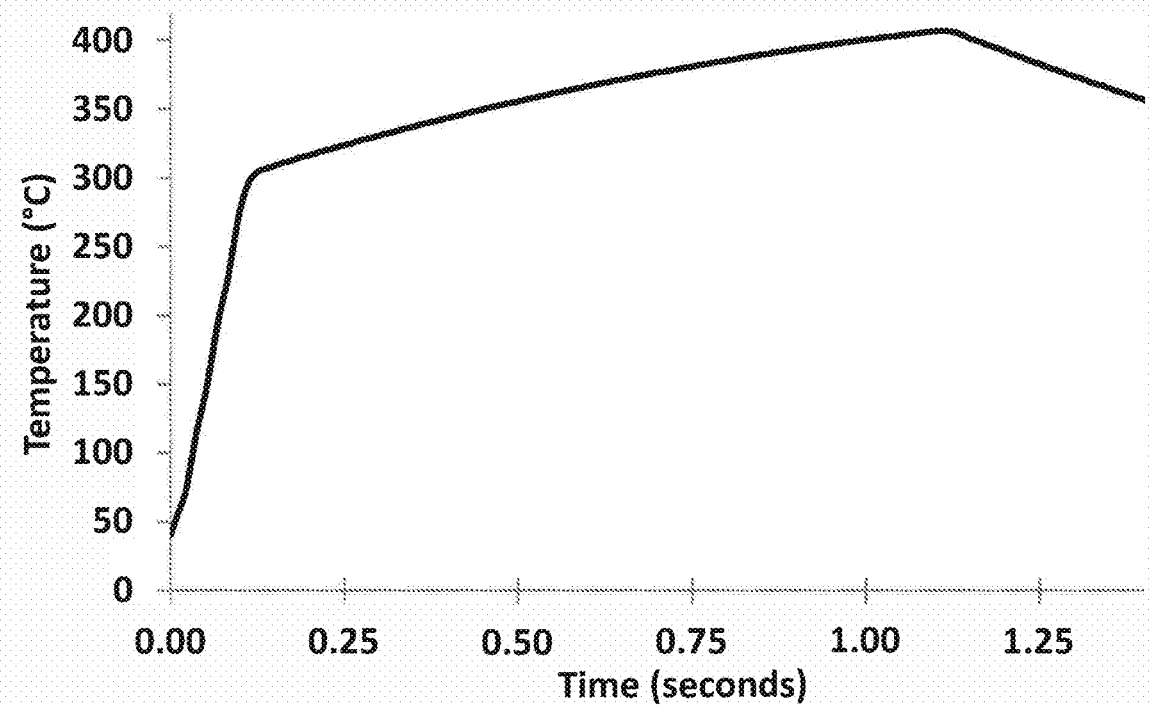
FIG. 4 shows a progressive heating temperature versus time chart.

FIG. 4 shows a temperature to time chart of progressive heating. The foil substrate is rapidly heated to a target temperature by the initial ramp-up heating and then the temperature is further increased, in this specific example about 100° C. during 1 s.

Figure 5:
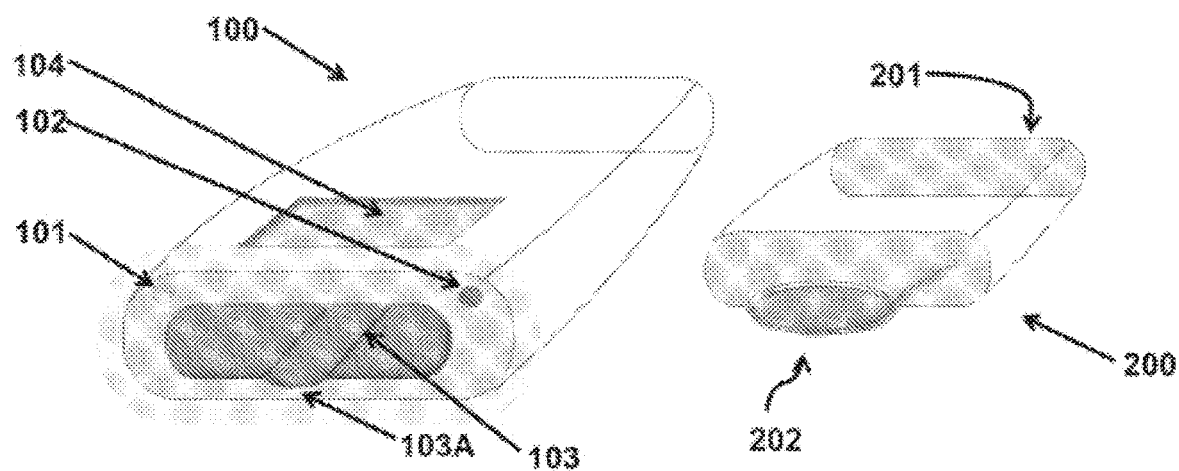
FIG. 5 shows a device concept for drug delivery.

FIG. 5 shows a device concept for aerosol drug delivery.
1) The handheld medical device (100) powers on when the disposable cartridge (200) is inserted
   i) LED on left side (101) shines GREEN if new disposable cartridge is detected
   ii) LED on left side (101) shines RED when inserted disposable cartridge is expended or detected as previously used
   iii) RFID or other technology may be present to uniquely identify each cartridge
2) Second LED (102) shines RED if battery charge is low
3) Keying feature (103A) in the cartridge slot (103) ensures proper orientation and/or attachment of the cartridge (200), alternatively cartridge (200) with symmetrical design could be used. The cartridge slot (103) may include a spring actuated cover to minimize dust ingress.
4) Optional LCD (104) may display further information
5) Connector jack for battery charging and intake air vent located in back of the handheld medical device (100).
6) Bill of materials for disposable cartridge (200):
   i) an upper housing
   ii) a lower housing
   iii) PCB or flex circuit with stiffener to support foil substrate with connector.
   iv) a drug coated foil substrate
   v) a RFID tag
   vi) a connector and air flow interface in the back of disposable cartridge (201)
   vii) an air outlet adapted as a mouth piece (202)

Optionally the device will store the cartridge ID after it is inserted so that in the future, it can determine if the cartridge is new or previously used. Other ID data can be used to indicate lot number, expiration date, drug, dosage level.

Other features that may be included in the device include:

Lock-out timer: timer to limit frequency of dosing.

Dosing reminder: device to remind patient to take drug.

Dose log: capture time and date each time dose is taken.

Device Access Security: biometric or other method to restrict access to device operation.

Battery charge indicator.

Bluetooth connectivity: device paired to mobile device. Signal sent when dose is taken. Mobile device app can be set up to alert others (physician, family members, care taker, etc.) a dose has been taken.

FIG. 6 shows layer 1 of concepts A and B of a disposable cartridge. This figure depicts an inlet (220) on the back of the device flanked by pneumatic sealings (205), the airflow (203) passes through a perforated bulkhead (206), as an example of means for distributing airflow from air inlets, and a stiffener (204), as an example of means for holding a foil substrate. The airway or airflow (203) is indicated with arrows.

FIG. 7 shows layer 2 of concept A layer 2 of a disposable cartridge. This figure depicts the foil substrate (209) on a flex circuit (207) and shows as well the drug coated (210) on the foil substrate (209). The electrical connector (208) is used to connect the disposable cartridge to the handheld medical device in order to energize the foil substrate (209). An example of foil substrate is ~0.00075" (~0.019 mm) thick stainless steel.

FIG. 8 shows layer 2 of concept B of a disposable cartridge. This figure depicts the foil substrate (209) on a on a Printed Circuit Board (PCB) (211) and shows as well the drug coated (210) on the foil substrate (209). The electrical connector (208) is used to connect the disposable cartridge to the handheld medical device in order to energize the foil substrate.

FIG. 9 shows linear slits (212) in the foil substrate (209) passing through the area coated with the drug (210) as thermal conductivity barriers.

FIG. 10 shows chevron slits (213) in the foil substrate (209) passing through the area coated with the drug (210) as thermal conductivity barriers.

FIG. 11 shows serpentine slits (214) in the foil substrate (209) passing through the area coated with the drug (210) as thermal conductivity barriers.

FIG. 12 shows pattern of holes (215) in the foil substrate (209) through the area coated with the drug (210) as thermal conductivity barriers. The holes can be round, obround, oval, or any other and can be in random or non-random patterns on the foil substrate (209).

FIG. 13 shows the drug coating biased downstream (216) on the foil substrate (209). In other words, the geometrical center of the drug coated area is closer to the downstream edge of the foil substrate (209) than to the upstream edge of the foil substrate (209).

FIG. 14 shows the drug coating biased upstream (217) on the foil substrate (209). In other words, the geometrical center of the drug coated area is closer to the upstream edge of the foil substrate (209) than to the downstream edge of the foil substrate (209).

Figure 15A:
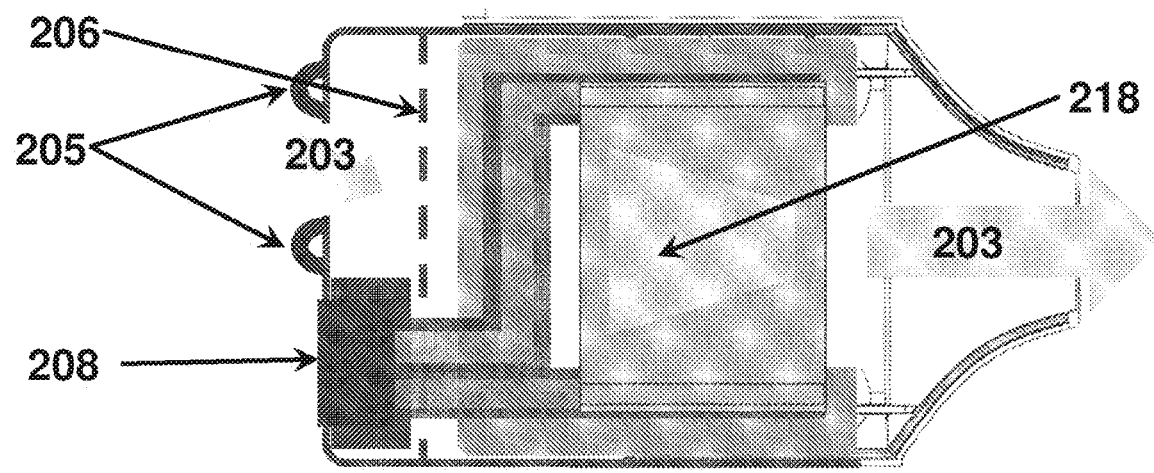
FIG. 15a shows a drug coating area to match selective heat zones on foil substrate.

FIG. 15a shows a drug coating area to match selective heat zones on foil substrate (209). In this case a drug coated area in trapezoidal form (218) is shown.

Figure 15B:
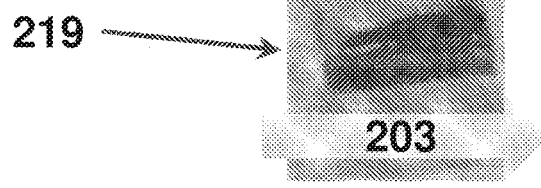
FIG. 15b shows a picture of a foil substrate post aerosolization.

FIG. 15b shows a picture of a foil substrate post aerosolization showing hot (dark) zones (219). The broader part of the trapezoid is in the upstream edge of the foil substrate (209) following the airway (203), the narrower part is in the downstream edge of the foil substrate (209) following the airway (203).

Figure 16:
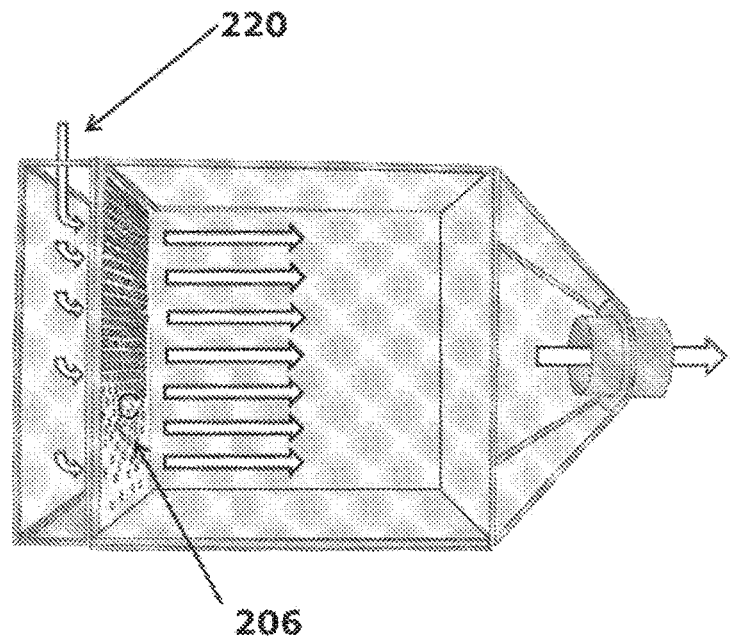
FIG. 16 shows a perforated bulkhead to distribute inlet air.

FIG. 16 shows a concept of a disposable cartridge with an air inlet (220) on the side of the device, a perforated bulkhead (206) to distribute the inlet air. The arrows show the direction of the airflow (203).

Figure 17:
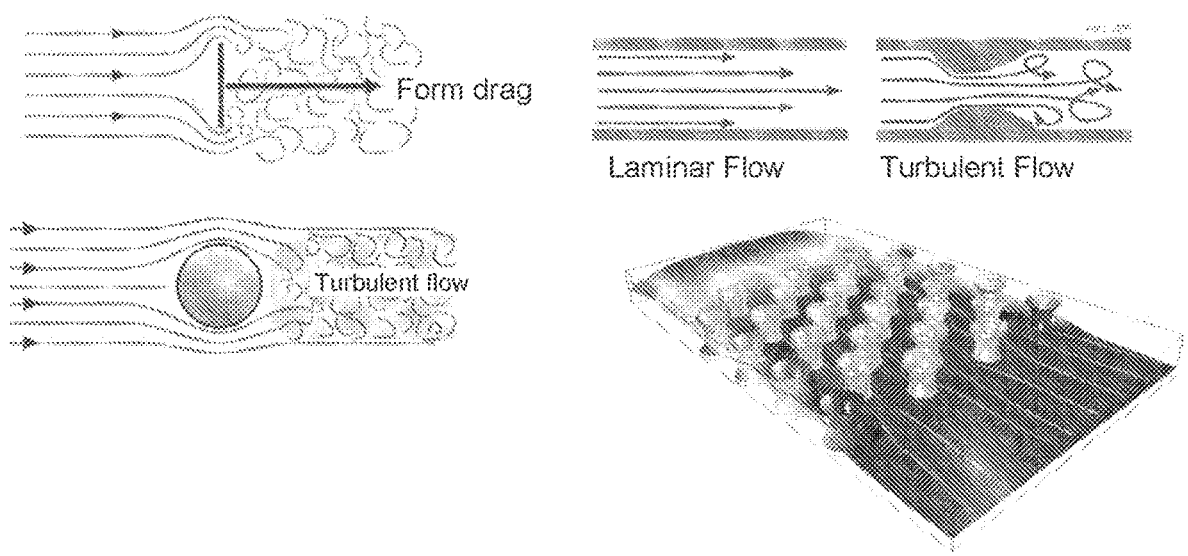
FIG. 17 shows examples of obstructions to introduce turbulence and distribute air flow.

FIG. 17 shows examples of obstructions or restrictions in the airflow path to introduce turbulence to achieve more uniform convective heat loss of the foil substrate.

Obstructions can be posts, bumps, etc. protruding from the inside surface of the airway. Generally, obstruction features would be positioned upstream of the foil substrate to minimize deposition of aerosol particles on obstruction features. 302 represents laminar flow. Some examples of turbulence introduced are form drag (301) and turbulent flow (303).

Figures 18, 19:
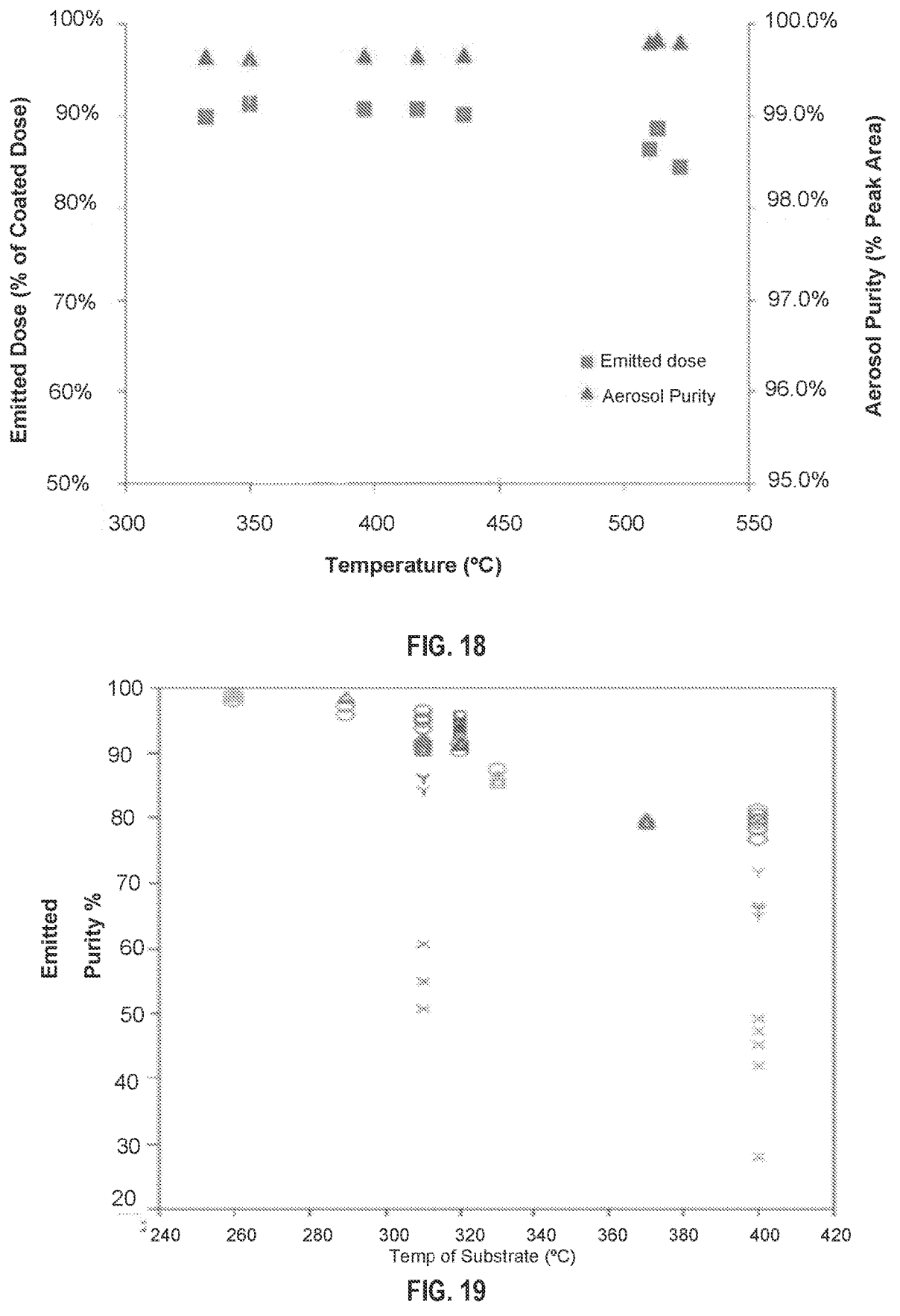

FIG. 18 shows an example of a drug that can withstand a large range of vaporization temperatures.

FIG. 19 shows an example of a drug that is sensitive to vaporization temperature.

Figure 20:
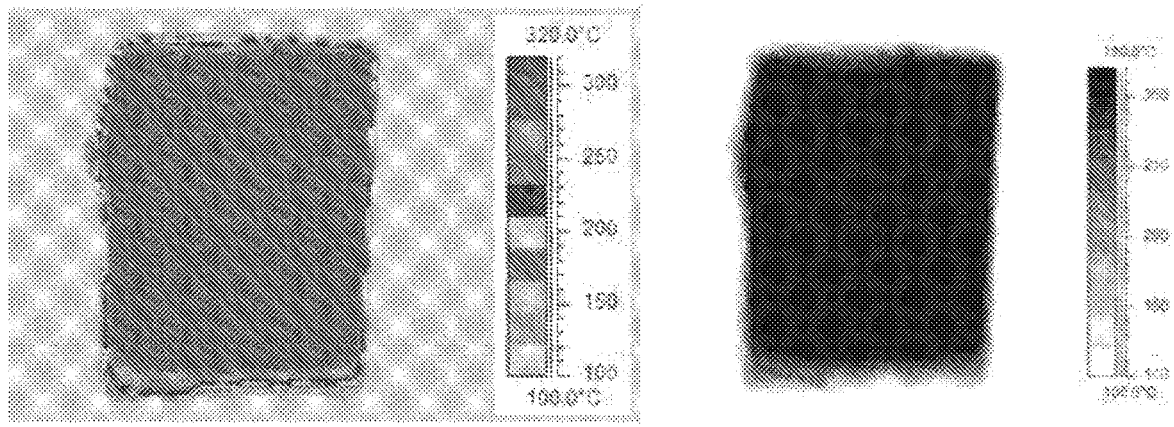
FIG. 20 shows thermal images of foil substrate during electrical resistance heating without airflow.

FIG. 20 shows thermal images of a foil substrate during electrical resistance heating without airflow.

Figure 21:
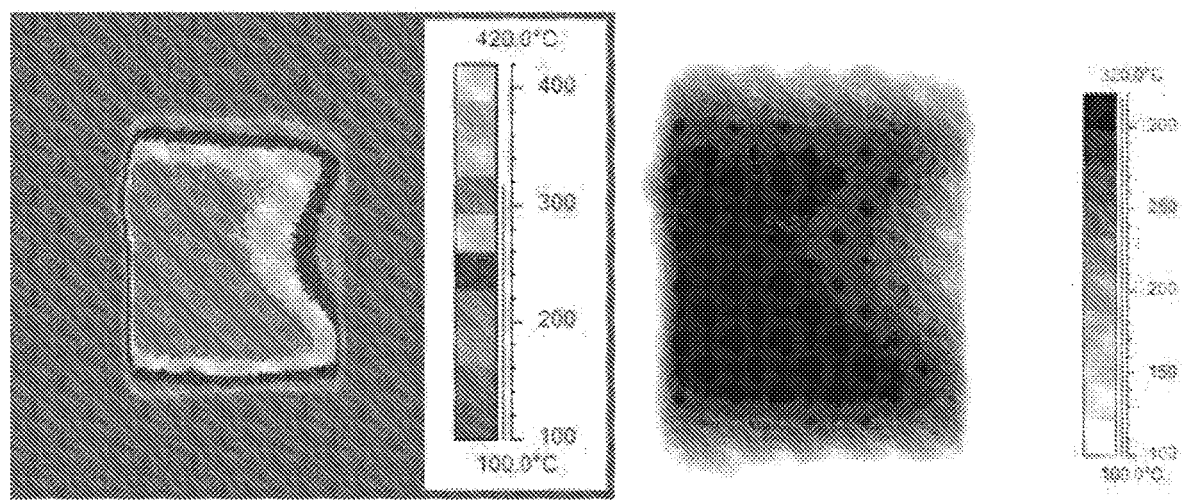
FIG. 21 shows thermal images of foil substrate during electrical resistance heating with airflow.

FIG. 21 shows thermal images of foil substrate during electrical resistance heating with airflow.

FIG. 22 shows a commercially available lithium polymer battery suitable for use in a portable handheld condensation aerosol drug delivery device. This specific battery has the following characteristics:

| | Typical Capacity[1] | 3.2 Ah |
|---|---|---|
| | Nominal Voltage | 3.7 V |
| Change Condition | Max. Current | 6.4 A |
| | Voltage | 4.2 V ± 0.03 V |
| Discharge Conditions | Continuous Current | 64.0 A |
| | Peak Current | 128.0 A |
| | Cut-off Voltage | 2.7 V |
| | Cycle Life | >500 cycles |
| Operating Temp. | Charge | 0~40° C. |
| | Discharge | −20~60° C. |
| Dimension | Thickness (mm) | 7.6 ± 0.2 |
| | width (mm) | 42.5 ± 0.5 |
| | Length (mm) | 127.5 ± 0.5 |
| | weight (g) | 84.0 ± 2.5 |

[1]Typical Capacity: 0.5 C, 4.2~2.7 V @25° C.

FIG. 23 shows a portable, handheld, battery operated, electrically heated, condensation aerosol drug delivery device concept layout with the housing (103) for the disposable cartridge; the batteries (105); the printed circuit board (106), which controls the release of electricity to the disposable cartridge (200); and the air inlet with a grill (107). Below is a rear view of the device. As an example, the housing (103) for the disposable cartridge measures ~42 mm wide×~50 mm deep×~15 mm tall.

Figure 24A:
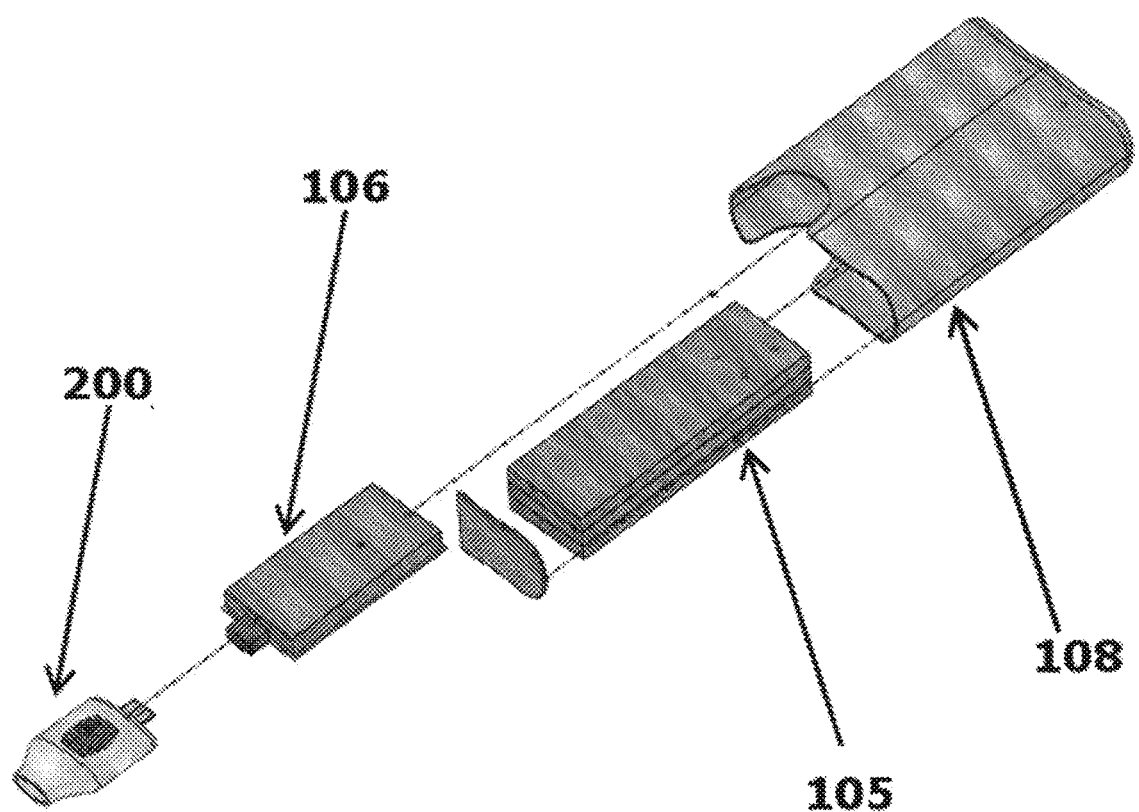
FIGS. 24a-24c shows different views of the handheld device concept.
Figure 24B:
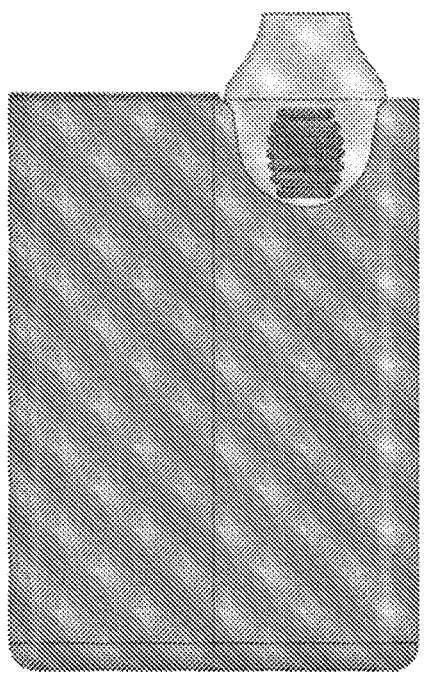
Figure 24C:
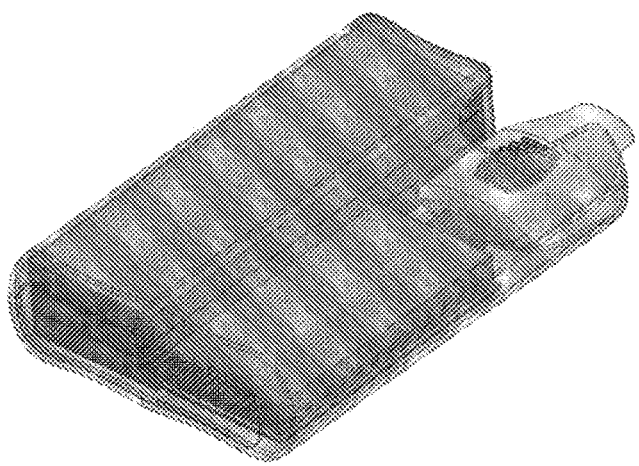

FIGS. 24a, 24b and 24c show different views of the handheld medical device concept.

FIGS. 23-24c show, from different points of view, the disposable cartridge (200) (an example of disposable cartridge measures ~38 mm wide×~50 mm deep×~12 mm tall (excluding mouthpiece)); the batteries (105) (an example of battery measures ~25 mm total stack height); the printed circuit board assembly (106) (an example of printed board assembly measures ~42 mm×~60 mm (not including connector extension)); the air inlet grill (107); and the device enclosure (108) (an example of device enclosure measures ~135 mm long×~90 mm wide×~30 mm tall).

Figure 25:
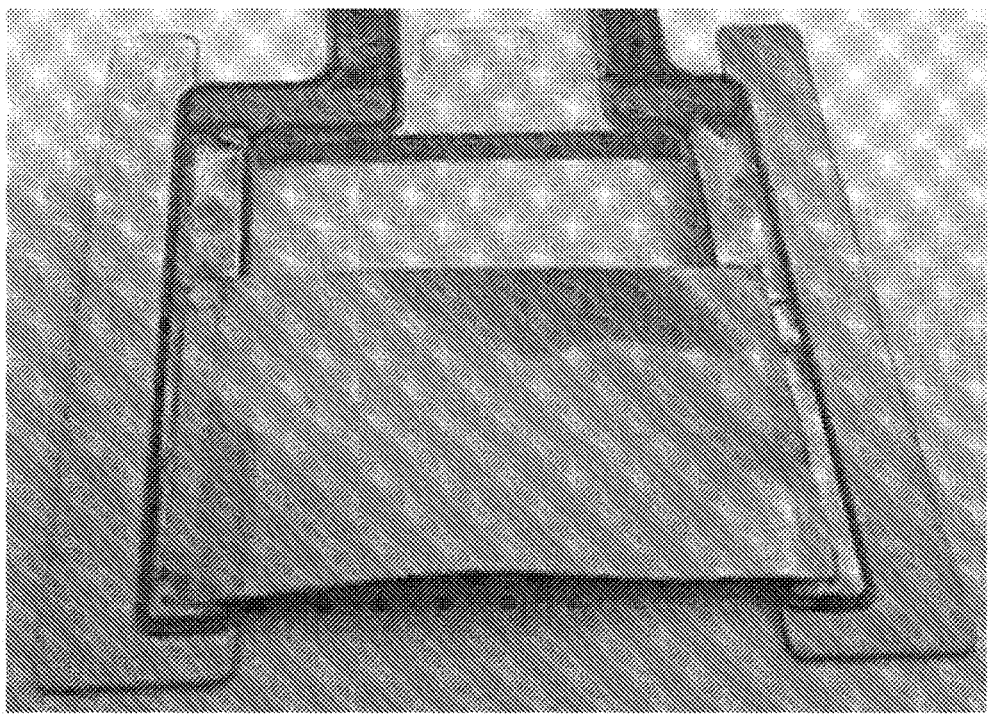
FIG. 25 shows a stainless steel foil substrate soldered to copper traces of a flex circuit.

FIG. 25 shows a stainless steel foil substrate soldered to copper traces of a flex circuit. It can be clearly seen that the foil substrate is deformed.

Figure 26:
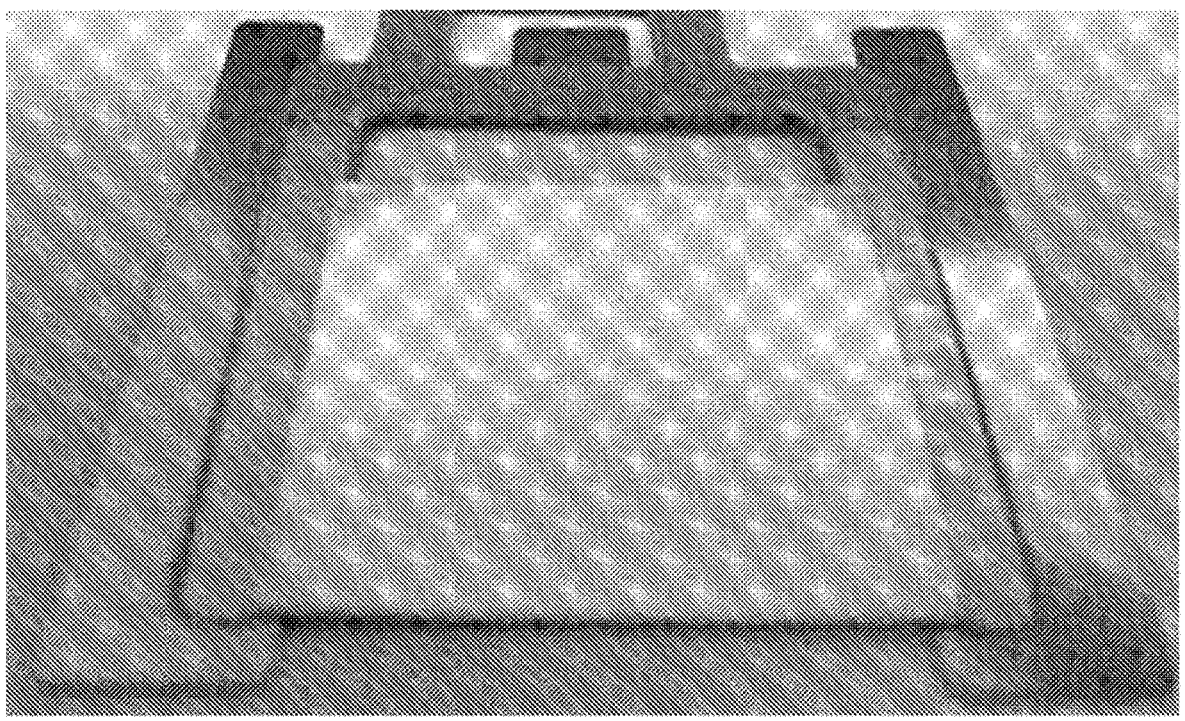
FIG. 26 shows a stainless steel foil substrate laser welded to copper traces of a flex circuit.

FIG. 26 shows a stainless steel foil substrate laser welded to copper traces of a flex circuit. It can be clearly seen that the foil substrate is not deformed when is laser welded.

Figure 27:
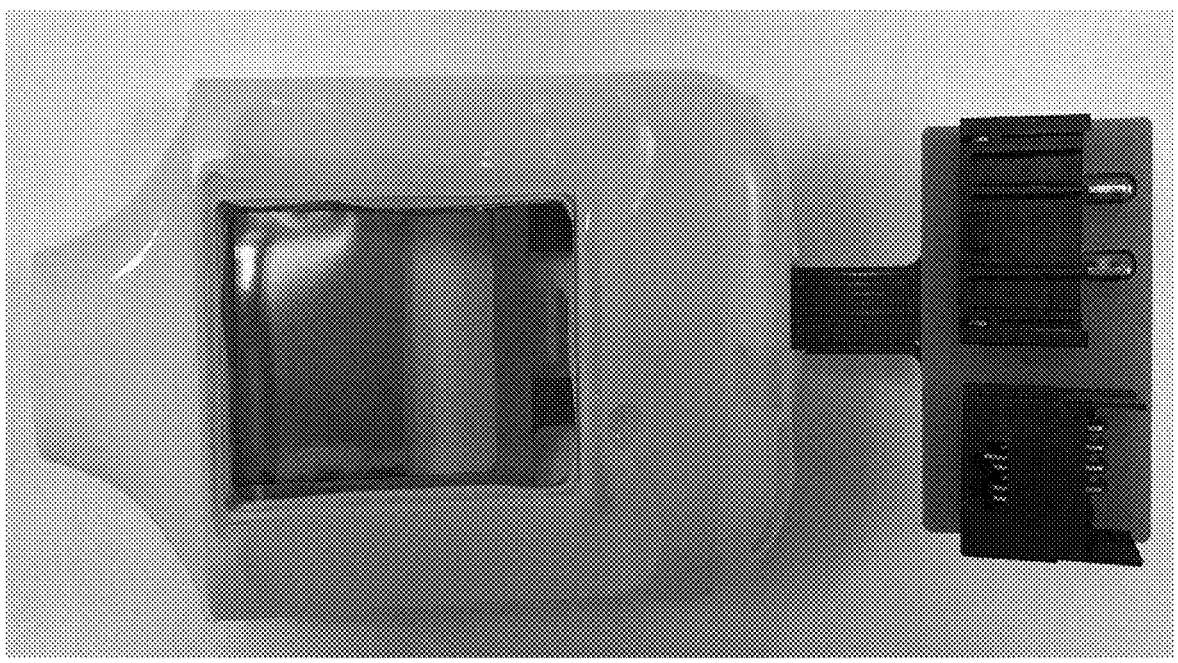
FIG. 27 shows a condensation aerosol device modified to incorporate a calcium fluoride window for infrared imaging.

FIG. 27 shows a development prototype of a disposable cartridge modified to incorporate a calcium fluoride window for infrared imaging and an external connector to the handheld medical device.

Figure 28:
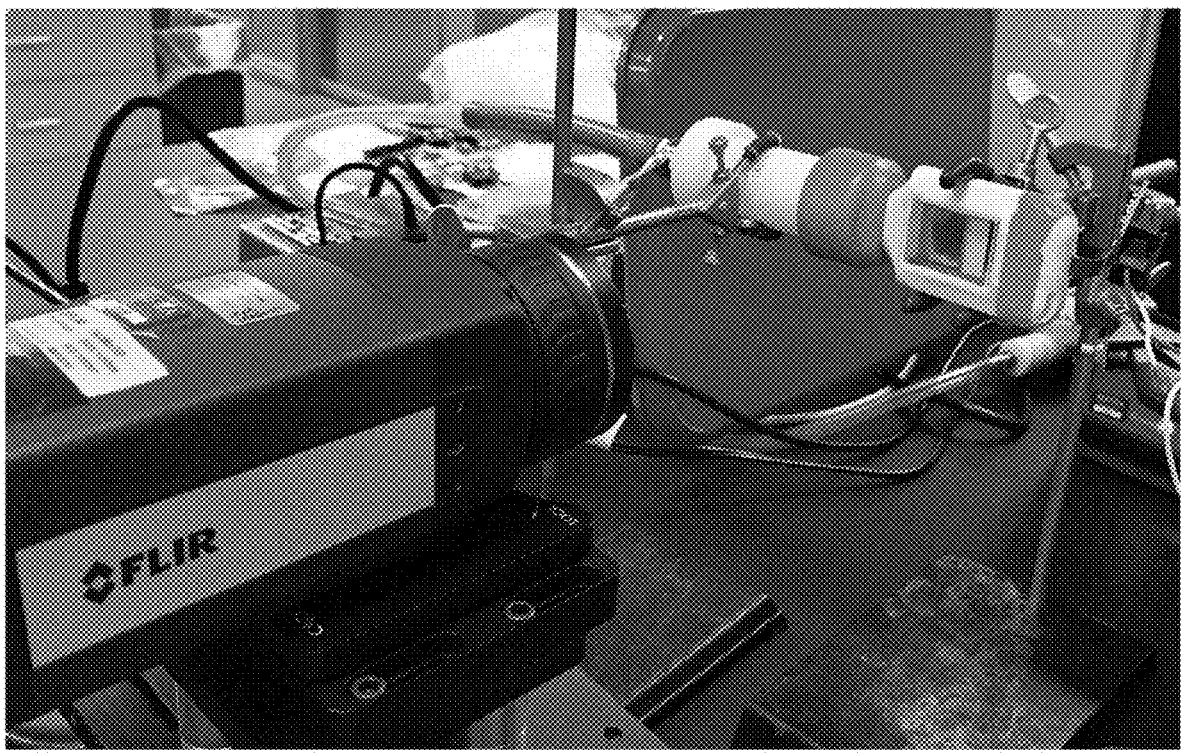
FIG. 28 shows a thermal camera set-up to capture thermal images from modified condensation aerosol device.

FIG. 28 shows a thermal camera set-up to capture thermal images from modified disposable cartridge.

Figure 29:
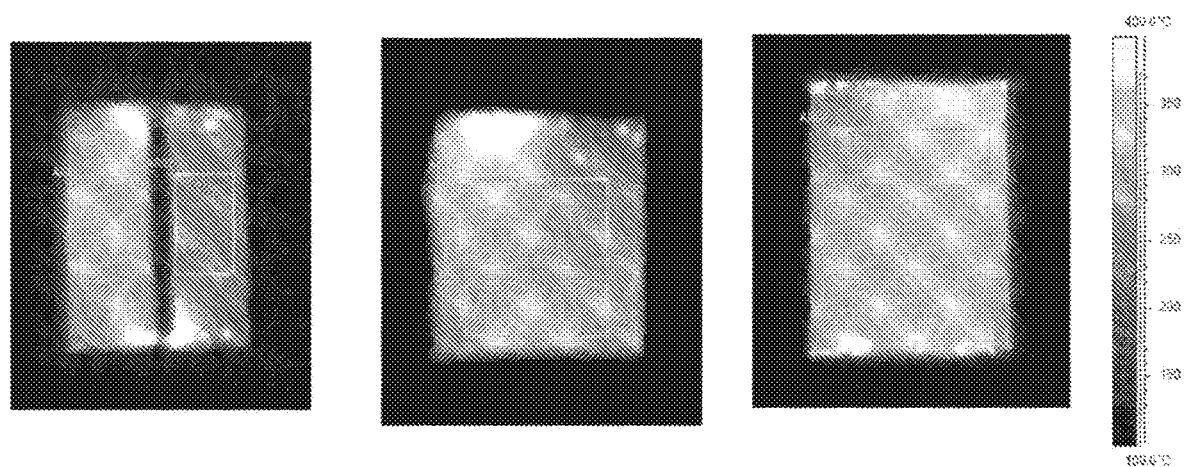
FIG. 29 shows thermal images demonstrating that poor soldering quality between copper and stainless steel foil substrate results in localized hot and cool zones.

FIG. 29 shows thermal images demonstrating that poor soldering quality between copper and stainless steel foil substrate results localized hot and cool zones.

Figure 30:
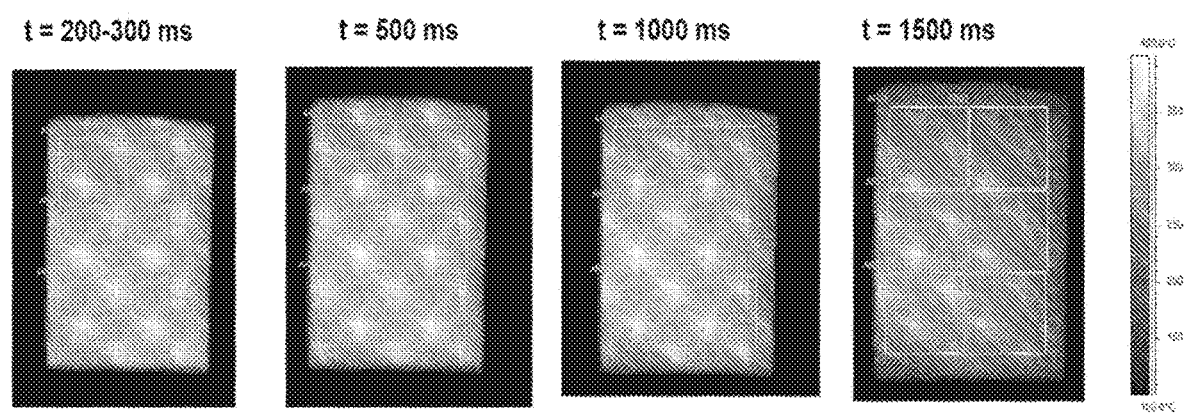
FIG. 30 shows thermal images demonstrating that laser welding stainless steel foil substrate to copper yields uniform heating of the substrate.

FIG. 30 shows thermal images demonstrating that laser welding stainless steel foil substrate to copper yields uniform heating of the substrate.

Definitions

As defined herein, the following terms shall have the following meanings when reference is made to them throughout the specification.

"Aerodynamic diameter" of a given particle refers to the diameter of a spherical droplet with a density of 1 g/mL (the density of water) that has the same settling velocity as the given particle.

"Aerosol" refers to a collection of solid or liquid particles suspended in a gas.

"Aerosol mass concentration" refers to the mass of particulate matter per unit volume of aerosol.

Antistatic material includes, but are not limited to, airway materials which are antistatic as well as coatings for the airway. These antistatic materials include metallized airways (produced by coating the inner wall of the airway with conductive metals such as stainless steel/copper/copper/stainless steel, and/or by applying a metallic tape (like copper) to the inner and outer walls of the airway), the use of an antistatic spray (such as the Staticide brand) on the default airway, and/or the use of antistatic plastics (such as the Permastat or Permastat plus brands) as air way materials. Materials with antistatic properties are included in this disclosure. Further information regarding the use of antistatic material can be found on WO16145075.

"Condensation aerosol" refers to an aerosol that has been formed by the vaporization of a composition and subsequent cooling of the vapor, such that the vapor condenses to form particles.

"Condition" includes acute conditions, intermittent conditions and/or chronic conditions.

"Decomposition index" refers to a number determined by subtracting the purity of the generated aerosol, expressed as a fraction, from 1.

"Drug" means any substance that is used in the prevention, diagnosis, alleviation, treatment or cure of a condition. The drug is preferably in a form suitable for thermal vapor delivery, such as an ester, free acid, free base, or salt form. The drugs are preferably other than recreational drugs. More specifically, the drugs are preferably other than recreational drugs used for non-medicinal recreational purposes, e.g., habitual use to solely alter one's mood, affect, state of consciousness, or to affect a body function unnecessarily, for recreational purposes. The terms "drug", "compound", and "medication" are used herein interchangeably. Drug also includes the term pro drug, wherein upon heat activation, the pro drug becomes an active drug.

"Drug composition" refers to a composition that comprises only pure drug, two or more drugs in combination, or one or more drugs in combination with additional components. Additional components can include, for example, pharmaceutically acceptable excipients, carriers, additives and surfactants.

"Drug degradation product" or "thermal degradation product" are used interchangeably and means any byproduct, which results from heating the drug(s) and is not responsible for producing a therapeutic effect.

"Drug supply article" or "drug supply unit" are used interchangeably and refers to a substrate with at least a portion of its surface coated with one or more drug compositions. Drug supply articles of the invention may also include additional elements such as, for example, but not limitation, a heating element.

"Fraction drug degradation product" refers to the quantity of drug degradation products present in the aerosol particles divided by the quantity of drug plus drug degradation product present in the aerosol, i.e. (sum of quantities of all drug degradation products present in the aerosol)/((quantity of drug(s) present in the aerosol)+(sum of quantities of all drug degradation products present in the aerosol)). The term "percent drug degradation product" as used herein refers to the fraction drug degradation product multiplied by 100%, whereas "purity" of the aerosol refers to 100% minus the percent drug degradation products.

"Geometric center" refers to the arithmetic mean position of all the points in the shape of the drug composition (210) coated on the foil substrate (209).

"Heat stable drug" refers to a drug that has a thermal stability ratio, TSR≥9 when vaporized from a film of some thickness between 0.01 μm and 20 μm.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Number concentration" refers to the number of particles per unit volume of aerosol.

"Prodrug" is a compound that can be chemically converted in vitro into a physiologically active compound, i.e., it is a precursor of a desired physiologically active compound. Typically, the prodrug does not have physiological activity, but the term is not so limited and encompasses compounds that may have physiological activity. A "heat-labile" or "thermally labile" prodrug is a prodrug that can be converted into physiologically active compound through heating, i.e., subjecting the prodrug to an elevated temperature.

"Purity" as used herein, with respect to the aerosol purity, means the fraction of drug composition in the aerosol/(the fraction of drug composition in the aerosol plus drug degradation products). Thus, purity is relative with regard to the purity of the starting material. For example, when the starting drug or drug composition used for substrate coating contained detectable impurities, the reported purity of the aerosol does not include those impurities present in the starting material that were also found in the aerosol, e.g., in certain cases if the starting material contained a 1% impurity and the aerosol was found to contain the identical 1% impurity, the aerosol purity may nevertheless be reported as >99% pure, reflecting the fact that the detectable 1% purity was not produced during the vaporization-condensation aerosol generation process.

A "Sensitive Drug" refers to a drug that is vaporization temperature sensitive and/or sensitive to degradation. These drugs are characterized by a higher rate of change in purity of the aerosol as a function of substrate temperature compared to drugs that are less sensitive. Drugs that are less sensitive can maintain a stable level of aerosol purity over a wide range of vaporization temperatures whereas sensitive drugs require a narrow vaporization temperature range to maintain a desired target purity.

"Settling velocity" refers to the terminal velocity of an aerosol particle undergoing gravitational settling in air.

A "shape" for the coating of the drug can include rectangles, trapezoids, triangles, parabolic, etc. The shape is determined by identifying the region(s) of the foil substrate where the surface temperature is optimal for vaporizing drugs, including sensitive drugs. Additionally, the coating of the drug can have various film thicknesses. The thickness of the film can be uniform. The thickness of the film can have different thicknesses in different areas. The different thicknesses can be a step function or it can be a gradient difference from one thickness to another. The thickness can be in a range of 0.01 to 50 μm.

"Support" refers to a material on which the composition is adhered, typically as a coating or thin film. The term "support" and "substrate" are used herein interchangeably.

"Subject" refers to a mammal, a human in a capacity as a patient or a subject of a clinical trial for which the device is intended to deliver an aerosol to treat a specific disorder.

"Substantially free of" means that the material, compound, aerosol, etc., being described is at least 95% free of the other component from which it is substantially free.

"Treatment" refers to treating chronic and acute conditions as well as preventative or prophylactic treatment.

"Typical patient tidal volume" refers to 1 L for an adult patient and 15 mL/kg for a pediatric patient.

"Therapeutically effective amount" means the amount required to achieve a therapeutic effect. The therapeutic effect could be any therapeutic effect ranging from prevention, symptom amelioration, symptom treatment, to disease termination or cure.

"Thermal stability ratio" or "TSR" means the % purity/ (100%−% purity) if the % purity is <99.9%, and 1000 if the % purity is ≥99.9%. For example, a respiratory drug vaporizing at 90% purity would have a TSR of 9. Generally, temperature sensitive drug will have a TSR of 9 or higher. Drugs less sensitive have purities in the 99% range so their TSRs are 99 or higher.

"4 μm thermal stability ratio" or "4TSR" means the TSR of a drug determined by heating a drug-comprising film of about 4 μm in thickness under conditions sufficient to vaporize at least 50% of the drug in the film, collecting the resulting aerosol, determining the purity of the aerosol, and using the purity to compute the TSR. In such vaporization, generally the about 4-micron thick drug film is heated to around 350° C. but not less than 200° C. for around 1 second to vaporize at least 50% of the drug in the film.

"1.5 μm thermal stability ratio" or "1.5TSR" means the TSR of a drug determined by heating a drug-comprising film of about 1.5 μm in thickness under conditions sufficient to vaporize at least 50% of the drug in the film, collecting the resulting aerosol, determining the purity of the aerosol, and using the purity to compute the TSR. In such vaporization, generally the about 1.5-micron thick drug film is heated to around 350° C. but not less than 200° C. for around 1 second to vaporize at least 50% of the drug in the film.

"0.5 µm thermal stability ratio" or "0.5TSR" means the TSR of a drug determined by heating a drug-comprising film of about 0.5 µm in thickness under conditions sufficient to vaporize at least 50% of the drug in the film, collecting the resulting aerosol, determining the purity of the aerosol, and using the purity to compute the TSR. In such vaporization, generally the about 0.5-micron thick drug film is heated to around 350° C. but not less than 200° C. for around 1 second to vaporize at least 50% of the drug in the film.

"Vapor" refers to a gas, and "vapor phase" refers to a gas phase. The term "thermal vapor" refers to a vapor phase, aerosol, or mixture of aerosol-vapor phases, formed preferably by heating.

"Ramp-up" refers to the phase of rapidly heating the foil substrate up to the target temperature. In this context, "rapidly heating" means heating at a rate of 3 to 10° C./ms.

"Heating rate" refers to the phase after the ramp-up. During the heating rate the target temperature obtained after the ramp-up is controlled and generally has a duration of 1 to 3 seconds. The heating rate can be selected form one or more of plateau heating, tampered cooling or progressive heating. After the heating rate phase, the foil substrate is allowed to cool without control. The heating rate phase allows controlling the emitted dose of the drug, and/or the purity and/or the particle size of the drug aerosol particles.

"Plateau heating" refers to a heating rate of the foil substrate after the target temperature has been reached. In this heating rate, the temperature of the foil substrate is maintained within a range of ±5° C. for up to 3 s, preferably up to 1 s.

"Tampered cooling" refers a heating rate of the foil substrate after the target temperature has been reached. In this heating rate, the temperature of the foil substrate decreases in a controlled way at a rate of 0.2 to 0.01° C./ms for up to 3 s, preferably up to 1 s.

"Progressive heating" refers to a heating rate of the foil substrate after the target temperature has been reached. In this heating rate, the temperature of the foil substrate increases in a controlled way at a rate of 0.01 to 0.2° C./ms for up to 3 s, preferably up to 1 s.

The measurements of the temperature in the foil substrate may be taken in the foil substrate uncoated of drug using a thermal camera as explained in Example 1. Other methods for measuring the temperature of the foil substrate may be used including, but not limited to direct contact with a thermocouple, optical measurement of the temperature or measurement of electrical resistance across the foil substrate.

These and other aspects of the present invention are described further in the detailed description of the preferred embodiments of the invention which follow.

Drugs

Drugs that are applicable for the disclosed device include: Acetaminophen, Amantadine, Atenolol, Bromazepam, Brompheniramine Maleate, Caffeine, Celecoxib, Clofazimine, Clonidine, Codeine, Cyproheptadine, Dapsone, Diclofenac ethyl ester, Diflunisal, Fenfluramine, Flumazenil, Flurbiprofen, Galanthamine, Hydromorphone, Indomethacin Norcholine Ester, Ketorolac Methyl Ester, Ketorolac Norcholine Ester, Melatonin, Memantine, Methadone, Morphine, Nabumetone, Naproxen, Orphenadrine, Phenytoin, Pindolol, Procainamide, Propafenone, Quinidine, Quinine, Spironolactone, Thalidomide, Theophylline, Tramadol Hydrochloride, Trazodone, Triamterene, Ketotifen, Brompheniramine, Butorphanol, Diazepam, Estazolam, Ketamine, Meperidine, Oxycodone, Chlorpheniramine, Doxylamine, Ethacrynic acid, Flunitrazepam, Haloperidol, Lidocaine, Loxapine Succinate, Olanzapine, Tacrine, Trifluoperazine, Amoxapine, Chlorzoxazone, Ibuprofen, Loxapine, Maprotiline, Pergolide, Piribedil, Protriptyline HCl, Tocainide, Zonisamide, Azatadine, Chlorpheniramine Maleate, Cyproheptadine HCl, Flecainide, Isocarboxazid, Ketoprofen ethyl ester, Loratadine, Methoxsalen, Propranolol, Testosterone, Benztropine, Clozapine, Midazolam, Paroxetine, Sertraline, Valproic Acid, Zaleplon, Clomipramine, Loperamide, Mexiletine HCl, Venlafaxine, Amitriptyline, Betahistine, Naratriptan, Pramipexole, Sildenafil, Terbutaline, Vitamin E, Flurazepam, Metoprolol, Naloxone, Rizatriptan, Selegiline, Tadalafil, Triazolam, Trimipramine, Bupropion HCl, Doxepin, Imipramine, Lamotrigine, Metaproterenol, Metoclopramide, Morphine, Nortriptyline, Perphenazine, Quetiapine, Ciclesonide, Alprazolam, Carbinoxamine Maleate, Cyclobenzaprine, Disopyramide, Ephedrine, Granisetron, Indomethacin, Indomethacin Ethyl Ester, Indomethacin Methyl Ester, Ketoprofen Methyl Ester, Ketorolac Ethyl Ester, Mirtazapine, Nalbuphine, Nicotine, Ropinirole, Ropinirole Fumarate. The preceding list of drugs have shown purities above 99% when aerosolized using the invention described herein.

Other drugs that are more sensitive to vaporization temperatures that are applicable for the disclosed device include: Acebutolol, Hydroxychloroquine, Meperidine, Estradiol, Fenoprofen, Prochlorperazine, Toremifene, Hydroxyzine, Atropine, Buprenorphine, Bumetanide, Fentanyl, Ibutilide, Pyrilamine, Zolmitriptan, Zotepine, Chlordiazepoxide, Citalopram, Ketoprofen, Pergolide, Ropinirole HCl, Rotigotine, Efavirenz, Zopiclone, Sumatriptan, Bergapten, Buspirone HCl, Eletriptan, Nortriptyline, Colchicine, Flunisolide, Nefazodone, Rofecoxib, Tranylcypromine HCl, Fluoxetine, Promethazine, Trimipramine Maleate, Meclizine, Diltiazem, Temazepam, Tolterodine, Valdecoxib, Apomorphine Diacetate, Donepezil, Sotalol, Tramadol, Cinnarizine, Isotretinoin, Zolpidem, Buspirone, Chlorpromazine, Albuterol, Verapamil, Naltrexone, Telmisartan, Hyoscyamine, Tranylcypromine, Esmolol, Pioglitazone, Treprostinil, Dipyridamole, Apomorphine HCl, Linezolid, Carbinoxamine, Butorphanol Tartrate, Clemastine, Fluconazole, Tolfenamic Acid, Lovastatin, Apomorphine HCl Diacetate, Promazine, Sibutramine, Astemizole, Diphenhydramine, Pyrilamine Maleate, Diphenhydramine HCl, Fluphenazine, Citalopram, Triamcinolone Acetonide, Fluticasone Propionate, Buprenorphine HCl, Tamoxifen, Aripiprazole, Frovatriptan, Nefazodone, Protriptyline, Oxybutynin, Meclizine, Benazepril, Ethambutol, Scopolamine, Nicotine Salts, and Treprostinil Salts. The list shows drugs in order of aerosol purity when aerosolized using the invention described herein, with the highest purities first and the rest in descending order.

In other embodiments, prodrugs may be deposited on a substrate, e.g., coated as a thin film, without the creation of any covalent bond between the substrate (or a polymer or other chemical moiety attached to the substrate). Upon heating, the prodrug decomposes to generate the drug and any by-products. In a preferred embodiment, the by-products are not toxic. For use in the present invention, the prodrug is typically a solid at standard temperature and pressure. The prodrug is typically a derivative of a phenolic drug compound. In preferred embodiments, the prodrug is selected from the group consisting of a t-butoxycarbonyl derivative of a phenolic drug compound, a carboxylic acid derivative of a phenolic drug compound, and a t-butoxycarbonyl-glycinyl-glycinate-derivative of a phenolic drug compound. Phenolic drug compounds useful in the present invention include without limitation, $\Delta^9$-tetrahydrocannabinol ($\Delta^9$-THC), propofol, estradiol, apomorphine, dopamine, epinephrine, and related compounds.

Aerosol Composition

The compositions described herein typically comprise a drug or drug compounds. The compositions may comprise other compounds as well. For example, the composition may comprise a mixture of drug compounds, a mixture of a drug compound and a pharmaceutically acceptable excipient, or a mixture of a drug compound with other compounds having useful or desirable properties. The composition may comprise a pure drug compound as well. In preferred embodiments, the composition consists essentially of pure drug and contains no propellants or solvents.

Additionally, pharmaceutically acceptable carriers, surfactants, enhancers, and inorganic compounds may be included in the composition. Examples of such materials are known in the art.

In some variations, the aerosols are substantially free of organic solvents and propellants. Additionally, water is typically not added as a solvent, although water from the atmosphere may be incorporated in the aerosol during formation, in particular, while passing air over the film and during the cooling process. In other variations, the aerosols are completely devoid of organic solvents and propellants. In yet other variations, the aerosols are completely devoid of organic solvents, propellants, and any excipients. These aerosols comprise only pure drug, less than 10% drug degradation products, and a carrier gas, which is typically air.

Typically, the drug has a decomposition index less than 0.15. Preferably, the drug has a decomposition index less than 0.10. More preferably, the drug has a decomposition index less than 0.05. Most preferably, the drug has a decomposition index less than 0.025

In some variations, the condensation aerosol comprises at least 5% by weight of condensation drug aerosol particles. In other variations, the aerosol comprises at least 10%, 20%, 30%, 40%, 50%, 60%, or 75% by weight of condensation drug aerosol particles. In still other variations, the aerosol comprises at least 95%, 99%, or 99.5% by weight of condensation aerosol particles.

In some variations, the condensation aerosol particles comprise less than 10% by weight of a thermal degradation product. In other variations, the condensation drug aerosol particles comprise less than 5%, 1%, 0.5%, 0.1%, or 0.03% by weight of a thermal degradation product.

In certain embodiments of the disclosure, the drug aerosol has a purity of between 90% and 99.8%, or between 93% and 99.7%, or between 95% and 99.5%, or between 96.5% and 99.2

Typically, the aerosol has a number concentration greater than $10^6$ particles/mL. In other variations, the aerosol has a number concentration greater than $10^7$ particles/mL. In yet other variations, the aerosol has a number concentration greater than $10^8$ particles/mL, greater than $10^9$ particles/mL, greater than $10^{10}$ particles/mL, or greater than $10^{11}$ particles/mL.

The gas of the aerosol typically is air. Other gases, however, can be used, in particular inert gases, such as argon, nitrogen, helium, and the like. The gas can also include vapor of the composition that has not yet condensed to form particles. Typically, the gas does not include propellants or vaporized organic solvents. In some variations, the condensation aerosol comprises at least 5% by weight of condensation drug aerosol particles. In other variations, the aerosol comprises at least 10%, 20%, 30%, 40%, 50%, 60%, or 75% by weight of condensation drug aerosol particles. In still other variations, the aerosol comprises at least 95%, 99%, or 99.5% by weight of condensation aerosol particles.

In some variations the condensation drug aerosol has a MMAD in the range of about 0.01-3 μm. In some variations the condensation drug aerosol has a MMAD in the range of about 0.1-3 μm. In some variations the aerosol MMAD is less than 5 μm. In some variations the geometric standard deviation around the MMAD of the condensation drug aerosol particles is less than 3.0. In other variations, the geometric standard deviation around the MMAD of the condensation drug aerosol particles is less than 2.5, or less than 2.0.

In certain embodiments of the invention, the drug aerosol comprises one or more drugs having a 4TSR of at least 5 or 10, a 1.5TSR of at least 7 or 14, or a 0.5TSR of at least 9 or 18. In other embodiments of the invention, the drug aerosol comprises one or more drugs having a 4TSR of between 5 and 100 or between 10 and 50, a 1.5TSR of between 7 and 200 or between 14 and 100, or a 0.5TSR of between 9 and 900 or between 18 and 300.

Formation of Condensation Aerosols

Any suitable method may be used to form the condensation aerosols described herein. One such method involves the heating of a composition to form a vapor, followed by cooling of the vapor so that it forms an aerosol (i.e., a condensation aerosol). Methods have been previously described in U.S. Pat. No. 7,090,830. This reference is hereby incorporated by reference in its entirety.

The disclosure teaches a device for producing a condensation aerosol with drugs comprising: an electrically resistive heating element (substrate) comprising a metal foil substrate configured to vaporize a substance disposed thereon; an electrical current delivery device to drive a precise electrical current profile through the substrate to affect electrical resistive heating at a rate that achieves a precise temperature profile on the substrate sufficient to vaporize all or a portion of the coated drug composition within a period of three seconds or less; and an airway which directs inhalation air over the surface of the substrate to entrain and condense the vaporized drug composition into condensation aerosol particles comprising the substance which exit the mouthpiece end of the airway into the user's mouth to reach the deep lung via the airway passages to effect systemic drug delivery. The electrically resistive foil substrate is configured to heat to a precise temperature in a precise profile, that allows for optimal vaporization of the drug for maximal drug delivery regarding emitted dose, purity and particle size to enable deposition into the deep lungs.

Typically, the composition is coated on a substrate, and then the substrate is heated to vaporize the composition. The substrate may be of any geometry and be of a variety of different sizes. It is often desirable that the substrate provide a large surface to volume ratio (e.g., greater than 100 per meter) and a large surface to mass ratio (e.g., greater than 1 $cm^2$ per gram). The substrate can have more than one surface A substrate of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials may be used to construct the substrate. Typically, the substrates are heat-conductive and include metals, such as aluminum, iron, copper, stainless steel, and the like, alloys, ceramics, and filled polymers. In one variation, the substrate is stainless steel. Combinations of materials and coated variants of materials may be used as well.

When it is desirable to use aluminum as a substrate, aluminum foil is a suitable material. Examples of alumina and silicon based materials BCR171 (an alumina of defined surface area greater than 2 $m^2/g$ from Aldrich, St. Louis, MO) and a silicon wafer as used in the semiconductor industry.

Typically, it is desirable that the substrate have relatively few, or substantially no, surface irregularities. Although a variety of supports may be used, supports that have an impermeable surface, or an impermeable surface coating, are typically desirable. Illustrative examples of such supports include metal foils, smooth metal surfaces, nonporous ceramics, and the like. Alternatively, or in addition, to preferred substrates having an impermeable surface, the substrate surface expanse is characterized by a contiguous surface area of about 20 $mm^2$. Alternatively, or in addition, to preferred substrates having an impermeable surface, the substrate surface expanse is characterized by a contiguous surface area of greater than 1 $mm^2$, preferably 10 $mm^2$, more preferable 50 $mm^2$ and still more preferably 100 $mm^2$, and a material density of greater than 0.5 g/cc. In contrast, non-preferred substrates typically have a substrate density of less than 0.5 g/cc, such as, for example, yarn, felts and foam, or have a surface area of less than 1 $mm^2$/particle such as, for example small alumina particles, and other inorganic particles, as it is difficult on these types of surfaces to generate therapeutic quantities of a drug aerosol with less than 10% drug degradation via vaporization.

In one variation, the disclosure teaches a stainless steel foil substrate. A hollow, stainless steel tube may be used as the drug-film substrate. In other variations, aluminum foil is used as a substrate for testing drug.

In a device designed to rapidly heat a foil substrate via electrical resistance heating to vaporize a drug film coated onto the substrate for the purpose of generating a condensation aerosol, the foil substrate must have consistent, uniform electrical contact with the electrical circuit. Inconsistent electrical contact results in localized hot and cool spots on the foil substrate which in turn can have a negative impact on efficiency of the vaporization of the drug resulting in lower, inconsistent emitted dose and can cause degradation of the drug resulting in higher levels of impurities. In addition, after attachment of the foil substrate to the electrical circuit, the foil substrate should maintain a consistent configuration, such as retaining flatness between the electrical contacts or maintaining a controlled arc between the electrical contacts to enable consistent coating of the drug film onto the foil substrate and to maintain consistent distance between the foil substrate and the inside surfaces of the airway in the device. Uneven surfaces in the foil substrate can result in pooling of the drug in low points of the foil substrate during spray coating resulting in localized higher density coating regions and flow of drug away from high spots on the foil substrate resulting in lower density coating regions.

Stainless steel foil substrates suitable for use in an electrical resistance heating-based condensation aerosol device must be extremely thin when considering the design of a portable, battery operated condensation aerosol device—on the order of 0.002" (0.05 mm) or less (thicker foil substrates can be used in the design of less portable, bench top condensation aerosol systems that are mains powered where the power budget is not a significant design consideration). The heat capacity of the stainless steel foil substrate increases proportionally to the thickness of the stainless steel foil. This in turn impacts the power required to heat the foil substrate rapidly. In addition, the electrical resistance is also directly proportional to the thickness of the foil substrate. The electrical resistance decreases as the thickness of the foil substrate increases. Reduced electrical resistance further drives an increase in power required to heat the foil substrate rapidly. In designs for a portable, handheld, battery operated aerosol generation device for drug delivery, power requirements must be minimized to ensure a reasonable device size. Therefore, it is critical to minimize the thickness of the stainless steel foil substrate to enable rapid heating, such as heating the substrate from 20 C to 400 C in 300 ms or less. Rapid heating is necessary to ensure efficient vaporization of the drug film early in the inhalation cycle to ensure sufficient inhalation chaser volume is available to transport the aerosol particles to the deep lung.

Copper is a standard material used for electrical traces in printed circuit boards (PCBs) and stainless steel is a preferred material for use as a substrate on which a drug film is coated. To create an electrical resistance circuit, the stainless steel must be attached to the copper. As noted above, the foil substrate suitable for use in a portable, battery operated condensation aerosol generation device must be thin.

Soldering is a standard means of creating electrical connections in electrical circuits. While soldering works well for some metals such as copper, it does not work well between copper and bare stainless steel. A method of enabling soldering between copper and stainless steel is to apply gold plating to the regions of the stainless steel where the solder joints will be made. To prevent the gold plating from covering the regions of the stainless steel that will serve as the substrate for the drug film, specific regions of the stainless steel must be covered by a mask prior to the gold plating process. As noted above, the foil substrate suitable for use in a portable, battery operated condensation aerosol generation device must be thin. Applying a mask to a thin stainless steel foil prior to gold plating and subsequently removing the mask from the foil without tearing and/or wrinkling the foil is a difficult process and few foil convertors have the capability to perform this operation on thin (0.002" (0.05 mm) or less) stainless steel foils. The need for masking and gold plating the foil substrate is undesired as it adds time and cost to the assembly process and reduces overall yield efficiency.

An alternative to soldering the stainless steel foil substrate to copper to form an electrical resistance circuit is to use laser welding. There are many different reasons why laser welding is superior to soldering.

Soldering, or more appropriately brazing, is a capillary fill system where solder is heated with a gas-oxygen torch, open flame or hot tip soldering iron. When the solder reaches its melting point, the solder then flows across and bridges the metals together. Solder is an alloy that is designed to melt at a lower temperature than the metal being soldered; therefore, it is a different alloy than the metal. The heat used for this process is very high, and thus often results in a visible seam, discoloration or fire stain in the solder area.

Laser welding is a non-contact process in which light energy is used to weld the metals to themselves; this process fuses the metals on a molecular level resulting in a finished product that is all one alloy. Most laser processes weld autogenously, meaning without filler metal, with a minimal heat-affected zone (HAZ) and just enough heat to melt and fuse the material. This produces a high-quality weld joint with minimal thermal distortion. However, welding autogenously does require intimate contact between the mating surfaces. Because the laser is a highly concentrated heat source, the joint generally melts, fuses, and cools extremely quickly. Therefore, materials must be able to endure quick cooling without causing weld defects, such as cracking. When it is necessary to add metal or "filler wire" with the laser welder, the filler material is typically the same as one of the metals being welded.

The heat required for welding is supplied by a tightly focused light beam with a diameter as small as two-thousandths of an inch. Welding is conducted by firing a series of short pulses that melt the metal to create a high-quality weld. Because the laser beam is tightly focused, heat input is minimized and parts can be handled almost immediately. The laser has a finely focused beam resulting in a minimal HAZ or "bombardment Zone." During the welding process, the metal adjacent to the bombardment zone does not become molten. This precision heat source allows the user to weld metal in close proximity of heat sensitive components and results in a seamless, undetectable work zone that is not discolored.

Lasers successfully weld carbon steel, high strength steel, stainless steel, titanium, aluminum, and precious metals as well as dissimilar materials such as welding stainless steel to copper.

The primary types of lasers used in welding and cutting are:

Gas lasers: These lasers use a mixture of gases such as helium and nitrogen. There are also $CO_2$ or carbon dioxide lasers. These lasers use a low-current, high-voltage power source to excite the gas mixture using a lasing medium. Operate in a pulsed or continuous mode. Carbon dioxide lasers use a mixture of high purity carbon dioxide with helium and nitrogen as the lasing medium. $CO_2$ lasers are also used in dual beam laser welding where the beam is split into two equal power beams.

Solid state lasers: (Nd:YAG type and ruby lasers) Operate at micrometer wavelengths. They can be pulsed or operate continuously. Pulsed operation produced joints similar to spot welds but with complete penetration. The pulse energy is 1 to 100 Joules. Pulse time is 1 to 10 milliseconds Diode Lasers In the preferred embodiment, Nd:YAG lasers are used under computer numerical control (CNC) to provide reproducible and accurate welds. Tooling is used to hold the foil substrate in the same orientation for each assembly.

FIG. 25 shows examples of foil substrates soldered and FIG. 26 shows a laser welded to an electrical flex circuit. As can be seen, the soldered foil substrate does not lay flat due to distortion resulting from exposure to excessive heat during the soldering process. In comparison, the foil substrate laser welded to the flex circuit shows a very clean bond between the copper and stainless steel with minimal thermal distortion.

With regard to the composition, the drug is typically coated on the foil substrate in the form of a film. The film may be coated on the foil substrate using any suitable method. The method suitable for coating is often dependent upon the physical properties of the compound and the desired film thickness. One exemplary method of coating a composition on a foil substrate is by preparing a solution of compound (alone or in combination with other desirable compounds) in a suitable solvent, applying the solution to the exterior surface of the foil substrate, and then removing the solvent (e.g., via evaporation, etc.) thereby leaving a film on the foil substrate.

Common solvents include methanol, dichloromethane, methyl ethyl ketone, diethyl ether, acetone, ethanol, isopropyl alcohol, 3:1 chloroform:methanol mixture, 1:1 dichloromethane:methyl ethyl ketone mixture, dimethylformamide, and deionized water. In some instances (e.g., when triamterene is used), it is desirable to use a solvent such as formic acid. Sonication may also be used as necessary to dissolve the compound.

The composition may also be coated on the foil substrate by dipping the substrate into a composition solution, or by spraying, brushing or otherwise applying the solution to the foil substrate. Alternatively, a melt of the drug can be prepared and applied to the foil substrate. For drugs that are liquids at room temperature, thickening agents can be mixed with the drug to permit application of a solid drug film.

The film can be of varying thickness depending on the compound and the maximum amount of thermal degradation desired. In one method, the heating of the composition involves heating a thin film of the composition having a thickness between about 0.1 µm-30 µm to form a vapor. In yet other variations, the composition has a film thickness between about 0.5 µm-21 µm. Most typically, the film thickness vaporized is between 0.5 µm-25 µm.

Power sources typically supply heat or electrical power to the substrate at a rate that achieves a substrate temperature of at least 200° C., preferably at least 250 foil substrate, or more preferably at least 300° C. or 350° C. or as high as 500° C., and produces substantially complete volatilization of the drug composition from the substrate within a period of 2 seconds, preferably, within 1 second, or more preferably within 0.5 seconds. Suitable power sources for portable, handheld drug delivery devices are lithium polymer batteries which are capable of providing high current discharge rates necessary for electrical resistive heating to achieve rapid heating, e.g., to a substrate temperature of at least 200° C., 250° C., 300° C., or 350° C. or as high as 500° C. preferably within 50-500 ms, more preferably in the range of 50-200 ms.

In order to rapidly heat foil substrate via electrical resistance heating to vaporize a drug film coated onto the substrate for the purpose of generating a condensation aerosol, the device must be able to deliver high power (400 to 700 W) to the foil substrate for a brief period of time (up to 300 ms). For a ~10 V system, which can be achieved by connecting three 3.7 V batteries in series, this translates to out currents of 40 to 70 A. Generating this high level of electrical power is a challenge with traditional battery chemistries when the intent is to incorporate this functionality into a handheld, portable, condensation aerosol drug delivery device.

Compact, commercially available lithium polymer batteries have the power and current output that are suitable for use in the construction of a handheld condensation aerosol drug delivery device to drive electrical resistance heating of a relatively large surface area foil substrate. These batteries have current output capabilities in the 40 to 70 A range needed to rapidly heat a drug coated metal foil substrate, such as stainless steel, from 20° C. to a 300° C. to ~500° C. range in 300 ms or less to efficiently vaporize the coated drug. The vaporized drug subsequently condenses to form aerosol particles whose sizes are optimal for delivery to the deep lung. Lithium polymer batteries come in many different sizes or can be custom designed to enable flexibility in packaging into a portable, handheld device.

Battery current discharge capability is specified by its C-rating. The C-rate is a measure of the rate at which a battery is being discharged relative to its maximum capacity. It is defined as the discharge current divided by the theoretical current draw under which the battery would deliver its nominal rated capacity in one hour When heating the thin film of the composition, to avoid decomposition, it is desirable that the vaporized compound should transition rapidly from the heated surface or surrounding heated gas to a cooler environment. This may be accomplished not only by the rapid heating of the substrate, but also by the use of a flow of gas across the surface of the substrate. While a vaporized compound from a surface may transition through Brownian motion or diffusion, the temporal duration of this transition may be impacted by the extent of the region of elevated temperature at the surface, which is established by the velocity gradient of gases over the surface and the physical shape of surface. Typical gas-flow rates used to minimize such decomposition and to generate a desired particle size are in the range of 1-10 L/minute.

The aerosol particles for administration can typically be formed using any of the describe methods at a rate of greater than 108 inhalable particles per second. In some variations, the aerosol particles for administration are formed at a rate of greater than 10 or $10^{10}$ inhalable particles per second. Similarly, with respect to aerosol formation (i.e., the mass of aerosolized particulate matter produced by a delivery device per unit time) the aerosol may be formed at a rate greater than 0.25 mg/second, greater than 0.5 mg/second, or greater than 1 or 2 mg/second. Further, with respect to aerosol formation, focusing on the drug aerosol formation rate (i.e., the rate of drug compound released in aerosol form by a delivery device per unit time), the drug may be aerosolized at a rate greater than 0.05 mg drug per second, greater than 0.1 mg drug per second, greater than 0.5 mg drug per second, or greater than 1 or 2 mg drug per second.

In some variations, the drug condensation aerosols are formed from compositions that provide at least 5% by weight of drug condensation aerosol particles. In other variations, the aerosols are formed from compositions that provide at least 10%, 20%, 30%, 40%, 50%, 60%, or 75% by weight of drug condensation aerosol particles. In still other variations, the aerosols are formed from compositions that provide at least 95%, 99%, or 99.5% by weight of drug condensation aerosol particles.

In some variations, the drug condensation aerosol particles when formed comprise less than 10% by weight of a thermal degradation product. In other variations, the drug condensation aerosol particles when formed comprise less than 5%, 1%, 0.5%, 0.1%, or 0.03% by weight of a thermal degradation product.

In some variations the drug condensation aerosols are produced in a gas stream at a rate such that the resultant aerosols have a MMAD in the range of about 0.1-3 µm. In some variations the geometric standard deviation around the MMAD of the drug condensation aerosol particles is less than 3 µm. In some variations the geometric standard deviation around the MMAD of the drug condensation aerosol particles is less than 5 µm. In other variations, the geometric standard deviation around the MMAD of the drug condensation aerosol particles is less than 2.5 µm, or less than 2 µm.

The disclosure teaches a device for producing a condensation aerosol with vaporization temperature sensitive drugs comprising: an electrically resistive heating element comprising a metal foil substrate configured to vaporize a substance disposed thereon; an electrical current delivery device to drive a precise electrical current profile through the substrate to affect electrical resistive heating at a rate that achieves a precise temperature profile on the substrate sufficient to vaporize all or a portion of the coated drug composition within a period of three seconds or less; and an airway which directs inhalation air over the surface of the substrate to entrain and condense the vaporized drug composition into condensation aerosol particles comprising the substance which exit the mouthpiece end of the airway into the user's mouth to reach the deep lung via the airway passages to effect systemic drug delivery. For example, apomorphine hydrochloride hemihydrate is vaporization temperature sensitive and therefore requires a precise level of temperature control for generating a condensation aerosol.

Delivery Devices

The delivery devices described herein for administering a condensation drug aerosol typically comprise an element for heating the composition to form a vapor and an element allowing the vapor to cool, thereby forming a condensation aerosol. These aerosols are generally delivered via inhalation to lungs of a patient, for local or systemic treatment. Alternatively, however, the condensation aerosols of the invention can be produced in an air stream, for application of drug-aerosol particles to a target site. For example, a stream of air carrying drug-aerosol particles can be applied to treat an acute or chronic skin condition, can be applied during surgery at the incision site, or can be applied to an open wound. The delivery device may be combined with a composition comprising a drug in unit dose form for use as a kit.

The devices described herein may additionally contain a variety of components to facilitate aerosol delivery. For instance, the device may include any component known in the art to control the timing of drug aerosolization relative to inhalation (e.g., breath-actuation). Similarly, the device may include a component to provide feedback to patients on the rate and/or volume of inhalation, or a component to prevent excessive use (i.e., "lockout" feature). The device may further comprise features such as dose counting/logging or tapering methods. In addition, the device may further include a component to prevent use by unauthorized individuals, and a component to record dosing histories. These components may be used alone, or in combination with other components.

The element that allows cooling may be of any configuration. For example, it may be an inert passageway linking the heating means to the inhalation means. Similarly, the element permitting inhalation by a user may be of any configuration. For example, it may be an exit portal that forms a connection between the cooling element and the user's respiratory system.

Typically, the drug supply article is heated to a temperature sufficient to vaporize all or a portion of the film, so that the composition forms a vapor that becomes entrained in a stream of air during inhalation. As noted above, heating of the drug supply article may be accomplished using, for example, an electrically-resistive, drug coated foil substrate connected in an electrical circuit to a power source such as a battery pack disposed in the housing. The heating can be actuated, for example, with a button on the housing or via breath actuation, as is known in the art.

Another device that may be used to form and deliver the aerosols described herein is as follows. The device comprises an element for heating a composition to form a vapor, an element allowing the vapor to cool, thereby forming a condensation aerosol, and an element permitting a user to inhale the aerosol. The device also comprises an upper external housing member and a lower external housing member that fit together.

The downstream end of each housing member is gently tapered for insertion into a user's mouth. The upstream end of the upper and lower housing members are slotted (either one or both are slotted), to provide for air intake when a user inhales. The upper and lower housing members when fitted together define a chamber. Positioned within chamber is a drug supply unit.

In one variation of the devices used, the device includes a drug composition delivery article composed of the substrate, a film of the selected drug composition on the substrate surface, and an electrical power source for supplying electrical current through the foil substrate at a rate effective to heat the substrate to a temperature greater than 200° C. or in other embodiments to a temperature greater than 250° C., 300° C. or 350° C., 300° C. or 350° C., or as high as 500° C. and to produce substantially complete volatilization of the drug composition within a period of 2 seconds or less and more preferable in a period of 1 second or less.

Other drug supply articles that may be used in combination with the devices described herein. Various methods of coatings are known in the art and/or have been described above.

The illustrative heating element shown as an electrical resistive foil substrate that produces heat when a current flows through it. Acceptable energy sources can supply power to heat the drug coated foil substrate to the drug supply article at rates that rapidly achieve a temperature sufficient to completely vaporize the composition from the support surface. For example, heat sources that achieve a temperature of 200° C. to 500° C. or more within a period of 2 seconds are typical, and 1 second or less is preferred, although it should be appreciated that the temperature chosen will be dependent upon the vaporization properties of the composition, but is typically heated to a temperature of at least about 200° C., preferably of at least about 250° C., more preferably at least about 300° C. or 350° C. Heating the substrate produces a drug composition vapor that in the presence of the flowing gas generates aerosol particles in the desired size range. The presence of the gas flow is generally prior to, simultaneously with, or subsequent to heating the substrate. In one embodiment, the substrate is heated for a period of less than about 1 second, and more preferably for less than about 500 milliseconds, still more preferably for less than about 200 milliseconds. The drug-aerosol particles are inhaled by a subject for delivery to the lung.

The device may also include a gas-flow control valve disposed upstream of the solid support, for limiting gas-flow rate through the condensation region. The gas-flow valve may, for example, include an inlet port communicating with the chamber, and a deformable flap adapted to divert or restrict airflow away from the port increasingly, with increasing pressure drop across the valve. Similarly, the gas-flow valve may include an actuation switch. In this variation, the valve movement would be in response to an air pressure differential across the valve, which for example, could function to close the switch. The gas-flow valve may also include an orifice designed to limit airflow rate into the chamber.

The device may also include a bypass valve communicating with the chamber downstream of the unit for offsetting the decrease in airflow produced by the gas-flow control valve, as the user draws air into the chamber. In this way, the bypass valve could cooperate with the gas-control valve to control the flow through the condensation region of the chamber as well as the total amount of air being drawn through the device. Thus the total volumetric airflow through the device in this variation would be the sum of the volumetric airflow rate through the gas-control valve and the volumetric airflow rate through the bypass valve.

The gas control valve could, for example, function to limit air drawn into the device to a preselected level, e.g., 15 L/minute. In this way, airflow for producing particles of a desired size may be preselected and produced. For example, once this selected airflow level is reached, additional air drawn into the device would create a pressure drop across the bypass valve, which in turn would accommodate airflow through the bypass valve into the downstream end of the device adjacent the user's mouth. Thus, the user senses a full breath being drawn in, with the two valves distributing the total airflow between desired airflow rate and bypass airflow rate.

These valves may be used to control the gas velocity through the condensation region of the chamber and hence to control the particle size of the aerosol particles produced. Typically, the faster the airflow, the smaller the particles are. Thus, to achieve smaller or larger particles, the gas velocity through the condensation region of the chamber may be altered by modifying the gas-flow control valve to increase or decrease the volumetric airflow rate. For example, to produce condensation particles in the size range of about 1-3.5 μm MMAD, a chamber having substantially smooth-surfaced walls would have a selected gas-flow rate in the range of 1-10 L/minute.

Additionally, as will be appreciated by one of skill in the art, particle size may be altered by modifying the cross-section of the chamber condensation region to increase or decrease linear gas velocity for a given volumetric flow rate, and/or the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within a few thousandths of an inch from the substrate surface. Particle size is discussed in more detail below.

Drug Composition Film Thickness

Typically, the drug composition film coated on the substrate has a thickness of between about 0.05-30 m, and typically a thickness between 0.1-30 μm. More typically, the thickness is between about 0.2-30 μm; even more typically, the thickness is between about 0.5-30 μm, and most typically, the thickness is between about 0.5-25 μm. The desirable film thickness for any given drug composition is typically determined by an iterative process in which the desired yield and purity of the condensation aerosol composition are selected or known.

For example, if the purity of the particles is less than that which is desired, or if the percent yield is less than that which is desired, the thickness of the drug film is adjusted to a thickness different from the initial film thickness. The purity and yield are then determined at the adjusted film thickness, and this process is repeated until the desired purity and yield are achieved. After selection of an appropriate film thickness, the area of substrate required to provide a therapeutically effective dose is determined.

Generally, the film thickness for a given drug composition is such that drug-aerosol particles, formed by vaporizing the drug composition by heating the substrate and entraining the vapor in a gas stream, have (i) 10% by weight or less drug-degradation product, more preferably 5% by weight or less, most preferably 2.5% by weight or less and (ii) at least 50% of the total amount of drug composition contained in the film. The area of the substrate on which the drug composition film is formed is selected to achieve an effective human therapeutic dose of the drug aerosol as is described further below.

To determine the thickness of the drug film, one method that can be used is to determine the area of the substrate and calculate drug film thickness using the following relationship:

film thickness (cm)=drug mass (g)/[drug density (g/cm$^3$)×substrate area (cm$^2$)]

The drug mass can be determined by weighing the substrate before and after formation of the drug film or by extracting the drug and measuring the amount analytically. Drug density can be experimentally determined by a variety of techniques, known by those of skill in the art or found in the literature or in reference texts, such as in the CRC Handbook of Chemistry and Physics. An assumption of unit density is acceptable if an actual drug density is not known.

The substrate having a drug film of known thickness was heated to a temperature sufficient to generate a thermal vapor. All or a portion of the thermal vapor was recovered and analyzed for presence of drug-degradation products, to determine purity of the aerosol particles in the thermal vapor. There is a clear relationship between film thickness and aerosol particle purity, whereas the film thickness decreases, the purity increases.

In addition to selection of a drug film thickness that provides aerosol particles containing 10% or less drug-degradation product (i.e., an aerosol particle purity of 90% or more), the film thickness is selected such that at least about 50% of the total amount of drug composition contained in the film is vaporized when the substrate is heated to a temperature sufficient to vaporize the film.

To obtain higher purity aerosols one can coat a lesser amount of drug, yielding a thinner film to heat, or alternatively use the same amount of drug but a larger surface area. Generally, except for, as discussed above, extremely thin thickness of drug film, a linear decrease in film thickness is associated with a linear decrease in impurities.

Thus for the drug composition where the aerosol exhibits an increasing level of drug degradation products with increasing film thicknesses, particularly at a thickness of greater than 0.05-30 μm, the film thickness on the substrate will typically be between 0.05 and 30 μm, e.g., the maximum or near-maximum thickness within this range that allows formation of a particle aerosol with drug degradation less than 5%.

Another approach contemplates generation of drug-aerosol particles having a desired level of drug composition purity by forming the thermal vapor under a controlled atmosphere of an inert gas, such as argon, nitrogen, helium, and the like.

Once a desired purity and yield have been achieved or can be estimated from a graph of aerosol purity versus film thickness and the corresponding film thickness determined, the area of substrate required to provide a therapeutically effective dose is determined.

Substrate Area

As noted above, the surface area of the substrate surface area is selected such that it is sufficient to yield a therapeutically effective dose. The amount of drug to provide a therapeutic dose is generally known in the art and is discussed more below. The required dosage and selected film thickness, discussed above, dictate the minimum required substrate area in accord with the following relationship:

film thickness (cm)×drug density (g/cm$^3$)×substrate area (cm$^2$)=dose (g)

OR

Substrate area (cm$^2$)=dose (g)/[film thickness (cm)× drug density (g/cm$^3$)]

The drug mass can be determined by weighing the substrate before and after formation of the drug film or by extracting the drug and measuring the amount analytically. Drug density can be determined experimentally by a variety of well-known techniques, or may be found in the literature or in reference texts, such as in the CRC. An assumption of unit density is acceptable if an actual drug density is not known.

To prepare a drug supply article comprised of a drug film on a heat-conductive substrate that is capable of administering an effective human therapeutic dose, the minimum substrate surface area is determined using the relationships described above to determine a substrate area for a selected film thickness that will yield a therapeutic dose of drug aerosol.

In some variations, the selected substrate surface area is between about 0.05-500 cm$^2$. In others, the surface area is between about 0.05 and 300 cm$^2$. In one embodiment, the substrate surface area is between 0.05 and 0.5 cm$^2$. In one embodiment, substrate surface areas, are between 0.1 and 0.2 cm$^2$. The actual dose of drug delivered, i.e., the percent yield or percent emitted, from the drug-supply article will depend on, along with other factors, the percent of drug film that is vaporized upon heating the substrate. Thus, for drug films that yield upon heating 100% of the drug film and aerosol particles that have a 100% drug purity, the relationship between dose, thickness, and area given above correlates directly to the dose provided to the user. As the percent yield and/or particle purity decrease, adjustments in the substrate area can be made as needed to provide the desired dose. Also, as one of skill in the art will recognize, larger substrate areas other than the minimum calculated area for a particular film thickness can be used to deliver a therapeutically effective dose of the drug. Moreover as can be appreciated by one of skill in art, the film need not coat the complete surface area if a selected surface area exceeds the minimum required for delivering a therapeutic dose from a selected film thickness.

Dosage of Drug Containing Aerosols

The dose of a drug delivered in the aerosol refers to a unit dose amount that is generated by heating of the drug under defined conditions, cooling the ensuing vapor, and delivering the resultant aerosol. A "unit dose amount" is the total amount of drug in a given volume of inhaled aerosol. The unit dose amount may be determined by collecting the aerosol and analyzing its composition as described herein, and comparing the results of analysis of the aerosol to those of a series of reference standards containing known amounts of the drug. The amount of drug or drugs required in the starting composition for delivery as an aerosol depends on the amount of drug or drugs entering the thermal vapor phase when heated (i.e., the dose produced by the starting drug or drugs), the bioavailability of the aerosol drug or drugs, the volume of patient inhalation, and the potency of the aerosol drug or drugs as a function of plasma drug concentration.

One can determine the appropriate dose of a drug-containing aerosol to treat a particular condition using methods such as animal experiments and a dose-finding (Phase I/II) clinical trial. These experiments may also be used to evaluate possible pulmonary toxicity of the aerosol. One animal experiment involves measuring plasma concentrations of drug in an animal after its exposure to the aerosol. Mammals such as dogs or primates are typically used in such studies, since their respiratory systems are similar to that of a human and they typically provide accurate extrapolation of test results to humans. Initial dose levels for testing in humans are generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered. The actual effective amount of drug for a particular patient can vary according to the specific drug or combination thereof being utilized, the particular composition formulated, the mode of administration and the age, weight, and condition of the patient and severity of the episode being treated.

Particle Size

Efficient aerosol delivery to the lungs requires that the particles have certain penetration and settling or diffusional characteristics. Deposition in the deep lungs occurs by gravitational settling and requires particles to have an effective settling size, defined as mass median aerodynamic diameter (MMAD), typically between 1-3.5 µm. For smaller particles, deposition to the deep lung occurs by a diffusional process that requires having a particle size in the 10-100 nm, typically 20-100 nm range. An inhalation drug-delivery device for deep lung delivery should produce an aerosol having particles in one of these two size ranges, preferably between about 0.1-3 µm MMAD. In other variations the aerosol MMAD is less than 5 µm. Typically, in order to produce particles having a desired MMAD, gas or air is passed over the solid support at a certain flow rate.

During the condensation stage the MMAD of the aerosol is increasing over time. Typically, in variations of the invention, the MMAD increases within the size range of 0.01-3 µm as the vapor condenses as it cools by contact with the carrier gas then further increases as the aerosol particles collide with each other and coagulate into larger particles. Most typically, the MMAD grows from <0.5 micron to >1 micron in less than 1 second. Thus typically, immediately after condensing into particles, the condensation aerosol MMAD doubles at least once per second, often at least 2, 4, 8, or 20 times per second. In other variations, the MMAD increases within the size range of 0.1-3 µm.

Typically, the higher the flow rate, the smaller the particles that are formed. Therefore, in order to achieve smaller or larger particles, the flow rate through the condensation region of the delivery device may be altered. A desired particle size is achieved by mixing a compound in its vapor-state into a volume of a carrier gas, in a ratio such that the desired particle size is achieved when the number concentration of the mixture reaches approximately $10^9$ particles/mL. The particle growth at this number concentration is then slow enough to consider the particle size to be "stable" in the context of a single deep inhalation. This may be done, for example, by modifying a gas-flow control valve to increase or decrease the volumetric airflow rate. To illustrate, condensation particles in the size range 0.1-3 µm MMAD may be produced by selecting the gas-flow rate over the vaporizing drug to be in a range of 1-10 L/minute, preferably in the range of 2-8 L/min.

Additionally, as will be appreciated by one of skill in the art, particle size may also be altered by modifying the cross-section of the chamber condensation region to increase or decrease linear gas velocity for a given volumetric flow rate. In addition, particle size may also be altered by the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within a few thousandths of an inch from the substrate surface.

Analysis of Drug Containing Aerosols

Purity of a drug-containing aerosol may be determined using a number of different methods. It should be noted that when the term "purity" is used, it refers to the percentage of aerosol minus the percent byproduct produced in its formation. Byproducts for example, are those unwanted products produced during vaporization. For example, byproducts include thermal degradation products as well as any unwanted metabolites of the active compound or compounds. Examples of suitable methods for determining aerosol purity are described in Sekine et al., *Journal of Forensic Science* 32:1271-1280 (1987) and in Martin et al., *Journal of Analytic Toxicology* 13:158-162 (1989).

One suitable method involves the use of a trap. In this method, the aerosol is collected in a trap in order to determine the percent or fraction of byproduct. Any suitable trap may be used. Suitable traps include filters, glass wool, impingers, solvent traps, cold traps, and the like. Filters are often most desirable. The trap is then typically extracted with a solvent, e.g. acetonitrile, and the extract subjected to analysis by any of a variety of analytical methods known in the art, for example, gas, liquid, and high performance liquid chromatography particularly useful.

The gas or liquid chromatography method typically includes a detector system, such as a mass spectrometry detector or an ultraviolet absorption detector. Ideally, the detector system allows determination of the quantity of the components of the drug composition and of the byproduct, by weight. This is achieved in practice by measuring the signal obtained upon analysis of one or more known mass(es) of components of the drug composition or byproduct (standards) and then comparing the signal obtained upon analysis of the aerosol to that obtained upon analysis of the standard(s), an approach well known in the art.

In many cases, the structure of a byproduct may not be known or a standard for it may not be available. In such cases, one may calculate the weight fraction of the byproduct by assuming it has an identical response coefficient (e.g. for ultraviolet absorption detection, identical extinction coefficient) to the drug component or components in the drug composition. When conducting such analysis, byproducts present in less than a very small fraction of the drug compound, e.g. less than 0.1% or 0.03% of the drug compound, are typically excluded. Because of the frequent necessity to assume an identical response coefficient between drug and byproduct in calculating a weight percentage of byproduct, it is often more desirable to use an analytical approach in which such an assumption has a high probability of validity. In this respect, high performance liquid chromatography with detection by absorption of ultraviolet light at 225 nm is typically desirable. UV absorption at 250 nm may be used for detection of compounds in cases where the compound absorbs more strongly at 250 nm or for other reasons one skilled in the art would consider detection at 250 nm the most appropriate means of estimating purity by weight using HPLC analysis. In certain cases where analysis of the drug by UV are not viable, other analytical tools such as GCMS or LCMS may be used to determine purity.

It is possible that changing the gas under which vaporization of the composition occurs may also impact the purity.

Other Analytical Methods

Particle size distribution of a drug-containing aerosol may be determined using any suitable method in the art (e.g., cascade impaction). A Next Generation Cascade Impactor (MSP Corporation, Shoreview, MN) linked to a vaporization device by an induction port (USP induction port, MSP Corporation, Shoreview, MN) is one system used for cascade impaction studies.

Inhalable aerosol mass density may be determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the inhalation volume of an inhaling patient, typically about 2-4 liters.

Inhalable aerosol drug mass density may be determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the inhalation volume of an inhaling patient, typically about 2-4 liters. The amount of active drug compound collected in the chamber is determined by extracting the chamber, conducting chromatographic analysis of the extract and comparing the results of the chromatographic analysis to those of a standard containing known amounts of drug.

Inhalable aerosol particle concentration may be determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size may be determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi * D^3 \varphi/6$, where D is a typical particle diameter in the size range (generally, the mean boundary MMADs defining the size range) in µm, $\varphi$ is the particle density (in g/mL) and mass is given in units of picograms ($g^{-12}$).

Rate of inhalable aerosol particle formation may be determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 10 nm to 5 micron particles collected divided by the duration of the collection time.

Rate of aerosol formation may be determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation may be determined, for example, by delivering a drug-containing aerosol into a confined chamber via an inhalation device over a set period of time (e.g., 3 s). Where the aerosol is a pure drug, the amount of drug collected in the chamber is measured as described above. The rate of drug aerosol formation is equal to the amount of drug collected in the chamber divided by the duration of the collection time. Where the drug-containing aerosol comprises a pharmaceutically acceptable excipient, multiplying the rate of aerosol formation by the percentage of drug in the aerosol provides the rate of drug aerosol formation.

Vaporization Temperature Control

Generation of a suitable condensation aerosol with temperature sensitive drugs comprises identifying the temperatures associated with various transition points and either avoiding them (such as the case with apomorphine hydrochloride hemihydrate where the HCl could dissociate between 250° C. and 280° C.) or target the temperature to a precisely controlled temperature profiles that minimizes generation of impurities. If the drug is exposed to temperatures significantly above this range, the purity of the aerosol degrades. In order to prevent the foil substrate from excessive heating, the ramp-up rate of the temperature of the foil substrate is characterized in order to determine when to discontinue delivery of high electric current flow to the foil substrate to prevent the temperature of the foil substrate from overshooting the target temperature for vaporization. Refer to FIG. 1.

In order to maximize the amount of drug that is vaporized, the radiative and convective heat loss from the foil substrate that occurs as the inhaled air passes over the foil substrate must be off-set by supplying additional energy. Once the target temperature is reached, a pulsed electrical current is applied to the foil substrate at a specific frequency to maintain a stable temperature (FIG. 2). Without the pulsing, the temperature of the foil substrate will drop rapidly resulting in a reduced emitted dose. An alternative to pulsing is to deliver a constant current, where that constant current is small enough to not to cause additional heating yet large enough to prevent cooling.

The plateau heating described above can be controlled for constant rates (plateau heating or no change of temperature/time), or tampered cooling or negative (FIG. 3) or progressive heating or positive (FIG. 4) slope rates (change of temperature/time), to optimize the vaporization process, depending on the drug's response to substrate temperatures.

This disclosure can optionally include the use of a by-pass air flow design such as that described in U.S. Pat. No. 7,913,688 to control the flow rate of air that passes over the foil substrate in order to decrease the convective heat loss rate to provide more consistent vaporization of the drug. The foil substrate thickness can be 0.0005-0.002 inches. In some variations the foil substrate thickness can be 0.0005-0.0015 inches. In some variations, the foil substrate thickness can be 0.0005-0.0010 inches.

Temperature Ramp-Up Rate

For apomorphine hydrochloride hemihydrate, it is critical for the foil substrate to reach the vaporization temperature rapidly to minimize exposure of the drug to certain lower temperatures. At a temperature range of around 250° C. to 280° C., the hydrochloride (HCl) could dissociate from the apomorphine. It is important to minimize the time the apomorphine hydrochloride hemihydrate is exposed to this temperature window (250° C. to 280° C.) in order to prevent the dissociation of HCl from apomorphine.

The vaporization temperature is reached in 300 ms or less (FIG. 1). This is achieved by the use of super capacitors which can store energy and then release energy rapidly (high electrical current).

Super capacitors can be charged (preloaded with energy) using energy from a standard power supply or from batteries.

Alternatively, batteries with sufficiently high C-rating can also be used to provide the rapid release of electrical energy to heat the foil substrate in 300 ms or less. The C-rate is a measure of the rate at which a battery is being discharged relative to its maximum capacity. It is defined as the discharge current divided by the theoretical current draw under which the battery would deliver its nominal rated capacity in one hour.

In order to reduce the energy required to heat the foil substrate and in order to aid in achieving a rapid rise in temperature, a thin stainless steel foil substrate is used to minimize thermal mass. The thickness of foil substrates used in condensation aerosol systems using exothermic chemical reactions to heat the foil substrate is typically in the range of about 102 to 127 µm (0.004" to 0.005") thick. For electrically resistive heating systems, thinner foil substrates on the order of 13 to 38 µm (0.0005" to 0.002") thick are more suitable to reduce the power requirements of the controller during the temperature ramp-up phase.

Foil Substrate Design

Figure 6:
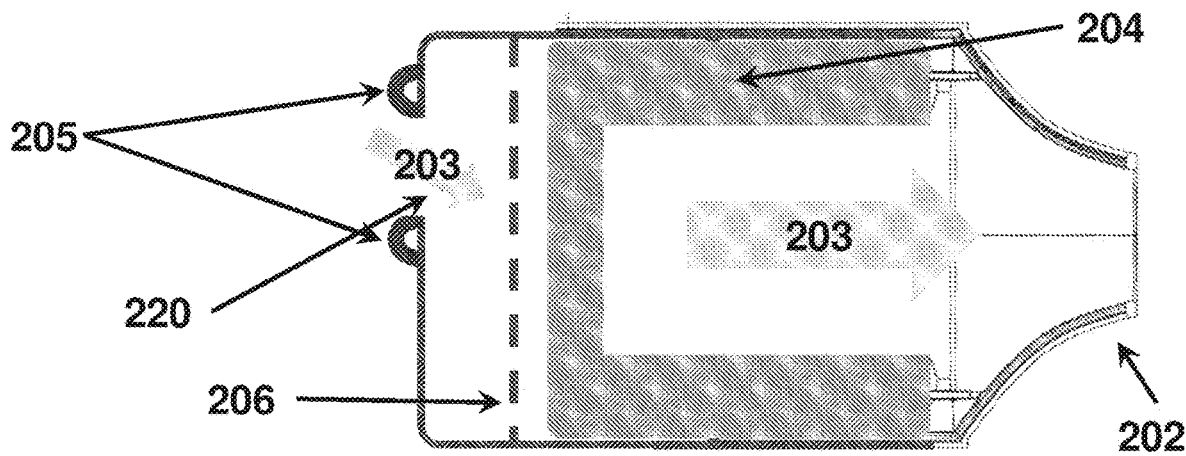
FIG. 6 shows a layer 1 of concepts A—stiffener.
Figure 7:
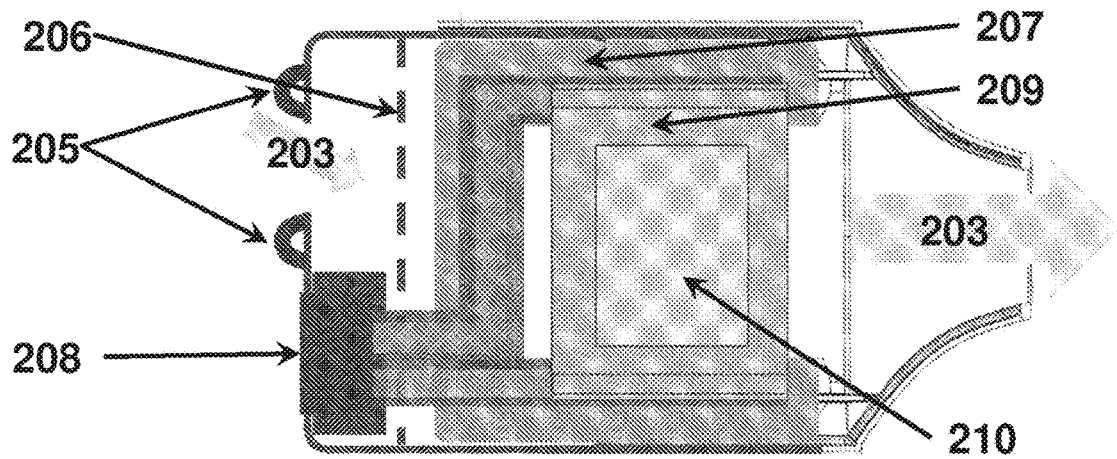
FIG. 7 shows a concept A layer 2—flex circuit mounted on stiffener and foil substrate laser welded to flex circuit.
Figure 8:
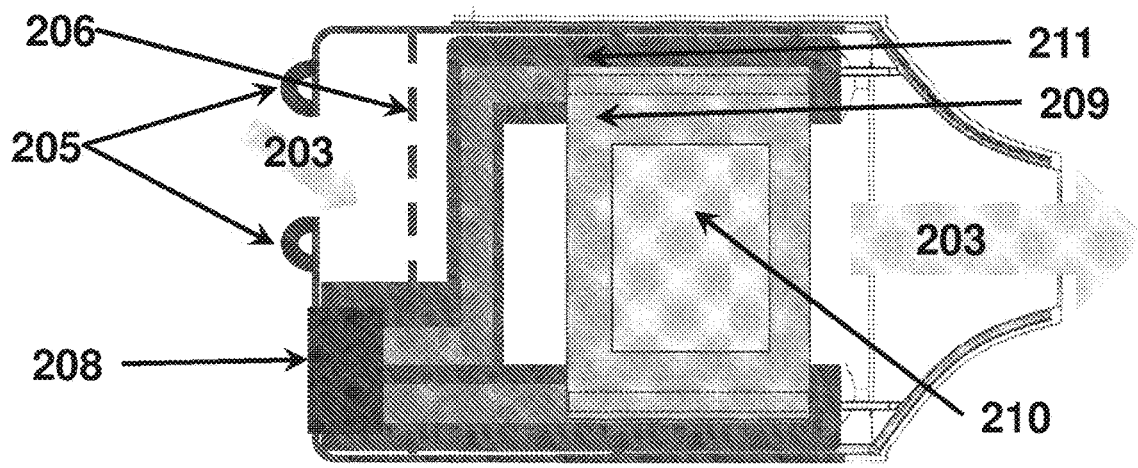
FIG. 8 shows a concept B layer 1—printed circuit board and foil substrate laser welded to flex circuit.

In one embodiment of the invention, the electrically conductive foil substrate is rectangular, approximately 40 mm×30 mm, with 2 opposing edges of the foil substrate electrically connected along the full length of each edge to a flex circuit or printed circuit board (FIGS. 6 to 8). The foil substrate is positioned in an airway supported by the upper and lower halves of the device enclosure. The electrically connected edges run parallel to the main direction of air flow in the airway. The other 2 edges of the foil substrate run perpendicular to the main direction of air flow in the airway and are not supported.

The convective heat loss from the foil substrate that occurs during inhalation as a result of the exposure to the air flow in the airway causes an undesired temperature gradient to develop over the surface of the foil substrate resulting in localized hot and cool spots over the foil substrate surface. Hot spots on the foil substrate during vaporization of the drug can have a negative impact on purity and cool spots can have a negative impact on emitted dose efficiency.

Various methods can be employed to reduce the temperature gradients on the foil substrate for optimal vaporization of the drug. Alternatively, the system can be designed to work around the temperature gradients on the foil substrate surface by avoiding coating of the drug in hot and cool regions of the substrate:

In one embodiment of the invention, turbulence is induced in the air that flows over the foil substrate by directing the air flow through a perforated bulkhead positioned upstream of the foil substrate such that the air flow is uniformly distributed over the foil substrate to provide more uniform convective heat loss over the foil substrate surface (FIG. 16).

In another embodiment of the invention, turbulence is induced in the air that flows over the foil substrate by including surface protrusions of varying shapes to the inside surface of the airway upstream and in the vicinity of the foil substrate such that the air flow is uniformly distributed over the foil substrate to provide more uniform convective heat loss over the foil substrate surface (FIG. 17).

In another embodiment of the invention, flow channels (206) are used in the airway to direct proportioned amounts of air flow to specific regions of the foil substrate such that the air flow is uniformly distributed over the foil substrate to provide more uniform convective heat loss over the foil substrate surface (FIG. 16).

Figure 12:
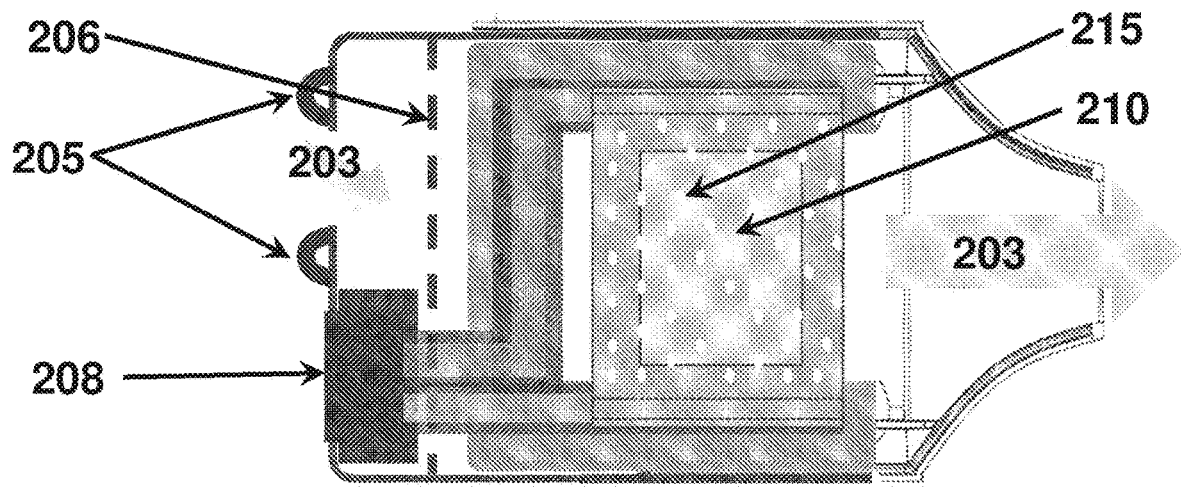
FIG. 12 shows a pattern of holes in foil substrate as thermal conductivity barriers.

In another embodiment of the invention, thermal conductivity barriers in the form of cutout features such as a series of round, obround or other shaped holes placed in a random or non-random pattern in the foil substrate to prevent or reduce the spread of localized cool or hot spots caused by conductive heat transfer (FIG. 12).

Figure 9:
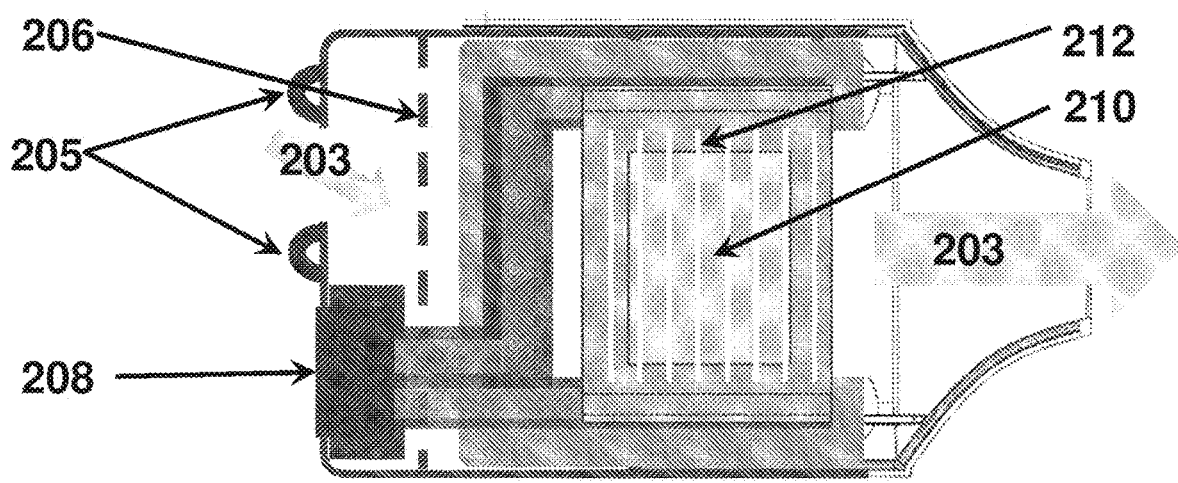
FIG. 9 shows linear slits in foil substrate as thermal conductivity barriers.
Figure 10:
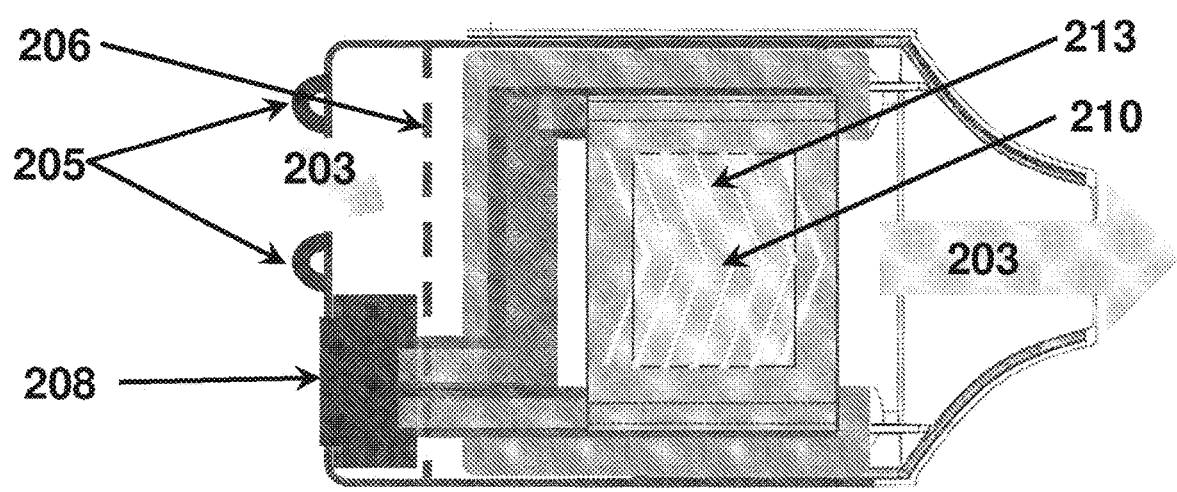
FIG. 10 shows chevron slits in foil substrate as thermal conductivity barriers.
Figure 11:
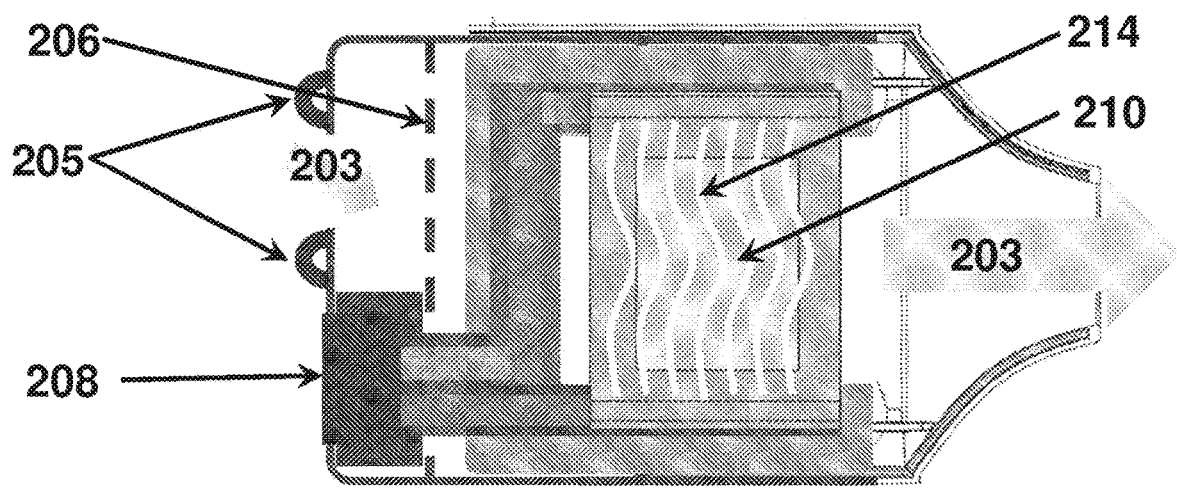
FIG. 11 shows serpentine slits in foil substrate as thermal conductivity barriers.

In another embodiment of the invention, thermal conductivity barriers in the form of cutout features such as a series of slits placed in the foil substrate to prevent or reduce the spread of localized cool or hot spots caused by conductive heat transfer. The slits can be linear, serpentine, chevron, etc. with differing widths in differing orientations relative to the airflow (FIGS. 9 to 11).

Figure 13:
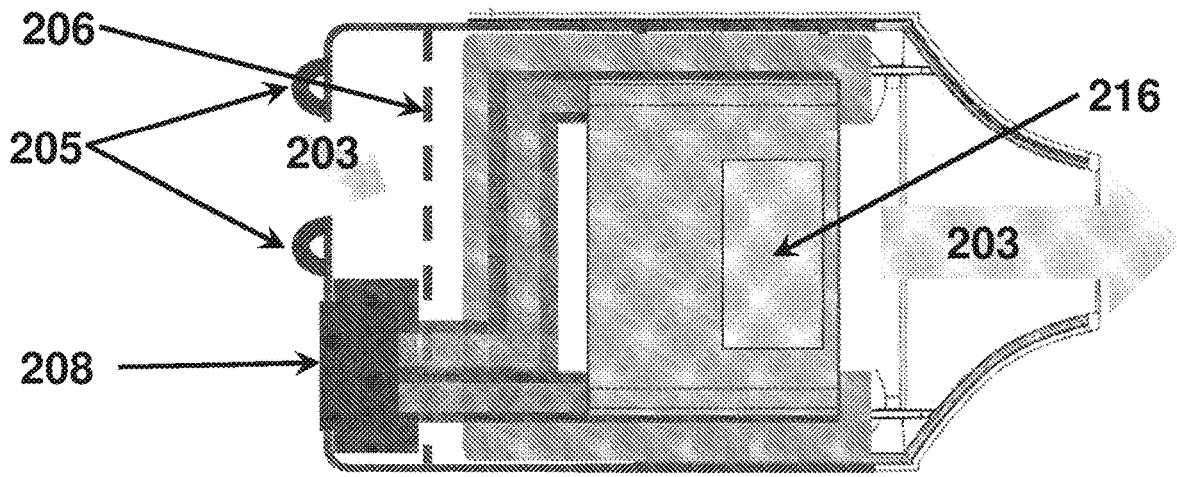
FIG. 13 shows a drug coating biased downstream on foil substrate.
Figure 14:
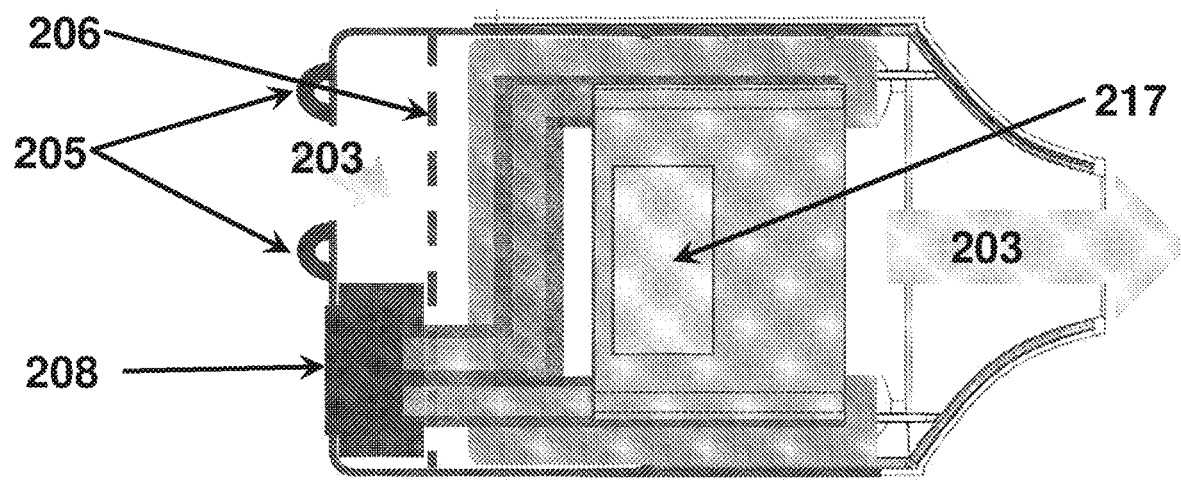
FIG. 14 shows a drug coating biased upstream on foil substrate.

In another embodiment of the invention, the foil substrate is coated only in specific regions of the foil substrate which have been characterized as regions that can consistently achieve the desired target temperature for vaporization of the drug coating. For example, coating regions might be defined as at least partially coating the front half (the geometric center of the coated region is closer to the downstream edge than to the upstream edge of the foil substrate (209)) of the foil substrate (FIG. 13) or at least partially coating the back half (the geometric center of the coated region is closer to the upstream edge than to the downstream edge of the foil substrate (209)) of the foil substrate (FIG. 14). Coating areas can be square, rectangular, trapezoidal, crescent shaped, or other configurations such that the regions the drug is coated on is restricted to the regions with optimal surface temperature for vaporization of the drug (FIGS. 15a and 15b).

EXAMPLES

The following examples are provided for illustrative purposes only and are not intended to limit the scope of the invention.

Example 1: Thermal Mapping of Foil Substrate to Determine Optimal Coating Regions When sufficient electrical current flows through the foil substrate, the inherent electrical resistance of the foil causes the foil substrate surface to increase in temperature. In the absence of air flow through the device, the temperature across the surface of the foil substrate is relatively uniform as can be seen in FIG. 20.

In order to function as an aerosol drug delivery device, air, which is inhaled through the device by the patient, is directed to flow over the heated foil substrate to entrain the vapor and condensation aerosol particles being formed to move the aerosol through the airway to the mouthpiece of the device and then into the patient for delivery of the drug to the deep lung. The air flowing over the foil substrate generally follows a parabolic flow velocity profile with the highest flow velocity towards the center of the airway and the lowest flow velocity towards the edges of the airway. Therefore, the convective heat transfer rate from the foil substrate to the air is higher towards the center of the foil substrate where the air flow velocity is higher. Also, because the thin section of the foil substrate is positioned parallel to the air flow direction, the upstream edge of the foil substrate is cooled by unheated, room temperature air. As the air flows over the foil substrate, the temperature of the air increases due to convection heat transfer from the foil substrate. As a result, the convective heat transfer rate, which is directly proportional to the difference between the temperature of the air and the foil substrate surface, decreases as the air moves from the upstream edge to the downstream edge of the foil substrate. The combination of the parabolic flow velocity profile and the higher heat transfer rates experienced at the upstream edge of the foil substrate results in a temperature gradient across the foil substrate.

In order to capture this heat transfer phenomena empirically, a thermal camera was used to monitor temperature of the foil substrate during heating in the presence of air flow through the device. To enable a thermal camera to measure temperature of the foil substrate surface, the device housing was modified to incorporate a calcium fluoride window that had minimal absorption of visible and infrared wavelengths, so that it was effectively transparent for the infrared thermal measurements. The window was positioned on the device housing in such a way as to enable viewing of the foil substrate. The image in FIG. 21 shows the thermal mapping of a foil substrate in the presence of air flow.

In FIG. 21, the air flows from right to left. As can be seen, the most cooling occurs towards the center of the upstream edge of the foil substrate as expected. This information can be used to determine the optimum drug coating regions on the foil substrate. For drugs more sensitive to vaporization temperatures, thermal mapping can be used to identify hot or cool regions on the foil substrate. The drug coating pattern can be designed to avoid these hot and cool regions such that only the regions showing the most uniform temperature are selected for drug coating.

Example 2: Drugs

One drug that is sensitive to the temperature profile associated with the vaporization process to create a condensation aerosol is apomorphine hydrochloride hemihydrate where the HCl could dissociate at temperatures starting at ~250° C. and vaporization occurs at higher than about 260° C. This invention enables generation of a condensation aerosol with apomorphine hydrochloride hemihydrate with a purity of 90% or better by providing a precisely controlled temperature profile to vaporize the drug from the foil substrate. Apomorphine is sensitive to vaporization temperatures; it exhibits a significant decrease in purity as the substrate temperature increases from 260° C. to 400° C. Therefore, apomorphine is considered to be a vaporization temperature sensitive drug. FIG. 19 shows an example of a vaporization temperature sensitive drug wherein the vaporization temperature affects the aerosol purity. On the other hand, the purity of the aerosols generated with loxapine, fentanyl, zaleplon and alprazolam remain high over a wide range of vaporization temperatures. FIG. 18 shows typical emitted dose and purity of condensation aerosols generated by a drug that is not vaporization temperature sensitive. For loxapine, the purity is 99% or better for vaporization temperatures ranging from about 330° C. to 470° C. The emitted dose is also fairly stable from about 330° C. to 470° C. Zaleplon is similar—the emitted dose is stable and the purity is 99% or better over a similar temperature range. For fentanyl, purity of the aerosol is consistently at ~99% and the emitted dose is 90% or better over a temperature range of about 300° C. to 500° C. Similarly, over a wide range of substrate temperatures (350° C. to 450° C.), the purity of the alprazolam aerosol stays high at ~99% and the emitted dose is also relatively stable at about 90%. The emitted dose for apomorphine can be 20%; alternatively, it can be about 30%; 40%; 50%; 60%; 70%; 80%; 90%; 95%. The degradation product for Apomorphine is in the range of 10% or less.

Example 3: Batteries

Batteries from Kokam, such as the battery model number SLPB8043128H (FIG. 22), has a compact size suitable for a handheld device (43 mm×128 mm×7.6 mm), is light weight (84 g), has reasonable capacity (3.2 Ah), has a nominal voltage of 3.7 V and has a continuous C-rating of 20. This particular battery has continuous discharge current capability of 64 A and a peak discharge current capability of 128 A. Three of these batteries connected in series are sufficient to supply the energy needed to generate a condensation aerosol. A custom sized lithium polymer battery would enable a more compact device layout.

Example 4: Laser Welding

In order to characterize electrical resistance heating of stainless steel foil substrates, a condensation aerosol drug delivery device was assembled with a modified plastic housing. A rectangular section on the side of the housing was cut out and replaced with a calcium fluoride window to enable the use of an infrared thermal camera to capture thermal image of the foil substrate during heating. See FIG. 27.

The thermal camera was set up to capture thermal images every 10 ms (100 images per second). See FIG. 28.

FIG. 29 shows thermal images of different foil substrate configurations which were soldered to the copper traces of a flex circuit at ~200 ms after electrical resistance heating was initiated in the presence of 30 LPM airflow flowing over and under the foil substrate. In the images, the air flow is from right to left. Light color regions are indicative of localized hot zones and darker regions are indicative of cool zones. These images demonstrate how the poor soldering quality achieved between copper and stainless results in inconsistent electrical connectivity and consequently, non-uniform heating of the foil substrate.

FIG. 30 shows thermal images of a foil substrate which was laser welded to the copper traces of a flex circuit at multiple time points after electrical resistance heating was initiated in the presence of 30 LPM airflow flowing over and under the foil substrate. In these images, the air flow is from right to left. As can be seen, when the stainless steel foil substrate is laser welded to the flex circuit, the temperature across the entire surface of the substrate is uniform until convective cooling from the air flowing over the substrate cools the upstream edge.

The description of the various embodiments has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiments described and shown in the figures were chosen and described in order to explain the principles of the invention, the practical application, and to enable others of ordinary skill in the art to understand the invention for various embodiments with various modifications as are suited to the particular use contemplated. All references cited herein are incorporated in their entirety by reference.

The reference numbers in the figures mean:
100: Handheld medical device.
101: Left side LED.
102: Right side or second LED.
103: Cartridge slot.
103A: Keying feature.
104: LCD display (optional).
105: Batteries.
106: Printed Circuit Board (PCB).
$10^7$: Air inlet with a grill.
108: Device enclosure.
200: Single dose disposable cartridge.
201: Connector and air flow interface.
202: Air outlet, in this case adapted as a mouthpiece.
203: Air flow direction defining the airway in the cartridge.
204: Stiffener as example of support for the flex circuit in dose cartridge.
205: Pneumatic sealing gasket for air inlet.
206: Perforated bulkhead.
207: Flex circuit to carry current to foil substrate.
208: Electrical Connector to energize foil substrate.
209: Foil substrate.
210: Area where the drug composition has been coated on the foil substrate (can be single or double sided).
211: Traces in PCB to carry current to foil substrate.
212: Linear slits.
213: Chevron slits.
214: Serpentine slits.
215: Holes.
216: Drug composition coated area biased towards the downstream edge of the foil substrate.
217: Drug composition coated area biased towards upstream edge of the foil substrate.
218: Drug composition coated area with trapezoidal shape.
219: Image of foil substrate post aerosolization showing hot (dark) zones.
220: Air inlet.
301: Form drag.
302: Laminar flow.
303: Turbulent flow.

What is claimed is:

1. A drug device for producing an alprazolam condensation aerosol by thermal vaporization of alprazolam comprising:
   a disposable cartridge (200); and
   a handheld medical device (100), comprising:
   a) one or more air inlets (107);
   b) one or more air outlets (103);
   c) one or more batteries (105) to provide electric current;
   d) one or more connectors to electrically connect the device (100) to the disposable cartridge (200) comprising an alprazolam composition (210) coated on a foil substrate (209); and
   e) one or more electrical current delivery devices (106) to control the release of electric current to the disposable cartridge (200);
      said air inlets ($10^7$) and air outlets (103) defining an airway;
      at least one of the air outlets (103) being configured as a housing to attach said disposable cartridge (200);
      said electrical current delivery devices (106) being configured to drive a precise electrical current profile to the foil substrate (209) of the disposable cartridge (200) to affect electrical resistive heating at a rate that achieves a precise temperature profile with a controllable ramp-up to a target temperature and heating rate; and
      the temperature profile is suitable to vaporize a therapeutically effective amount of alprazolam composition (210) coated on the foil substrate (209) of the cartridge (200) within a period of 3 seconds or less followed by condensation inside the cartridge of the resulting vapor to form alprazolam aerosol particles wherein the one or more connectors and the foil substrate (209) are electrically connected through a printed circuit board (211) or a flex circuit (207).

2. The device of claim 1, wherein said ramp-up target temperature is between 15° and 550° C.

3. The device of claim 1, wherein said ramp-up target temperature is between 20° and 500° C.

4. The device of claim 1, wherein said ramp-up target temperature is between 25° and 450° C.

5. The device of any of claim 1, wherein the ramp-up time is between 50 and 200 ms.

6. The device of claim 1, wherein the ramp-up time is between 50 and 115 ms.

7. The device of claim 1, wherein the foil substrate (209) is heated at 3 to 10° C./ms in the ramp-up time.

8. The device of claim 1, wherein said heating rate is selected from one of plateau heating, tampered cooling or progressive heating, or a combination thereof.

9. The device of claim 1, wherein the batteries (105) are able to provide a peak electric current higher than 30 A and a voltage of 8-13 V.

10. The device of claim 1, wherein the batteries (105) are able to provide a peak electric current higher than 100 A and a voltage of 9-12 V.

11. The device of claim 1, wherein the batteries (105) are lithium polymer batteries.

12. The device of claim 1, which further comprises a device enclosure (108).

13. The device of claim 1, which further comprises means for verifying the correct attachment (103A) of the disposable cartridge (200) into the housing of the device (103).

14. The device of claim 13, wherein the means for verifying the correct attachment (103A) of the disposable cartridge (200) into the housing of the device (103) comprise verification of electrical contact.

15. The device of claim 13, wherein the means for verifying the correct attachment (103A) of the disposable cartridge (200) into the housing of the device (103) comprise a proximity sensor.

16. The device of claim 13, wherein the means for verifying the correct attachment (103A) of the disposable cartridge (200) into the housing of the device (103) comprise a mechanical or optical switch.

17. The device of claim 1, which further comprises means for uniquely recognizing the disposable cartridge (200).

18. The device of claim 17, wherein the means for uniquely recognizing the disposable cartridge (200) are selected from RFID tag, bar code, QR code, read/write chip or combinations thereof.

19. The device of claim 1, which further comprises means for controlling the temperature of the foil substrate (209) in the disposable cartridge (200) by sensing the temperature of the foil substrate (209) and feeding the foil substrate temperature information to the electrical current delivery device (106) to modify the electric current delivery in order to achieve the required temperature.

20. The device of claim 19, wherein the means for controlling the temperature of the foil substrate (209) in the disposable cartridge (200) comprise the measurement of electrical resistance across the foil substrate.

21. The device of claim 19, wherein the means for controlling the temperature of the foil substrate (209) in the disposable cartridge (200) comprise optical measurement.

22. The device of claim 19, wherein the means for controlling the temperature of the foil substrate (209) in the disposable cartridge (200) comprise direct contact measurement with a thermocouple.

23. The device of claim 1, which further comprises a pneumatic sealing interface between the air outlet (103) of the device (100) and the air inlet (220) of the cartridge (200).

24. The device of claim 1, wherein the foil substrate (209) is rectangular with two opposing edges of the foil substrate electrically connected along the full length of each edge to the printed circuit board (211) or to the flex circuit (207) and the electrically connected edges run parallel to the main direction of air flow in the airway.

25. The device of claim 1, wherein the foil substrate (209) and the printed circuit board (211) or the flex circuit (207) are made of different metals.

26. The device of claim 25, wherein the foil substrate (209) and the printed circuit board (211) or the flex circuit (207) are laser welded.

* * * * *